US012559557B2

(12) United States Patent
Alt et al.

(10) Patent No.: US 12,559,557 B2
(45) Date of Patent: *Feb. 24, 2026

(54) METHODS AND COMPOSITIONS RELATING TO ANTI-PD1 ANTIBODY REAGENTS

(71) Applicant: THE CHILDREN'S MEDICAL CENTER CORPORATION, Boston, MA (US)

(72) Inventors: Frederick W. Alt, Cambridge, MA (US); Ming Tian, Boston, MA (US); Hwei-Ling Cheng, Northborough, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/870,010

(22) Filed: Jul. 21, 2022

(65) Prior Publication Data

US 2023/0192855 A1     Jun. 22, 2023

Related U.S. Application Data

(62) Division of application No. 16/608,275, filed as application No. PCT/US2018/030350 on May 1, 2018, now Pat. No. 11,427,636.

(60) Provisional application No. 62/492,533, filed on May 1, 2017.

(51) Int. Cl.
| | | |
|---|---|---|
| *A61K 39/00* | (2006.01) | |
| *C07K 16/28* | (2006.01) | |
| *A61K 35/17* | (2015.01) | |

(52) U.S. Cl.
CPC ... *C07K 16/2818* (2013.01); *A61K 39/001111* (2018.08); *C07K 16/2803* (2013.01); *A61K 35/17* (2013.01); *C07K 2317/21* (2013.01); *C07K 2317/24* (2013.01); *C07K 2317/565* (2013.01)

(58) Field of Classification Search
CPC .................. A61K 39/001111; C07K 2317/565
See application file for complete search history.

(56) References Cited

U.S. PATENT DOCUMENTS

| | | | |
|---|---|---|---|
| 9,217,034 | B2 | 12/2015 | Li et al. |
| 2009/0217401 | A1 | 8/2009 | Korman et al. |
| 2014/0220021 | A1 | 8/2014 | Shibayama et al. |
| 2017/0044259 | A1 | 2/2017 | Tipton et al. |
| 2020/0181265 | A1 | 6/2020 | Alt et al. |

FOREIGN PATENT DOCUMENTS

| | | |
|---|---|---|
| JP | 2006340714 A | 12/2006 |
| JP | 2011526674 A | 10/2011 |
| JP | 2015518826 A | 7/2015 |
| JP | 2016533763 A | 11/2016 |
| WO | 2006121168 A1 | 11/2006 |
| WO | 2014055648 A1 | 4/2014 |
| WO | 2015112790 A2 | 7/2015 |
| WO | 2016/210129 A1 | 12/2016 |
| WO | 2016197497 A1 | 12/2016 |
| WO | 2017011580 A1 | 1/2017 |
| WO | 2017/058859 A1 | 4/2017 |

OTHER PUBLICATIONS

Casset, Florence, et al. "A peptide mimetic of an anti-CD4 monoclonal antibody by rational design." Biochemical and biophysical research communications 307(1): 198-205 Jul. 18, 2003.

"Heise et al. ""Molecular analysis of a UDP-GlcNAc.polypeptide alpha-N-acetylglucosaminyltransferase implicated in the initiation of mucin-type O-glycosylation in Trypanosoma cruzi"" Glycobiology. Aug. 2009, Epub May 25, 2009, vol. 19, No. 8; pp. 918-933".

Holm et al. "Functional mapping and single chain construction of the anti-cytokeratin 8 monoclonal antibody TS1." Molecular Immunology 44(6): 1075-1084 2007.

Kuraoka et al. "Complex Antigens Drive Permissive Clonal Selection in Germinal Centers" Immunity. Mar. 15, 2016, Epub Mar. 3, 2016, vol. 44, No. 3; pp. 542-554.

MacCallum et al. "Antibody-antigen interactions: contact analysis and binding site topography." Journal of molecular biology 262(5): 732-745 1996.

Masuda et al. "The role of interface framework residues in determining antibody VH/VL interaction strength and antigen-binding affinity." The FEBS journal 273.10 (2006): 2184-2194.

Panka et al. "Variable region framework differences result in decreased or increased affinity of variant anti-digoxin antibodies." Proceedings of the National Academy of Sciences 85.9 (1988): 3080-3084.

Rudikoff et al. "Single amino acid substitution altering antigen-binding specificity." Proceedings of the National Academy of Sciences 79(6): 1979-1983 Mar. 1982.

Vander Heiden et al. "Dysregulation of B Cell Repertoire Formation in Myasthenia Gravis Patients Revealed through Deep Sequencing" Journal of Immunology. Feb. 15, 2017, Epub Jan. 13, 2017, vol. 198, No. 4; pp. 1460-1474.

(Continued)

*Primary Examiner* — Nelson B Moseley, II
*Assistant Examiner* — Dennis J Sullivan
(74) *Attorney, Agent, or Firm* — NIXON PEABODY LLP; David S. Resnick; Nicole D. Kling

(57) ABSTRACT

Described herein are novel anti-PD1 antibody reagents (e.g., antibodies, antigen-binding fragments thereof, and/or chimeric antigen receptors). Also described herein antibody-drug conjugates or kits comprising the disclosed antibody reagents, as well as methods of treating cancer by administering the disclosed antibody reagents.

15 Claims, 9 Drawing Sheets

Specification includes a Sequence Listing.

(56)         References Cited

OTHER PUBLICATIONS

Almagro et al. "Progress and challenges in the design and clinical development of antibodies for cancer therapy." Frontiers in immunology 8: 1751 (2018).

Muyldermans. "Applications of nanobodies." Annual review of animal bioscience 9.1: 401-421 (2021).

Muyldermans. "A guide to: generation and design of nanobodies." The FEBS journal 288.7: 2084-2102 (2021).

Winkler et al. "Changing the antigen binding specificity by single point mutations of an anti-p24 (HIV-1) antibody." The journal of Immunology 165.8: 4505-4514 (2000).

PD1 binding activity

Antibody concentration

CD28 binding activity

Antibody concentration

CTLA4 binding activity

Antibody concentration

METHODS AND COMPOSITIONS RELATING TO ANTI-PD1 ANTIBODY REAGENTS

CROSS-REFERENCE TO RELATED APPLICATIONS

This application is a divisional under 35 U.S.C. § 121 of co-pending U.S. application Ser. No. 16/608,275 filed Oct. 25, 2019 issued as U.S. Pat. No. 11,427,636 on Aug. 30, 2022, which is a 35 U.S.C. § 371 National Phase Entry Application of International Application No. PCT/US2018/030350 filed May 1, 2018, which designates the U.S. and claims benefit under 35 U.S.C. § 119(e) of U.S. Provisional Application No. 62/492,533 filed May 1, 2017, the contents of which are incorporated herein by reference in their entireties.

SEQUENCE LISTING

The instant application contains a Sequence Listing which has been submitted electronically in XML file format and is hereby incorporated by reference in its entirety. Said XML copy, created on Jan. 26, 2023, is named 701039-089340USD1_SL.xml and is 279,517 bytes in size.

TECHNICAL FIELD

The technology described herein relates to antibodies and antibody-based reagents that are specific for PD1 and methods of using those compositions, e.g., to treat cancer.

BACKGROUND

PD1 (Programmed Death 1) is a therapeutic target for the treatment of cancer and therapeutic anti-PD1 antibodies exist. However, the specificity and affinity of these antibodies for PD1 are not optimal, as a result of the limiting systems in which the antibodies were originally developed.

SUMMARY

Described herein are the development and characterization of anti-PD1 antibodies demonstrated to have high specificity and binding affinity. These antibodies are developed using a system which harnesses the natural affinity maturation processes in order to provide new therapeutic antibodies with significantly improved affinity and specificity.

In one aspect of any of the embodiments, described herein is an antibody, antibody reagent, antigen-binding fragment thereof, or chimaeric antigen receptor (CAR), that specifically binds an PD1 polypeptide, said antibody reagent, antigen-binding portion thereof, or CAR comprising at least one heavy or light chain complementarity determining region (CDR) selected from the group consisting of (a) a heavy chain CDR1 having the amino acid sequence of SEQ ID NO: 23;
    (b) a heavy chain CDR2 having the amino acid sequence of SEQ ID NO: 24;
    (c) a heavy chain CDR3 having the amino acid sequence of SEQ ID NO: 25;
    (d) a light chain CDR1 having the amino acid sequence of SEQ ID NO: 26;
    (e) a light chain CDR2 having the amino acid sequence of SEQ ID NO: 27; and (f) a light chain CDR3 having the amino acid sequence of SEQ ID NO: 28; or
selected from the group consisting of:
    (a) a heavy chain CDR1 having the amino acid sequence of SEQ ID NO: 29;
    (b) a heavy chain CDR2 having the amino acid sequence of SEQ ID NO: 30;
    (c) a heavy chain CDR3 having the amino acid sequence of SEQ ID NO: 31;
    (d) a light chain CDR1 having the amino acid sequence of SEQ ID NO: 32;
    (e) a light chain CDR2 having the amino acid sequence of SEQ ID NO: 33; and
    (f) a light chain CDR3 having the amino acid sequence of SEQ ID NO: 34; or
selected from the group consisting of:
    (a) a heavy chain CDR1 having the amino acid sequence of SEQ ID NO: 35;
    (b) a heavy chain CDR2 having the amino acid sequence of SEQ ID NO: 36;
    (c) a heavy chain CDR3 having the amino acid sequence of SEQ ID NO: 37;
    (d) a light chain CDR1 having the amino acid sequence of SEQ ID NO: 38;
    (e) a light chain CDR2 having the amino acid sequence of SEQ ID NO: 39; and
    (f) a light chain CDR3 having the amino acid sequence of SEQ ID NO: 40; or
selected from the group consisting of:
    (a) a heavy chain CDR1 having the amino acid sequence of SEQ ID NO: 41;
    (b) a heavy chain CDR2 having the amino acid sequence of SEQ ID NO: 42;
    (c) a heavy chain CDR3 having the amino acid sequence of SEQ ID NO: 43;
    (d) a light chain CDR1 having the amino acid sequence of SEQ ID NO: 44;
    (e) a light chain CDR2 having the amino acid sequence of SEQ ID NO: 45; and
    (f) a light chain CDR3 having the amino acid sequence of SEQ ID NO: 46; or
selected from the group consisting of:
    (a) a heavy chain CDR1 having the amino acid sequence of SEQ ID NO: 47;
    (b) a heavy chain CDR2 having the amino acid sequence of SEQ ID NO: 48;
    (c) a heavy chain CDR3 having the amino acid sequence of SEQ ID NO: 49;
    (d) a light chain CDR1 having the amino acid sequence of SEQ ID NO: 50;
    (e) a light chain CDR2 having the amino acid sequence of SEQ ID NO: 51; and
    (f) a light chain CDR3 having the amino acid sequence of SEQ ID NO: 52; or
selected from the group consisting of:
    (a) a heavy chain CDR1 having the amino acid sequence of SEQ ID NO: 53;
    (b) a heavy chain CDR2 having the amino acid sequence of SEQ ID NO: 54;
    (c) a heavy chain CDR3 having the amino acid sequence of SEQ ID NO: 55;
    (d) a light chain CDR1 having the amino acid sequence of SEQ ID NO: 56;
    (e) a light chain CDR2 having the amino acid sequence of SEQ ID NO: 57; and
    (f) a light chain CDR3 having the amino acid sequence of SEQ ID NO: 58; or selected from the group consisting of:

(a) a heavy chain CDR1 having the amino acid sequence of SEQ ID NO: 59;

(b) a heavy chain CDR2 having the amino acid sequence of SEQ ID NO: 60;

(c) a heavy chain CDR3 having the amino acid sequence of SEQ ID NO: 61;

(d) a light chain CDR1 having the amino acid sequence of SEQ ID NO: 62;

(e) a light chain CDR2 having the amino acid sequence of SEQ ID NO: 63; and (f) a light chain CDR3 having the amino acid sequence of SEQ ID NO: 64; or selected from the group consisting of:

(a) a heavy chain CDR1 having the amino acid sequence of SEQ ID NO: 65;

(b) a heavy chain CDR2 having the amino acid sequence of SEQ ID NO: 66;

(c) a heavy chain CDR3 having the amino acid sequence of SEQ ID NO: 67;

(d) a light chain CDR1 having the amino acid sequence of SEQ ID NO: 68;

(e) a light chain CDR2 having the amino acid sequence of SEQ ID NO: 69; and (f) a light chain CDR3 having the amino acid sequence of SEQ ID NO: 70; or selected from the group consisting of:

(a) a heavy chain CDR1 having the amino acid sequence of SEQ ID NO: 71;

(b) a heavy chain CDR2 having the amino acid sequence of SEQ ID NO: 72;

(c) a heavy chain CDR3 having the amino acid sequence of SEQ ID NO: 73;

(d) a light chain CDR1 having the amino acid sequence of SEQ ID NO: 74;

(e) a light chain CDR2 having the amino acid sequence of SEQ ID NO: 75; and (f) a light chain CDR3 having the amino acid sequence of SEQ ID NO: 76; or selected from the group consisting of:

(a) a heavy chain CDR1 having the amino acid sequence of SEQ ID NO: 77;

(b) a heavy chain CDR2 having the amino acid sequence of SEQ ID NO: 78;

(c) a heavy chain CDR3 having the amino acid sequence of SEQ ID NO: 79;

(d) a light chain CDR1 having the amino acid sequence of SEQ ID NO: 80;

(e) a light chain CDR2 having the amino acid sequence of SEQ ID NO: 81; and (f) a light chain CDR3 having the amino acid sequence of SEQ ID NO: 82; or selected from the group consisting of:

(a) a heavy chain CDR1 having the amino acid sequence of SEQ ID NO: 83;

(b) a heavy chain CDR2 having the amino acid sequence of SEQ ID NO: 84;

(c) a heavy chain CDR3 having the amino acid sequence of SEQ ID NO: 85;

(d) a light chain CDR1 having the amino acid sequence of SEQ ID NO: 86;

(e) a light chain CDR2 having the amino acid sequence of SEQ ID NO: 87; and (f) a light chain CDR3 having the amino acid sequence of SEQ ID NO: 88; or a conservative substitution variant of one or more of (a)-(f).

In some embodiments of any of the aspects, the antibody, antibody reagent, antigen-binding portion thereof, or CAR heavy chain CDRs having the amino acid sequences of SEQ ID NOs: 23-25, or 29-31, or 35-37, or 41-43, or 47-49, or 53-55, or 59-61, or 65-67, or 71-73, or 77-79, or 83-85, or a conservative substitution variant of such amino acid sequence. In some embodiments of any of the aspects, the antibody, antibody reagent, antigen-binding portion thereof, or CAR comprises light chain CDRs having the amino acid sequences of SEQ ID NOs: 26-28, or 32-34, or 38-40, or 44-46, or 50-52, or 56-58, or 62-64, or 68-70, or 74-76, or 80-82, or 86-88, or a conservative substitution variant of such amino acid sequence. In some embodiments of any of the aspects, the antibody, antibody reagent, antigen-binding portion thereof, or CAR comprises:

heavy chain CDRs having the amino acid sequences of SEQ ID NOs: 23-25 and light chain CDRs having the amino acid sequences of SEQ ID NOs: 26-28 or a conservative substitution variant of such amino acid sequence; or heavy chain CDRs having the amino acid sequences of SEQ ID NOs: 29-31 and light chain CDRs having the amino acid sequences of SEQ ID NOs: 32-34 or a conservative substitution variant of such amino acid sequence; or heavy chain CDRs having the amino acid sequences of SEQ ID NOs: 35-37 and light chain CDRs having the amino acid sequences of SEQ ID NOs: 38-40 or a conservative substitution variant of such amino acid sequence; or heavy chain CDRs having the amino acid sequences of SEQ ID NOs: 41-43 and light chain CDRs having the amino acid sequences of SEQ ID NOs: 44-46 or a conservative substitution variant of such amino acid sequence; or heavy chain CDRs having the amino acid sequences of SEQ ID NOs: 47-49 and light chain CDRs having the amino acid sequences of SEQ ID NOs: 50-52 or a conservative substitution variant of such amino acid sequence; or heavy chain CDRs having the amino acid sequences of SEQ ID NOs: 53-55 and light chain CDRs having the amino acid sequences of SEQ ID NOs: 56-58 or a conservative substitution variant of such amino acid sequence; or heavy chain CDRs having the amino acid sequences of SEQ ID NOs: 59-61 and light chain CDRs having the amino acid sequences of SEQ ID NOs: 62-64 or a conservative substitution variant of such amino acid sequence; or heavy chain CDRs having the amino acid sequences of SEQ ID NOs: 65-67 and light chain CDRs having the amino acid sequences of SEQ ID NOs: 68-70 or a conservative substitution variant of such amino acid sequence; or heavy chain CDRs having the amino acid sequences of SEQ ID NOs: 71-73 and light chain CDRs having the amino acid sequences of SEQ ID NOs: 74-76 or a conservative substitution variant of such amino acid sequence; or heavy chain CDRs having the amino acid sequences of SEQ ID NOs: 77-79 and light chain CDRs having the amino acid sequences of SEQ ID NOs: 80-82 or a conservative substitution variant of such amino acid sequence; or heavy chain CDRs having the amino acid sequences of SEQ ID NOs: 83-85 and light chain CDRs having the amino acid sequences of SEQ ID NOs: 86-88 or a conservative substitution variant of such amino acid sequence.

In one aspect of any of the embodiments, described herein is a first antibody, antibody reagent, antigen-binding portion thereof, or CAR that specifically binds an PD1 polypeptide, and can compete for binding of PD1 with a second antibody comprising:

heavy chain CDRs having the amino acid sequences of SEQ ID NOs: 23-25 and light chain CDRs having the amino acid sequences of SEQ ID NOs: 26-28 or a conservative substitution variant of such amino acid sequence; or heavy chain CDRs having the amino acid sequences of SEQ ID NOs: 29-31 and light chain CDRs having the amino acid sequences of SEQ ID NOs: 32-34 or a conservative substitution variant of such amino acid sequence; or heavy chain CDRs having the amino acid sequences of SEQ ID NOs: 35-37 and light chain CDRs having the amino acid sequences of SEQ ID NOs: 38-40 or a conservative substitution variant of such amino acid sequence; or heavy chain CDRs having the amino acid sequences of SEQ ID NOs: 41-43 and light chain CDRs having the amino acid sequences of SEQ ID NOs: 44-46 or a conservative substitution variant of such amino acid sequence; or heavy chain CDRs having the amino acid sequences of SEQ ID NOs: 47-49 and light chain CDRs having the amino acid sequences of SEQ ID NOs: 50-52 or a conservative substitution variant of such amino acid sequence; or heavy chain CDRs having the amino acid sequences of SEQ ID NOs: 53-55 and light chain CDRs having the amino acid sequences of SEQ ID NOs: 56-58 or a conservative substitution variant of such amino acid sequence; or heavy chain CDRs having the amino acid sequences of SEQ ID NOs: 59-61 and light chain CDRs having the amino acid sequences of SEQ ID NOs: 62-64 or a conservative substitution variant of such amino acid sequence; or heavy chain CDRs having the amino acid sequences of SEQ ID NOs: 65-67 and light chain CDRs having the amino acid sequences of SEQ ID NOs: 68-70 or a conservative substitution variant of such amino acid sequence; or heavy chain CDRs having the amino acid sequences of SEQ ID NOs: 71-73 and light chain CDRs having the amino acid sequences of SEQ ID NOs: 74-76 or a conservative substitution variant of such amino acid sequence; or heavy chain CDRs having the amino acid sequences of SEQ ID NOs: 77-79 and light chain CDRs having the amino acid sequences of SEQ ID NOs: 80-82 or a conservative substitution variant of such amino acid sequence; or heavy chain CDRs having the amino acid sequences of SEQ ID NOs: 83-85 and light chain CDRs having the amino acid sequences of SEQ ID NOs: 86-88 or a conservative substitution variant of such amino acid sequence.

In some embodiments of any of the aspects, the antibody, antibody reagent, antigen-binding fragment thereof, or chimaeric antigen receptor (CAR) of claim 5, comprising at least one heavy or light chain complementarity determining region (CDR) selected from the group consisting of:

(a) a heavy chain CDR1 having the amino acid sequence of SEQ ID NO: 23;

(b) a heavy chain CDR2 having the amino acid sequence of SEQ ID NO: 24;

(c) a heavy chain CDR3 having the amino acid sequence of SEQ ID NO: 25;

(d) a light chain CDR1 having the amino acid sequence of SEQ ID NO: 26;

(e) a light chain CDR2 having the amino acid sequence of SEQ ID NO: 27; and (f) a light chain CDR3 having the amino acid sequence of SEQ ID NO: 28; or selected from the group consisting of:

(a) a heavy chain CDR1 having the amino acid sequence of SEQ ID NO: 29;

(b) a heavy chain CDR2 having the amino acid sequence of SEQ ID NO: 30;

(c) a heavy chain CDR3 having the amino acid sequence of SEQ ID NO: 31;

(d) a light chain CDR1 having the amino acid sequence of SEQ ID NO: 32;

(e) a light chain CDR2 having the amino acid sequence of SEQ ID NO: 33; and (f) a light chain CDR3 having the amino acid sequence of SEQ ID NO: 34; or selected from the group consisting of:

(a) a heavy chain CDR1 having the amino acid sequence of SEQ ID NO: 35;

(b) a heavy chain CDR2 having the amino acid sequence of SEQ ID NO: 36;

(c) a heavy chain CDR3 having the amino acid sequence of SEQ ID NO: 37;

(d) a light chain CDR1 having the amino acid sequence of SEQ ID NO: 38;

(e) a light chain CDR2 having the amino acid sequence of SEQ ID NO: 39; and (f) a light chain CDR3 having the amino acid sequence of SEQ ID NO: 40; or selected from the group consisting of:

(a) a heavy chain CDR1 having the amino acid sequence of SEQ ID NO: 41;

(b) a heavy chain CDR2 having the amino acid sequence of SEQ ID NO: 42;

(c) a heavy chain CDR3 having the amino acid sequence of SEQ ID NO: 43;

(d) a light chain CDR1 having the amino acid sequence of SEQ ID NO: 44;

(e) a light chain CDR2 having the amino acid sequence of SEQ ID NO: 45; and (f) a light chain CDR3 having the amino acid sequence of SEQ ID NO: 46; or selected from the group consisting of:

(a) a heavy chain CDR1 having the amino acid sequence of SEQ ID NO: 47;

(b) a heavy chain CDR2 having the amino acid sequence of SEQ ID NO: 48;

(c) a heavy chain CDR3 having the amino acid sequence of SEQ ID NO: 49;

(d) a light chain CDR1 having the amino acid sequence of SEQ ID NO: 50;

(e) a light chain CDR2 having the amino acid sequence of SEQ ID NO: 51; and (f) a light chain CDR3 having the amino acid sequence of SEQ ID NO: 52; or selected from the group consisting of:

(a) a heavy chain CDR1 having the amino acid sequence of SEQ ID NO: 53;

(b) a heavy chain CDR2 having the amino acid sequence of SEQ ID NO: 54;

(c) a heavy chain CDR3 having the amino acid sequence of SEQ ID NO: 55;

(d) a light chain CDR1 having the amino acid sequence of SEQ ID NO: 56;

(e) a light chain CDR2 having the amino acid sequence of SEQ ID NO: 57; and (f) a light chain CDR3 having the amino acid sequence of SEQ ID NO: 58; or selected from the group consisting of:

(a) a heavy chain CDR1 having the amino acid sequence of SEQ ID NO: 59;

(b) a heavy chain CDR2 having the amino acid sequence of SEQ ID NO: 60;

(c) a heavy chain CDR3 having the amino acid sequence of SEQ ID NO: 61;

(d) a light chain CDR1 having the amino acid sequence of SEQ ID NO: 62;

(e) a light chain CDR2 having the amino acid sequence of SEQ ID NO: 63; and (f) a light chain CDR3 having the amino acid sequence of SEQ ID NO: 64; or selected from the group consisting of:

(a) a heavy chain CDR1 having the amino acid sequence of SEQ ID NO: 65;

(b) a heavy chain CDR2 having the amino acid sequence of SEQ ID NO: 66;

(c) a heavy chain CDR3 having the amino acid sequence of SEQ ID NO: 67;

(d) a light chain CDR1 having the amino acid sequence of SEQ ID NO: 68;

(e) a light chain CDR2 having the amino acid sequence of SEQ ID NO: 69; and (f) a light chain CDR3 having the amino acid sequence of SEQ ID NO: 70; or selected from the group consisting of:

(a) a heavy chain CDR1 having the amino acid sequence of SEQ ID NO: 71;

(b) a heavy chain CDR2 having the amino acid sequence of SEQ ID NO: 72;

(c) a heavy chain CDR3 having the amino acid sequence of SEQ ID NO: 73;

(d) a light chain CDR1 having the amino acid sequence of SEQ ID NO: 74;

(e) a light chain CDR2 having the amino acid sequence of SEQ ID NO: 75; and (f) a light chain CDR3 having the amino acid sequence of SEQ ID NO: 76; or selected from the group consisting of:

(a) a heavy chain CDR1 having the amino acid sequence of SEQ ID NO: 77;

(b) a heavy chain CDR2 having the amino acid sequence of SEQ ID NO: 78;

(c) a heavy chain CDR3 having the amino acid sequence of SEQ ID NO: 79;

(d) a light chain CDR1 having the amino acid sequence of SEQ ID NO: 80;

(e) a light chain CDR2 having the amino acid sequence of SEQ ID NO: 81; and (f) a light chain CDR3 having the amino acid sequence of SEQ ID NO: 82; or selected from the group consisting of:

(a) a heavy chain CDR1 having the amino acid sequence of SEQ ID NO: 83;

(b) a heavy chain CDR2 having the amino acid sequence of SEQ ID NO: 84;

(c) a heavy chain CDR3 having the amino acid sequence of SEQ ID NO: 85;

(d) a light chain CDR1 having the amino acid sequence of SEQ ID NO: 86;

(e) a light chain CDR2 having the amino acid sequence of SEQ ID NO: 87; and (f) a light chain CDR3 having the amino acid sequence of SEQ ID NO: 88; or a conservative substitution variant of one or more of (a)-(f).

In some embodiments of any of the aspects, the antibody, antibody reagent, antigen-binding portion thereof, or CAR comprises heavy chain CDRs having the amino acid sequences of SEQ ID NOs: 23-25, or 29-31, or 35-37, or 41-43, or 47-49, or 53-55, or 59-61, or 65-67, or 71-73, or 77-79, or 83- 85, or a conservative substitution variant of such amino acid sequence. In some embodiments of any of the aspects, the antibody, antibody reagent, antigen-binding portion thereof, or CAR comprises light chain CDRs having the amino acid sequences of SEQ ID NOs: 26-28, or 32-34, or 38-40, or 44-46, or 50-52, or 56-58, or 62-64, or 68-70, or 74-76, or 80-82, or 86-88, or a conservative substitution variant of such amino acid sequence. In some embodiments of any of the aspects, the antibody, antibody reagent, antigen-binding portion thereof, or CAR comprises:

heavy chain CDRs having the amino acid sequences of SEQ ID NOs: 23-25 and light chain CDRs having the amino acid sequences of SEQ ID NOs: 26-28 or a conservative substitution variant of such amino acid sequence; or heavy chain CDRs having the amino acid sequences of SEQ ID NOs: 29-31 and light chain CDRs having the amino acid sequences of SEQ ID NOs: 32-34 or a conservative substitution variant of such amino acid sequence; or heavy chain CDRs having the amino acid sequences of SEQ ID NOs: 35-37 and light chain CDRs having the amino acid sequences of SEQ ID NOs: 38-40 or a conservative substitution variant of such amino acid sequence; or heavy chain CDRs having the amino acid sequences of SEQ ID NOs: 41-43 and light chain CDRs having the amino acid sequences of SEQ ID NOs: 44-46 or a conservative substitution variant of such amino acid sequence; or heavy chain CDRs having the amino acid sequences of SEQ ID NOs: 47-49 and light chain CDRs having the amino acid sequences of SEQ ID NOs: 50-52 or a conservative substitution variant of such amino acid sequence; or heavy chain CDRs having the amino acid sequences of SEQ ID NOs: 53-55 and light chain CDRs having the amino acid sequences of SEQ ID NOs: 56-58 or a conservative substitution variant of such amino acid sequence; or heavy chain CDRs having the amino acid sequences of SEQ ID NOs: 59-61 and light chain CDRs having the amino acid sequences of SEQ ID NOs: 62-64 or a conservative substitution variant of such amino acid sequence; or heavy chain CDRs having the amino acid sequences of SEQ ID NOs: 65-67 and light chain CDRs having the amino acid sequences of SEQ ID NOs: 68-70 or a conservative substitution variant of such amino acid sequence; or heavy chain CDRs having the amino acid sequences of SEQ ID NOs: 71-73 and light chain CDRs having the amino acid sequences of SEQ ID NOs: 74-76 or a conservative substitution variant of such amino acid sequence; or heavy chain CDRs having the amino acid sequences of SEQ ID NOs: 77-79 and light chain CDRs having the amino acid sequences of SEQ ID NOs: 80-82 or a conservative substitution variant of such amino acid sequence; or heavy chain CDRs having the amino acid sequences of SEQ ID NOs: 83-85 and light chain CDRs having the amino acid sequences of SEQ ID NOs: 86-88 or a conservative substitution variant of such amino acid sequence.

In some embodiments of any of the aspects, the antibody, antibody reagent, antigen-binding portion thereof, or CAR comprising the heavy chain sequence of any of SEQ ID NOs: 1, 3, 5, 7, 9, 11, 13, 15, 17, 19 or 21. In some embodiments of any of the aspects, the antibody, antibody reagent, antigen-binding portion thereof, or CAR comprises the light chain sequence of any of SEQ ID NOs: 2, 4, 6, 8, 10, 12, 14, 16, 18, 20, or 22. In some embodiments of any of the aspects, the antibody, antibody reagent, antigen-binding portion thereof, or CAR comprises:

the heavy chain sequence of SEQ ID NO: 1 and the light chain sequence of SEQ ID NO: 2; or the heavy chain sequence of SEQ ID NO: 3 and the light chain sequence of SEQ ID NO: 4; or the heavy chain sequence of SEQ ID NO: 5 and the light chain sequence of SEQ ID NO: 6; or the heavy chain sequence of SEQ ID NO: 7 and the light chain sequence of SEQ ID NO: 8; or the heavy chain sequence of SEQ ID NO: 9 and the light chain sequence of SEQ ID NO: 10; or the heavy chain sequence of SEQ ID NO: 11 and the light chain sequence of SEQ ID NO: 12; or the heavy chain sequence of SEQ ID NO: 13 and the light chain sequence of SEQ ID NO: 14; or the heavy chain sequence of SEQ ID NO: 15 and the light chain sequence of SEQ ID NO: 16; or the heavy chain sequence of SEQ ID NO: 17 and the light chain sequence of SEQ ID NO: 18; or the heavy chain sequence of SEQ ID NO: 19 and the light chain sequence of SEQ ID NO: 20; or the heavy chain sequence of SEQ ID NO: 21 and the light chain sequence of SEQ ID NO: 22.

In some embodiments of any of the aspects, the antibody, antibody reagent, antigen-binding portion thereof, or CAR further comprises a conservative substitution in a sequence not comprised by a CDR. In some embodiments of any of the aspects, the antibody, antibody reagent, antigen-binding portion thereof, or CAR is fully human or fully humanized. In some embodiments of any of the aspects, the antibody, antibody reagent, antigen-binding portion thereof, or CAR is fully humanized except for the CDR sequences. In some embodiments of any of the aspects, the antibody, antibody reagent, antigen-binding portion thereof, or CAR is selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

In one aspect of any of the embodiments, described herein is a composition comprising the antibody, antibody reagent, antigen-binding portion thereof, or CAR as described herein, and a chemotherapeutic agent. In some embodiments of any of the aspects, the antibody, antibody reagent, or antigen-binding portion thereof is conjugated to the chemotherapeutic agent.

In one aspect of any of the embodiments, described herein is a nucleic acid sequence encoding the antibody, antibody reagent, antigen-binding fragment thereof, or CAR as described herein. In one aspect of any of the embodiments, described herein is a cell comprising the antibody, antibody reagent, antigen-binding fragment thereof, or CAR as described herein or a nucleic acid sequence of encoding the antibody, antibody reagent, antigen-binding fragment thereof, or CAR.

In one aspect of any of the embodiments, described herein is a pharmaceutical composition comprising the antibody, antibody reagent, antigen-binding fragment thereof, or CAR as described herein, optionally with a chemotherapeutic agent, or a cell comprising the antibody, antibody reagent, antigen-binding fragment thereof, or CAR as described herein, and a pharmaceutically acceptable carrier.

In one aspect of any of the embodiments, described herein is a solid support comprising the antibody, antibody reagent, antigen-binding fragment thereof, or CAR as described herein. In some embodiments of any of the aspects, the antibody, antibody reagent or antigen-binding fragment thereof is detectably labeled. In some embodiments of any of the aspects, the solid support comprises a particle, a bead, a polymer, or a substrate.

In one aspect of any of the embodiments, described herein is a kit comprising at least a first antibody, antibody reagent, antigen-binding fragment thereof, or CAR as described herein.

In one aspect of any of the embodiments, described herein is a kit for the detection of PD1 polypeptide in a sample, the kit comprising at least a first antibody, antibody reagent, antigen-binding fragment thereof, or CAR as described herein, immobilized on a solid support and comprising a detectable label.

In one aspect of any of the embodiments, described herein is a molecular complex comprising at least one antibody, antibody reagent, antigen-binding fragment thereof, or CAR as described herein bound to an PD1 polypeptide.

In one aspect of any of the embodiments, described herein is a method of treating cancer in a subject in need thereof, the method comprising administering the antibody, antibody reagent, antigen-binding fragment thereof, or CAR as described herein; or a composition comprising the antibody, antibody reagent, antigen-binding fragment thereof, or CAR as described herein (optionally with a chemotherapeutic agent); or a cell comprising the antibody, antibody reagent, antigen-binding fragment thereof, or CAR as described herein, to the subject. In some embodiments of any of the aspects, a therapeutically effective amount of the antibody, antibody reagent, antigen-binding fragment thereof, or CAR is administered to the subject. In some embodiments of any of the aspects, the cancer is selected from the group consisting of non-small cell lung cancer; melanoma; metastatic melanoma; renal cell carcinoma; squamous cell carcinoma of the head and neck; Hodgkin lymphoma; classical Hodgkin lymphoma; and urothelial carcinoma.

BRIEF DESCRIPTION OF THE DRAWINGS

FIG. 1 depicts the sequence alignment of anti-PD1 antibody heavy chains (SEQ ID NOS 91-123, respectively, in order of appearance). The sequence of the original anti-PD1 antibody, 17D8, is shown at the top for comparison; the sequences of novel anti-PD1 antibodies (319-8-x, 319-9-x) are shown below 17D8 sequence. "." represents sequence identity; "-" represents gap in sequence alignment; at positions where new antibodies differ from 17D8, the residues in new antibodies are shown. The positions of CDR H1, 2, and 3 are delineated on the sequences; the total number of residues in variable region is shown to the right of the sequences.

Figure 1:
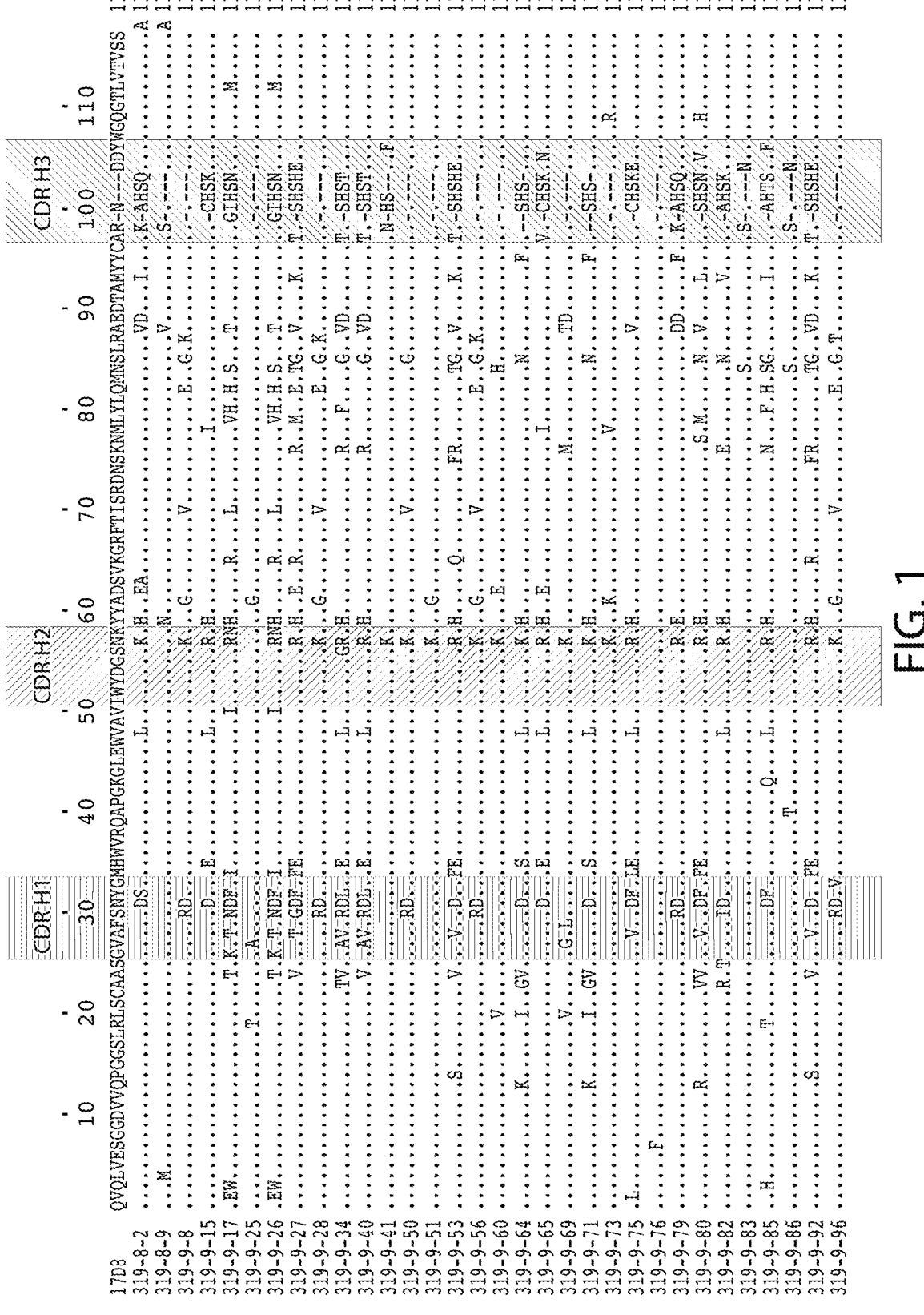
Figure 2:
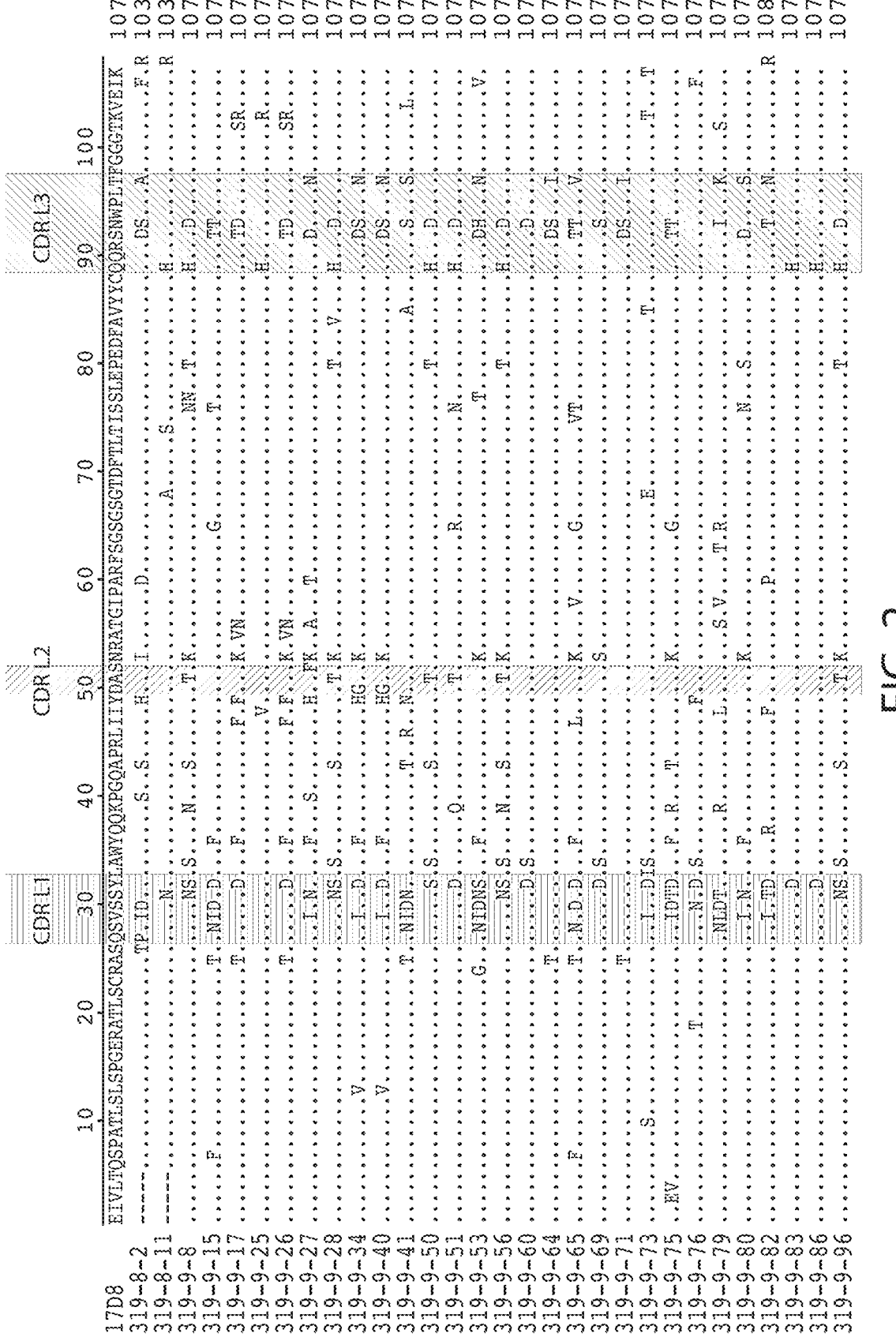

FIG. 2 depicts the sequence alignment of anti-PD1 antibody light chains (SEQ ID NOS 124-154, respectively, in order of appearance). The sequence of the original anti-PD1 antibody, 17D8, is shown at the top for comparison; the sequences of novel anti-PD1 antibodies (319-8-x, 319-9-x) are shown below 17D8 sequence. "." represents sequence identity; "-" represents gap in sequence alignment; at positions where new antibodies differ from 17D8, the residues in new antibodies are shown. The positions of CDR L1, 2, and 3 are delineated on the sequences; the total number of residues in variable region is shown to the right of the sequences.

Figures 1, 3:
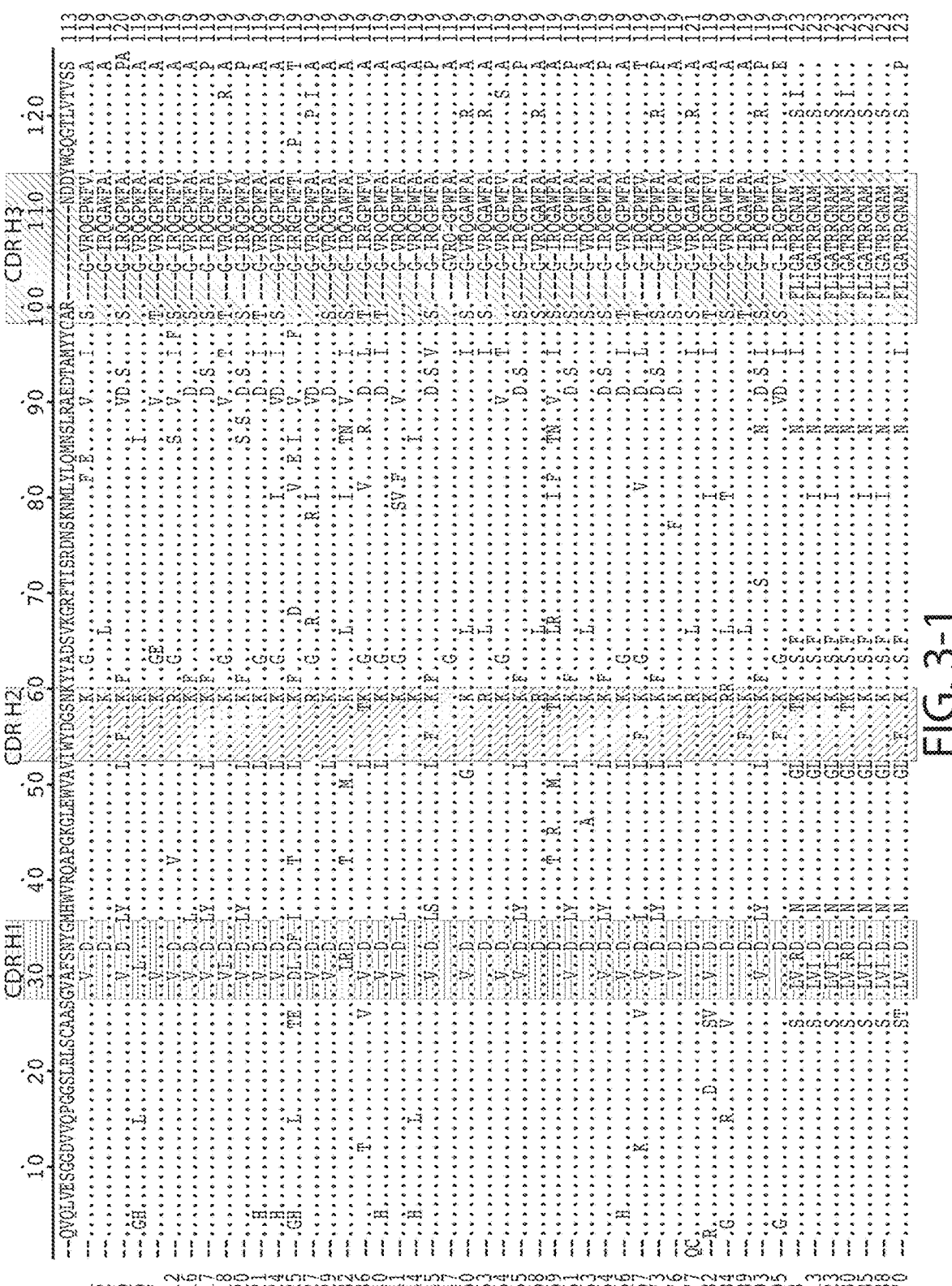
Figures 2, 3:
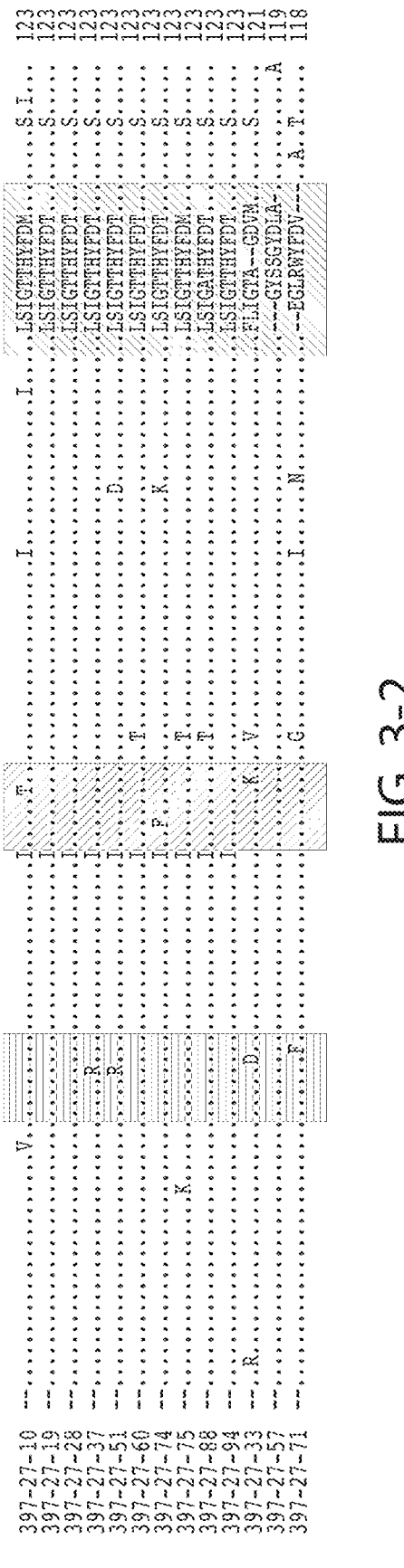

FIG. 3 depicts the sequence alignment of anti-PD1 antibody heavy chains (SEQ ID NOS 155-216, respectively, in order of appearance). The sequence of the original anti-PD1 antibody, 17D8, is shown at the top for comparison; the sequences of novel anti-PD1 antibodies (397-27-x) are shown below 17D8 sequence. "." represents sequence identity; "-" represents gap in sequence alignment; at positions where new antibodies differ from 17D8, the residues in new antibodies are shown. The positions of CDR H1, 2, and 3 are delineated on the sequences; the total number of residues in variable region is shown to the right of the sequences.

Figure 4:
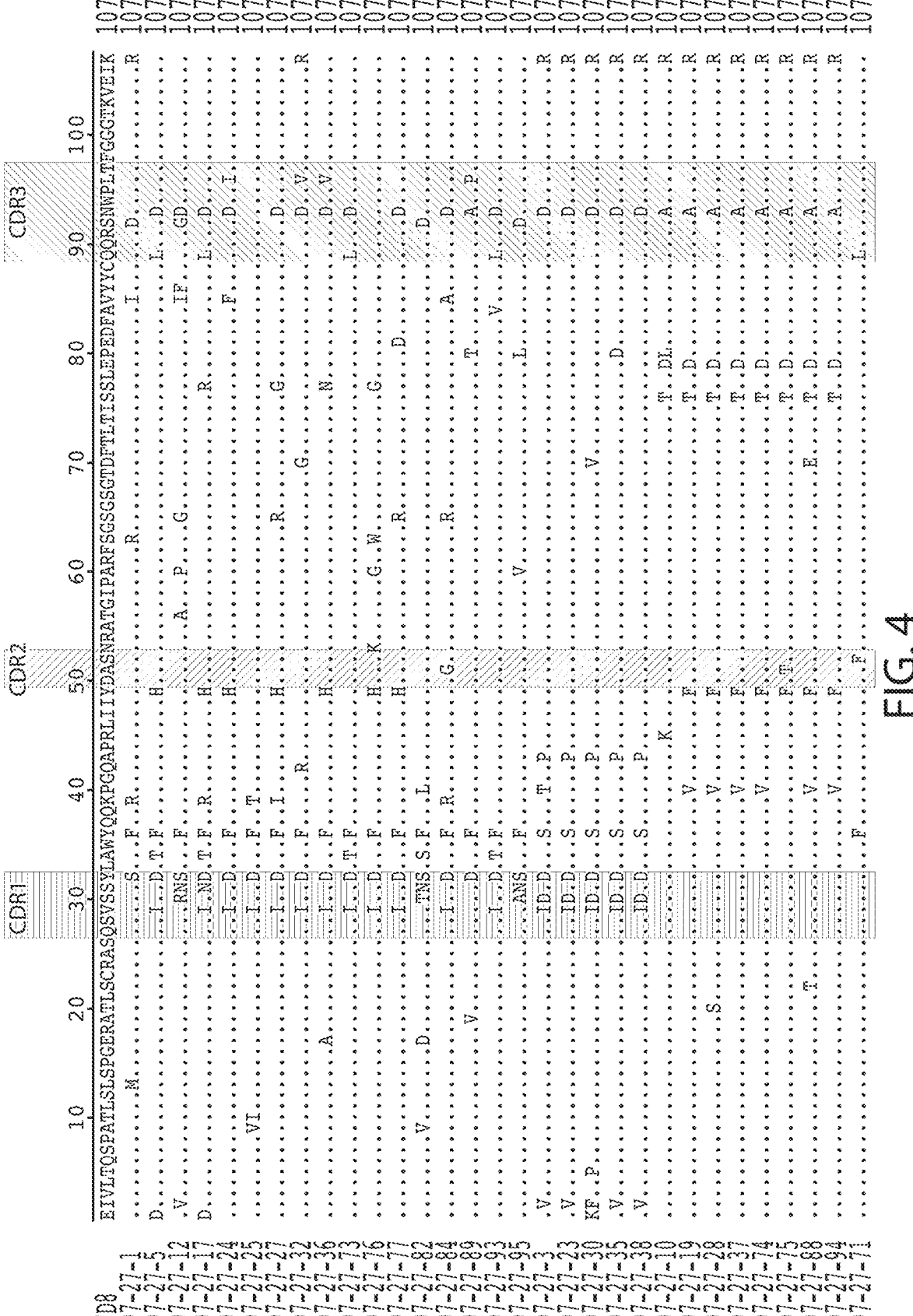

FIG. 4 depicts the sequence alignment of anti-PD1 antibody light chains (SEQ ID NOS 217-248, respectively, in order of appearance). The sequence of the original anti-PD1 antibody, 17D8, is shown at the top for comparison; the sequences of novel anti-PD1 antibodies (397-27-x) are shown below 17D8 sequence. "." represents sequence identity; "-" represents gap in sequence alignment; at positions where new antibodies differ from 17D8, the residues in new antibodies are shown. The positions of CDR L1, 2, and 3 are delineated on the sequences; the total number of residues in variable region is shown to the right of the sequences.

Figure 5:
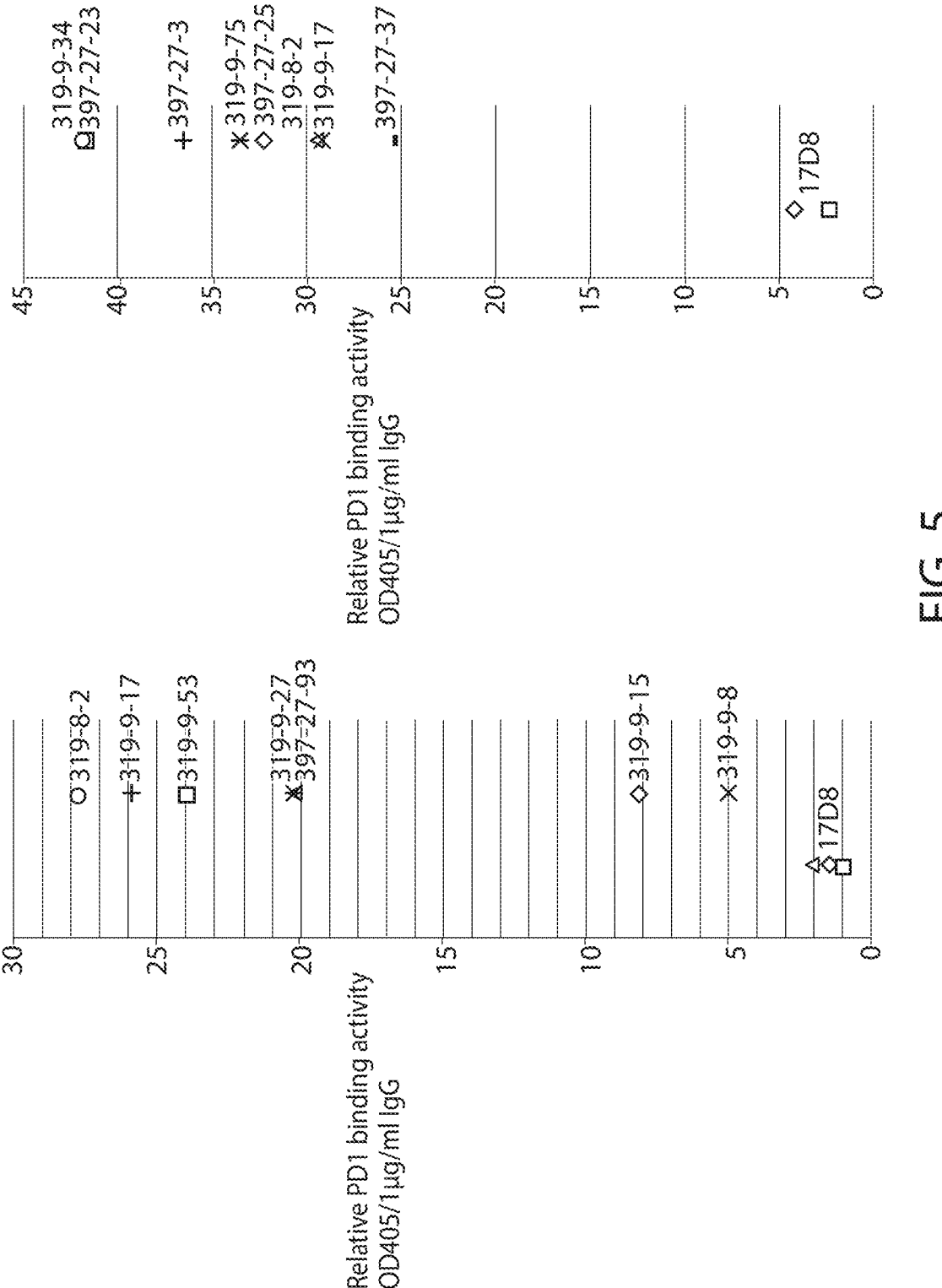

FIG. 5 depicts plots comparing the binding activity of new anti-PD1 antibodies (319-8-2, 319-9-x, 397-27-x) with the original anti-PD1 antibody (17D8). PD1 binding activity was measured with ELISA assay and represented by OD405 value. The OD405 value for each antibody was normalized to antibody concentration. The y-axis shows the OD405 value for antibody at 1 mg/ml. A subset of the new antibodies shown in FIGS. 1-4 has been analyzed in this assay, and most of the new antibodies exhibited higher PD-1 binding activity than the original anti-PD1 antibody.

Figure 6:
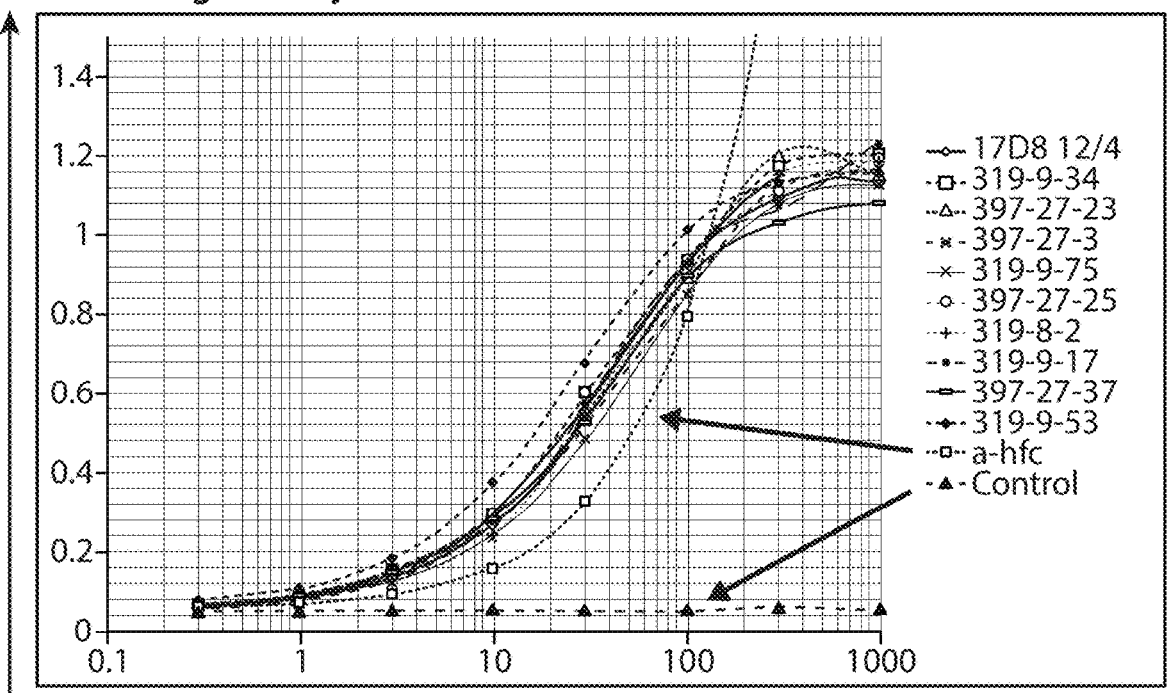
Figure 1:
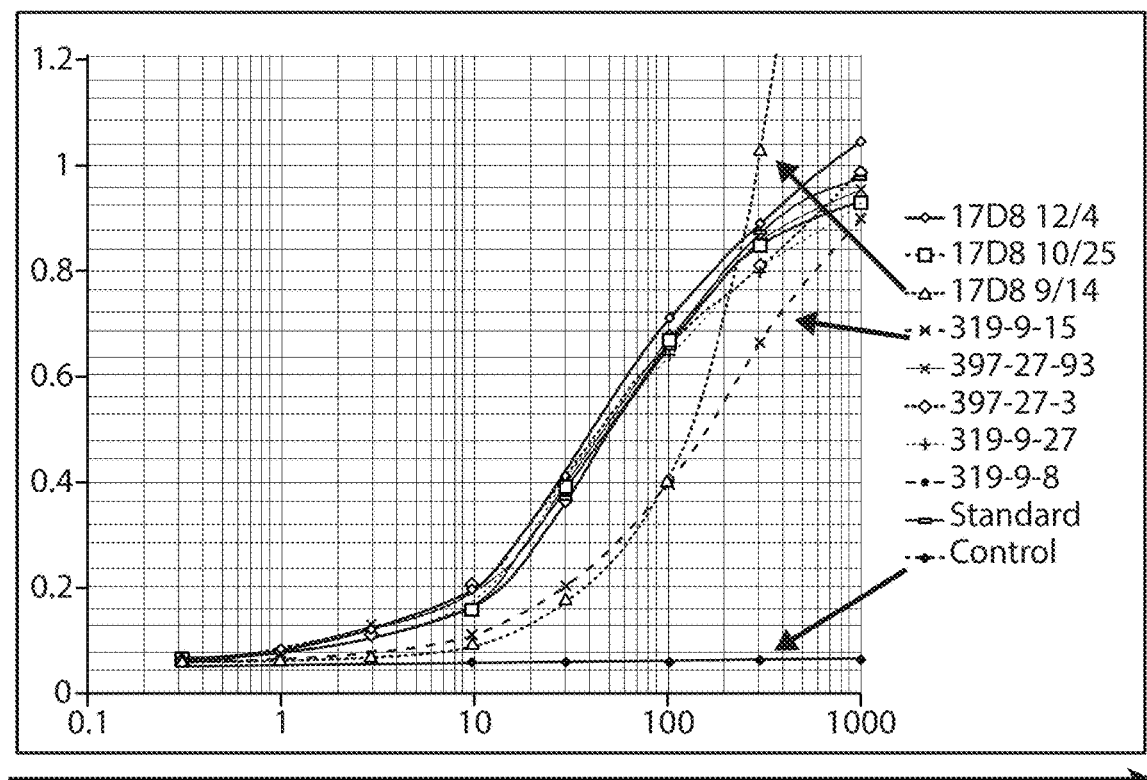
Figure 6:
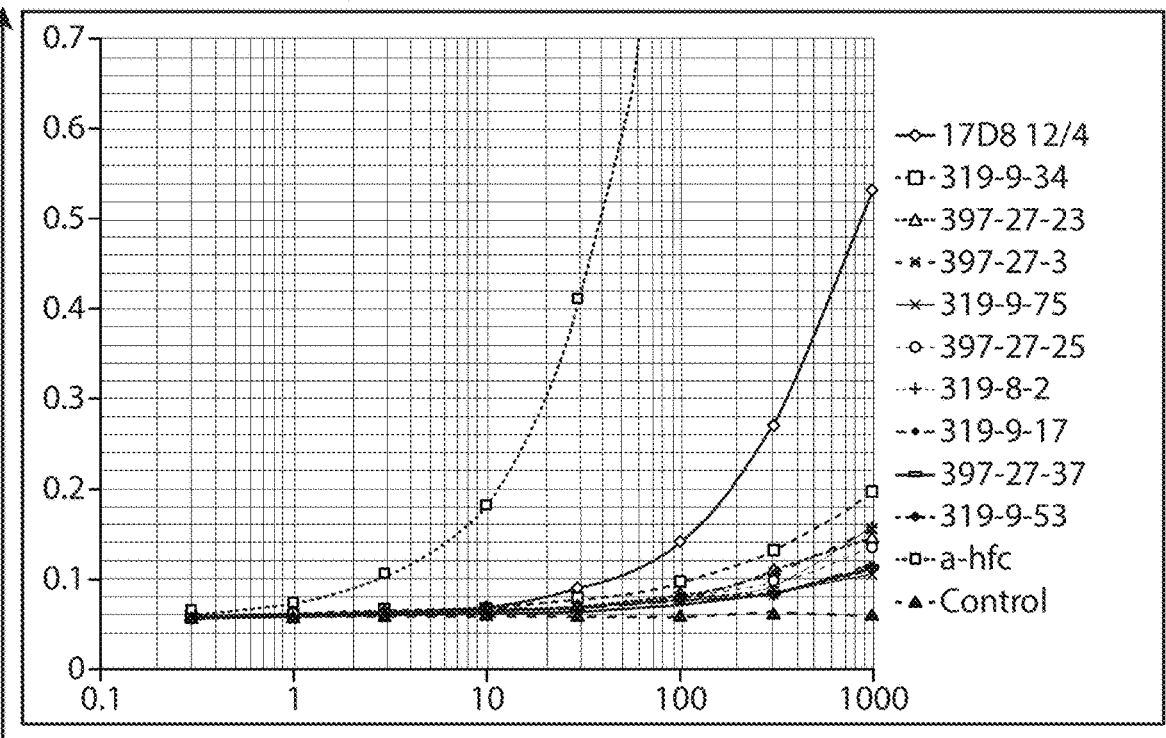
Figure 2:
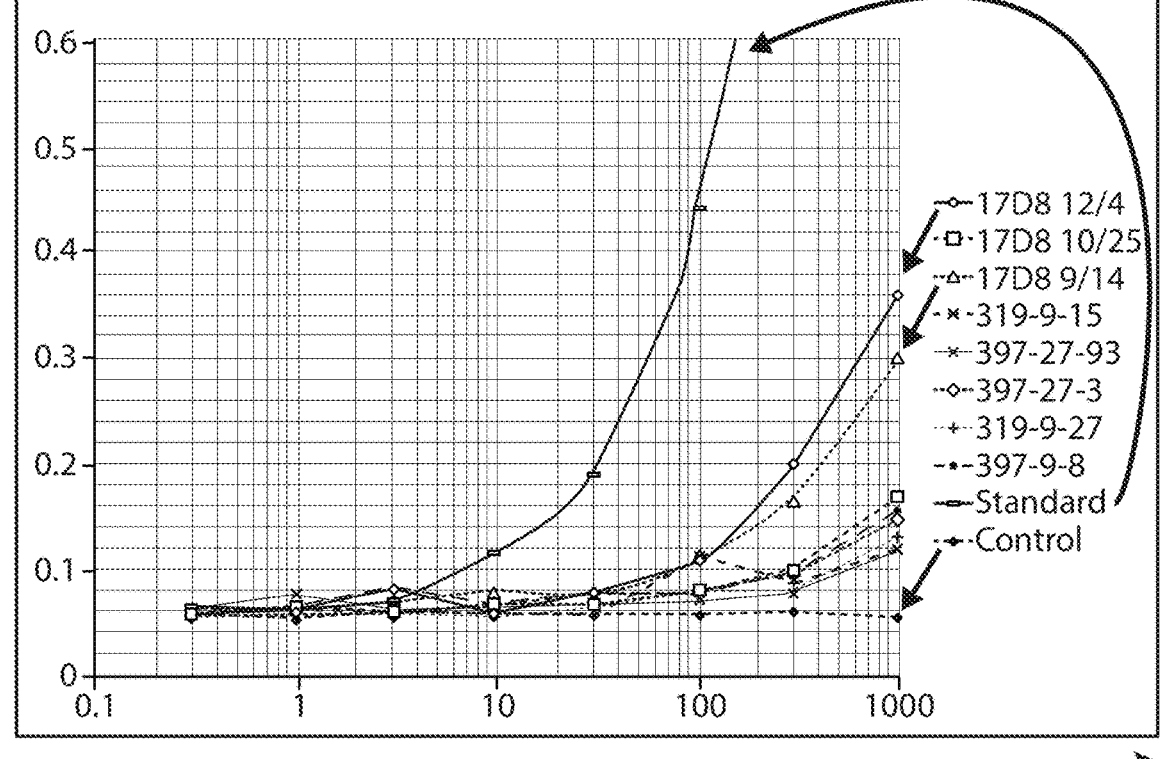
Figure 6:
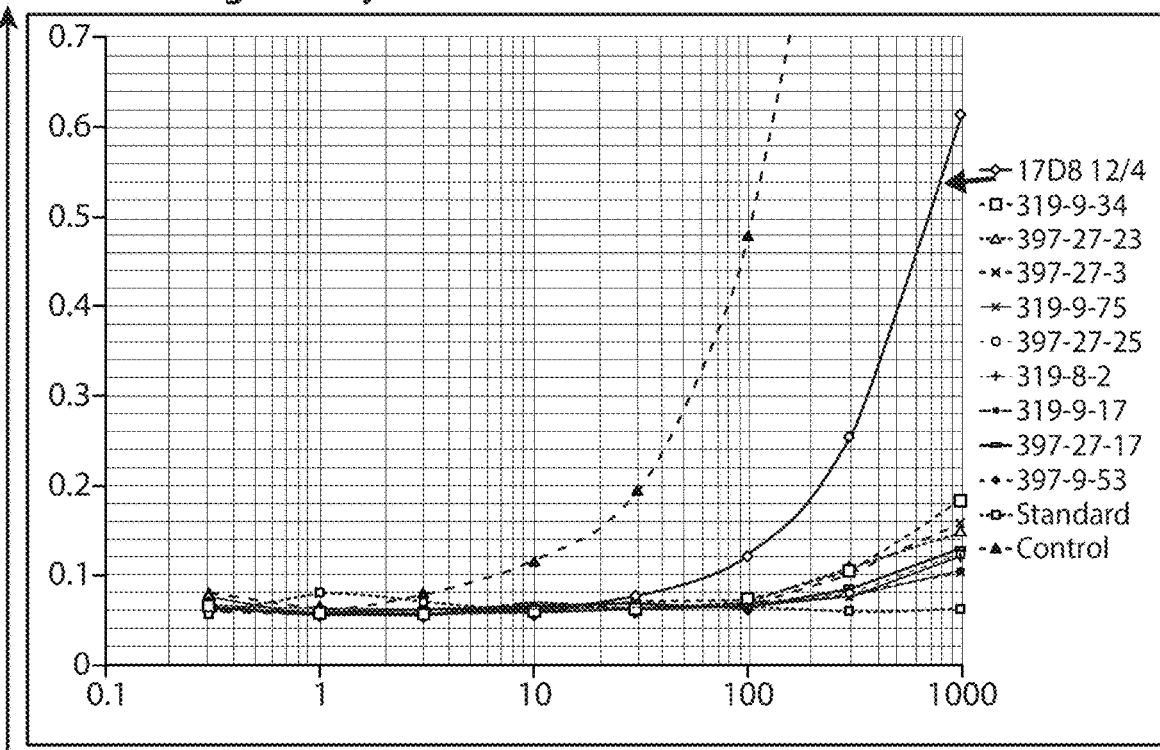
Figure 3:
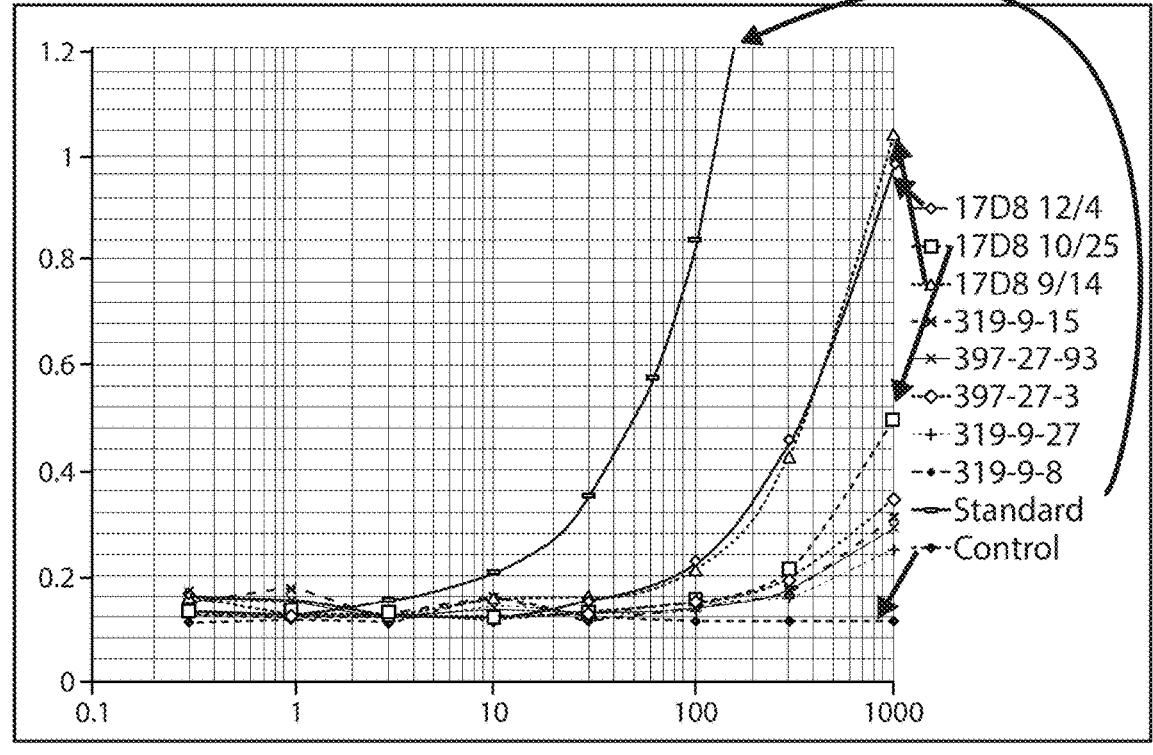

FIG. 6 depicts the results of experiments to compare the binding specificity of new anti-PD1 antibody (319-8-2, 319-9-x, 397-27-x) with the original anti-PD1 antibody (17D8). In this experiment, the binding activity of each antibody to PD1, CTLA4 and CD28 was measured with ELISA assay. PD1, CTLA4 and CD28 are homologous to one another and belong to the CD28 family of T cell regulatory receptors. The plots show titration curves of each antibody in the ELISA assay. The x-axis represents relative antibody concentration, based on dilution factors; the y-axis shows OD405 value, which correlates with antibody binding activity. Based on this experiment, all the new antibodies exhibited lower cross reactivity toward CTLA4 and CD28.

DETAILED DESCRIPTION

Described herein are antibodies, antibody reagents, antigen-binding fragments thereof, or chimaeric antigen receptors (CARs) that specifically bind a PD1 polypeptide. Such antibodies, antigen binding portions thereof, etc., can permit, e.g., the diagnosis, prognosis, and/or treatment of cancer. In some embodiments, the technology described herein relates to chimeric antigen receptors (CARs) and CAR-T therapy for cancer. In some embodiments, the technology described herein relates to monoclonal antibody therapy for cancer. In some embodiments, the technology described herein relates to antibody-drug conjugates for the treatment of cancer or cancer.

As used herein, "PD1" or "programmed death 1" refers to a cell surface receptor that suppresses T cell inflammatory responses. PD1 serves as an immune system checkpoint and prevents against development of autoimmune diseases. Anti-PD1 therapies are used in cancer to stimulate the immune system. The sequences of PD1 expression products are known for a number of species, e.g., human PD1 (NCBI Gene ID No: 5133) mRNA (NCBI Ref Seq: NM_005018.2) and polypeptide (NCBI Ref Seq: NP_005009.2).

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. The exact boundaries of these CDRs have been defined differently according to different systems. CDRs may be defined according to the Kabat system (see Kabat, E. A. et al., 1991, "Sequences of Proteins of Immunological Interest", 5th edit., NIH Publication no. 91-3242, U.S. Department of Health and Human Services). Other systems may be used to define CDRs, which as the system devised by Chothia et al (see Chothia, C. & Lesk, A. M., 1987, "Canonical structures for the hypervariable regions of immunoglobulins", J. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR. The methods and compositions used herein may utilize CDRs defined according to any of these systems. The CDR's identified herein, e.g., in Table 1 were identified by the IMGT system (see, e.g. FIGS. 1-4).

The term "antigen-binding portion" of an antibody refers to one or more portions of an antibody as described herein, said portions) still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CH1 domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion consisting of a VH domain or of VH, CH1, CH2, DH3, or VH, CH2, CH3 (dAbs, or single domain antibodies, comprising only $V_L$ domains have also been shown to specifically bind to target epitopes). Although the two domains of the Fv portion, namely VL and VH, are encoded by separate genes, they may further be linked to one another using a synthetic linker, e.g., a poly-G4S amino acid sequence ('G4S' disclosed as SEQ ID NO: 90), and recombinant methods, making it possible to prepare them as a single protein chain in which the VL and VH regions combine in order to form monovalent molecules (known as single chain Fv (ScFv)). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

Furthermore, an antibody, antigen-binding portion thereof, or CAR as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule and the use of a cystein residue, a marker peptide and a C-terminal polyhistidinyl, e.g., hexahistidinyl tag ('hexahistidinyl tag' disclosed as SEQ ID NO: 89) in order to produce bivalent and biotinylated scFv molecules.

In some embodiments, the antibody, antibody reagent, antigen-binding portion thereof, or CAR described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

In some embodiments, the antibody or antigen-binding portion thereof is a fully human antibody. In some embodiments, the antibody, antigen-binding portion thereof, is a humanized antibody or antibody reagent. In some embodiments, the antibody, antigen-binding portion thereof, is a fully humanized antibody or antibody reagent. In some embodiments, the antibody or antigen-binding portion thereof, is a chimeric antibody or antibody reagent. In some embodiments, the antibody, antigen-binding portion thereof, is a recombinant polypeptide. In some embodiments, the CAR comprises an extracellular domain that binds PD1, wherein the extracellular domain comprises a humanized or chimeric antibody or antigen-binding portion thereof.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both.

Preferably, mutagenesis leads to an affinity to the target which is greater, and/or an affinity to non-target structures which is smaller than that of the parent antibody. Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. In some embodiments, it is possible to make one or more conservative amino acid substitutions of CDR residues without appreciably affecting the binding affinity of the resulting humanized immunoglobulin or human antibody variant. In some embodiments, substitutions of CDR regions can enhance binding affinity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin). The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species, antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody, antigen-binding portion thereof, or CAR as described herein. Such functional activities include binding to cancer cells and/or anti-cancer activity. Additionally, a polypeptide having functional activity means the polypeptide exhibits activity similar, but not necessarily identical to, an activity of a reference antibody, antigen-binding portion thereof, or CAR as described herein, including mature forms, as measured in a particular assay, such as, for example, a biological assay, with or without dose dependency. In the case where dose dependency does exist, it need not be identical to that of the reference antibody, antigen-binding portion thereof, or CAR, but rather substantially similar to the dose-dependence in a given activity as compared to the reference antibody, antigen-binding portion thereof, or CAR as described herein (i.e., the candidate polypeptide will exhibit greater activity, or not more than about 25-fold less, about 10-fold less, or about 3-fold less activity relative to the antibodies, antigen-binding portions, and/or CARs described herein).

In some embodiments, the antibody reagents (e.g., antibodies or CARs) described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

In some embodiments, the antibody, antibody reagent, antigen-binding portion thereof, and/or CAR is an isolated polypeptide. In some embodiments, the antibody, antibody reagent, antigen-binding portion thereof, and/or CAR is a purified polypeptide. In some embodiments, the antibody, antibody reagent, antigen-binding portion thereof, and/or CAR is an engineered polypeptide.

In one aspect of any of the embodiments, described herein is an antibody, antigen-binding fragment thereof, antigen reagent or chimaeric antigen receptor (CAR), that specifically binds a PD1 polypeptide. In some embodiments of any of the aspects, the antibody, antigen-binding fragment thereof, antigen reagent or CAR comprises at least one CDR, all six CDRs, the light chain, the heavy chain, or the light and heavy chain of an antibody depicted in FIGS. 1-4. In some embodiments of any of the aspects, the antibody, antigen-binding fragment thereof, antigen reagent or CAR comprises at least one heavy or light chain complementarity determining region (CDR) selected from the group consisting of:

(a) a heavy chain CDR1 having the amino acid sequence of SEQ ID NO: 23;
(b) a heavy chain CDR2 having the amino acid sequence of SEQ ID NO: 24;
(c) a heavy chain CDR3 having the amino acid sequence of SEQ ID NO: 25;
(d) a light chain CDR1 having the amino acid sequence of SEQ ID NO: 26;
(e) a light chain CDR2 having the amino acid sequence of SEQ ID NO: 27; and
(f) a light chain CDR3 having the amino acid sequence of SEQ ID NO: 28; or selected from the group consisting of:

(a) a heavy chain CDR1 having the amino acid sequence of SEQ ID NO: 29;

(b) a heavy chain CDR2 having the amino acid sequence of SEQ ID NO: 30;

(c) a heavy chain CDR3 having the amino acid sequence of SEQ ID NO: 31;

(d) a light chain CDR1 having the amino acid sequence of SEQ ID NO: 32;

(e) a light chain CDR2 having the amino acid sequence of SEQ ID NO: 33; and (f) a light chain CDR3 having the amino acid sequence of SEQ ID NO: 34; or selected from the group consisting of:

(a) a heavy chain CDR1 having the amino acid sequence of SEQ ID NO: 35;

(b) a heavy chain CDR2 having the amino acid sequence of SEQ ID NO: 36;

(c) a heavy chain CDR3 having the amino acid sequence of SEQ ID NO: 37;

(d) a light chain CDR1 having the amino acid sequence of SEQ ID NO: 38;

(e) a light chain CDR2 having the amino acid sequence of SEQ ID NO: 39; and (f) a light chain CDR3 having the amino acid sequence of SEQ ID NO: 40; or selected from the group consisting of:

(a) a heavy chain CDR1 having the amino acid sequence of SEQ ID NO: 41;

(b) a heavy chain CDR2 having the amino acid sequence of SEQ ID NO: 42;

(c) a heavy chain CDR3 having the amino acid sequence of SEQ ID NO: 43;

(d) a light chain CDR1 having the amino acid sequence of SEQ ID NO: 44;

(e) a light chain CDR2 having the amino acid sequence of SEQ ID NO: 45; and (f) a light chain CDR3 having the amino acid sequence of SEQ ID NO: 46; or selected from the group consisting of:

(a) a heavy chain CDR1 having the amino acid sequence of SEQ ID NO: 47;

(b) a heavy chain CDR2 having the amino acid sequence of SEQ ID NO: 48;

(c) a heavy chain CDR3 having the amino acid sequence of SEQ ID NO: 49;

(d) a light chain CDR1 having the amino acid sequence of SEQ ID NO: 50;

(e) a light chain CDR2 having the amino acid sequence of SEQ ID NO: 51; and (f) a light chain CDR3 having the amino acid sequence of SEQ ID NO: 52; or selected from the group consisting of:

(a) a heavy chain CDR1 having the amino acid sequence of SEQ ID NO: 53;

(b) a heavy chain CDR2 having the amino acid sequence of SEQ ID NO: 54;

(c) a heavy chain CDR3 having the amino acid sequence of SEQ ID NO: 55;

(d) a light chain CDR1 having the amino acid sequence of SEQ ID NO: 56;

(e) a light chain CDR2 having the amino acid sequence of SEQ ID NO: 57; and (f) a light chain CDR3 having the amino acid sequence of SEQ ID NO: 58; or selected from the group consisting of:

(a) a heavy chain CDR1 having the amino acid sequence of SEQ ID NO: 59;

(b) a heavy chain CDR2 having the amino acid sequence of SEQ ID NO: 60;

(c) a heavy chain CDR3 having the amino acid sequence of SEQ ID NO: 61;

(d) a light chain CDR1 having the amino acid sequence of SEQ ID NO: 62;

(e) a light chain CDR2 having the amino acid sequence of SEQ ID NO: 63; and (f) a light chain CDR3 having the amino acid sequence of SEQ ID NO: 64; or selected from the group consisting of:

(a) a heavy chain CDR1 having the amino acid sequence of SEQ ID NO: 65;

(b) a heavy chain CDR2 having the amino acid sequence of SEQ ID NO: 66;

(c) a heavy chain CDR3 having the amino acid sequence of SEQ ID NO: 67;

(d) a light chain CDR1 having the amino acid sequence of SEQ ID NO: 68;

(e) a light chain CDR2 having the amino acid sequence of SEQ ID NO: 69; and (f) a light chain CDR3 having the amino acid sequence of SEQ ID NO: 70; or selected from the group consisting of:

(a) a heavy chain CDR1 having the amino acid sequence of SEQ ID NO: 71;

(b) a heavy chain CDR2 having the amino acid sequence of SEQ ID NO: 72;

(c) a heavy chain CDR3 having the amino acid sequence of SEQ ID NO: 73;

(d) a light chain CDR1 having the amino acid sequence of SEQ ID NO: 74;

(e) a light chain CDR2 having the amino acid sequence of SEQ ID NO: 75; and (f) a light chain CDR3 having the amino acid sequence of SEQ ID NO: 76; or selected from the group consisting of:

(a) a heavy chain CDR1 having the amino acid sequence of SEQ ID NO: 77;

(b) a heavy chain CDR2 having the amino acid sequence of SEQ ID NO: 78;

(c) a heavy chain CDR3 having the amino acid sequence of SEQ ID NO: 79;

(d) a light chain CDR1 having the amino acid sequence of SEQ ID NO: 80;

(e) a light chain CDR2 having the amino acid sequence of SEQ ID NO: 81; and (f) a light chain CDR3 having the amino acid sequence of SEQ ID NO: 82; or selected from the group consisting of:

(a) a heavy chain CDR1 having the amino acid sequence of SEQ ID NO: 83;

(b) a heavy chain CDR2 having the amino acid sequence of SEQ ID NO: 84;

(c) a heavy chain CDR3 having the amino acid sequence of SEQ ID NO: 85;

(d) a light chain CDR1 having the amino acid sequence of SEQ ID NO: 86;

(e) a light chain CDR2 having the amino acid sequence of SEQ ID NO: 87; and (f) a light chain CDR3 having the amino acid sequence of SEQ ID NO: 88; or a conservative substitution variant of one or more of (a)-(f).

In some embodiments of any of the aspects, the antibody, antibody reagent, antigen-binding portion thereof, or CAR comprises heavy chain CDRs having the amino acid sequences of SEQ ID NOs: 23-25, or 29-31, or 35-37, or 41-43, or 47-49, or 53-55, or 59-61, or 65-67, or 71-73, or 77-79, or 83- 85, or a conservative substitution variant of such amino acid sequence. In some embodiments of any of the aspects, the antibody, antibody reagent, antigen-binding portion thereof, or CAR comprises light chain CDRs having the amino acid sequences of SEQ ID NOs: 26-28, or 32-34, or 38-40, or 44-46, or 50-52, or 56-58, or 62-64, or 68-70, or 74-76, or 80-82, or 86-88, or a conservative substitution variant of such amino acid sequence. In some embodiments of any of the aspects, the antibody, antibody reagent, anti-gen-binding portion thereof, or CAR comprises:

heavy chain CDRs having the amino acid sequences of SEQ ID NOs: 23-25 and light chain CDRs having the amino acid sequences of SEQ ID NOs: 26-28 or a conservative substitution variant of such amino acid sequence; or heavy chain CDRs having the amino acid sequences of SEQ ID NOs: 29-31 and light chain CDRs having the amino acid sequences of SEQ ID NOs: 32-34 or a conservative substitution variant of such amino acid sequence; or heavy chain CDRs having the amino acid sequences of SEQ ID NOs: 35-37 and light chain CDRs having the amino acid sequences of SEQ ID NOs: 38-40 or a conservative substitution variant of such amino acid sequence; or heavy chain CDRs having the amino acid sequences of SEQ ID NOs: 41-43 and light chain CDRs having the amino acid sequences of SEQ ID NOs: 44-46 or a conservative substitution variant of such amino acid sequence; or heavy chain CDRs having the amino acid sequences of SEQ ID NOs: 47-49 and light chain CDRs having the amino acid sequences of SEQ ID NOs: 50-52 or a conservative substitution variant of such amino acid sequence; or heavy chain CDRs having the amino acid sequences of SEQ ID NOs: 53-55 and light chain CDRs having the amino acid sequences of SEQ ID NOs: 56-58 or a conservative substitution variant of such amino acid sequence; or heavy chain CDRs having the amino acid sequences of SEQ ID NOs: 59-61 and light chain CDRs having the amino acid sequences of SEQ ID NOs: 62-64 or a conservative substitution variant of such amino acid sequence; or heavy chain CDRs having the amino acid sequences of SEQ ID NOs: 65-67 and light chain CDRs having the amino acid sequences of SEQ ID NOs: 68-70 or a conservative substitution variant of such amino acid sequence; or heavy chain CDRs having the amino acid sequences of SEQ ID NOs: 71-73 and light chain CDRs having the amino acid sequences of SEQ ID NOs: 74-76 or a conservative substitution variant of such amino acid sequence; or heavy chain CDRs having the amino acid sequences of SEQ ID NOs: 77-79 and light chain CDRs having the amino acid sequences of SEQ ID NOs: 80-82 or a conservative substitution variant of such amino acid sequence; or heavy chain CDRs having the amino acid sequences of SEQ ID NOs: 83-85 and light chain CDRs having the amino acid sequences of SEQ ID NOs: 86-88 or a conservative substitution variant of such amino acid sequence.

In one aspect of any of the embodiments, described herein is an antibody, antibody reagent, antigen-binding portion thereof, or CAR that specifically binds an PD1 polypeptide, and can compete for binding of PD1 with a second antibody comprising:

heavy chain CDRs having the amino acid sequences of SEQ ID NOs: 23-25 and light chain CDRs having the amino acid sequences of SEQ ID NOs: 26-28 or a conservative substitution variant of such amino acid sequence; or heavy chain CDRs having the amino acid sequences of SEQ ID NOs: 29-31 and light chain CDRs having the amino acid sequences of SEQ ID NOs: 32-34 or a conservative substitution variant of such amino acid sequence; or heavy chain CDRs having the amino acid sequences of SEQ ID NOs: 35-37 and light chain CDRs having the amino acid sequences of SEQ ID NOs: 38-40 or a conservative substitution variant of such amino acid sequence; or heavy chain CDRs having the amino acid sequences of SEQ ID NOs: 41-43 and light chain CDRs having the amino acid sequences of SEQ ID NOs: 44-46 or a conservative substitution variant of such amino acid sequence; or heavy chain CDRs having the amino acid sequences of SEQ ID NOs: 47-49 and light chain CDRs having the amino acid sequences of SEQ ID NOs: 50-52 or a conservative substitution variant of such amino acid sequence; or heavy chain CDRs having the amino acid sequences of SEQ ID NOs: 53-55 and light chain CDRs having the amino acid sequences of SEQ ID NOs: 56-58 or a conservative substitution variant of such amino acid sequence; or heavy chain CDRs having the amino acid sequences of SEQ ID NOs: 59-61 and light chain CDRs having the amino acid sequences of SEQ ID NOs: 62-64 or a conservative substitution variant of such amino acid sequence; or heavy chain CDRs having the amino acid sequences of SEQ ID NOs: 65-67 and light chain CDRs having the amino acid sequences of SEQ ID NOs: 68-70 or a conservative substitution variant of such amino acid sequence; or heavy chain CDRs having the amino acid sequences of SEQ ID NOs: 71-73 and light chain CDRs having the amino acid sequences of SEQ ID NOs: 74-76 or a conservative substitution variant of such amino acid sequence; or heavy chain CDRs having the amino acid sequences of SEQ ID NOs: 77-79 and light chain CDRs having the amino acid sequences of SEQ ID NOs: 80-82 or a conservative substitution variant of such amino acid sequence; or heavy chain CDRs having the amino acid sequences of SEQ ID NOs: 83-85 and light chain CDRs having the amino acid sequences of SEQ ID NOs: 86-88 or a conservative substitution variant of such amino acid sequence.

In some embodiments of any of the aspects, the antibody, antibody reagent, antigen-binding portion thereof, or CAR comprises the heavy chain sequence of any of SEQ ID NOs: 1, 3, 5, 7, 9, 11, 13, 15, 17, 19 or 21. In some embodiments of any of the aspects, the antibody, antibody reagent, antigen-binding portion thereof, or CAR comprises the light chain sequence of any of SEQ ID NOs: 2, 4, 6, 8, 10, 12, 14, 16, 18, 20, or 22. In some embodiments of any of the aspects, the antibody, antibody reagent, antigen-binding portion thereof, or CAR comprises the heavy chain sequence of SEQ ID NO: 1 and the light chain sequence of SEQ ID NO: 2; or the heavy chain sequence of SEQ ID NO: 3 and the light chain sequence of SEQ ID NO: 4; or the heavy chain sequence of SEQ ID NO: 5 and the light chain sequence of SEQ ID NO: 6; or the heavy chain sequence of SEQ ID NO: 7 and the light chain sequence of SEQ ID NO: 8; or the heavy chain sequence of SEQ ID NO: 9 and the light chain sequence of SEQ ID NO: 10; or the heavy chain sequence of SEQ ID NO: 11 and the light chain sequence of SEQ ID NO: 12; or the heavy chain sequence of SEQ ID NO: 13 and the light chain sequence of SEQ ID NO: 14; or the heavy chain sequence of SEQ ID NO: 15 and the light chain sequence of SEQ ID NO: 16; or the heavy chain sequence of SEQ ID NO: 17 and the light chain sequence of SEQ ID NO: 18; or the heavy chain sequence of SEQ ID NO: 19 and the light chain sequence of SEQ ID NO: 20; or the heavy chain sequence of SEQ ID NO: 21 and the light chain sequence of SEQ ID NO: 22.

In some embodiments of any of the aspects, the antibody, antibody reagent, antigen-binding portion thereof, or CAR comprises one or more of the CDRs of an antibody of FIGS. 1-4. In some embodiments of any of the aspects, the antibody, antibody reagent, antigen-binding portion thereof, or CAR comprises the six CDRs of an antibody of FIGS. 1-4. In some embodiments of any of the aspects, the antibody, antibody reagent, antigen-binding portion thereof, or CAR comprises the light chain, heavy chain, or heavy and light chains of an antibody of FIGS. 1-4. In some embodiments of any of the aspects, the antibody, antibody reagent, antigen-binding portion thereof, or CAR is an antibody of FIGS. 1-4.

(a) In some embodiments, the antibody, antibody reagent, antigen-binding portion thereof, or CAR can comprise one or more CDRs (e.g., one CDR, two CDRs, three CDRs, four CDRs, five CDRs, or six CDRs) having the sequence of a CDR selected from SEQ ID NOs: 23-88. In some embodiments, the antibody, antibody reagent, antigen-binding portion thereof, or CAR can comprise CDRs having the sequence of the CDRs of an antibody of Table 1.

In one aspect of any of the embodiments, described herein is an antibody, antibody reagent, antigen-binding portion thereof, or CAR that specifically binds an PD1 polypeptide, and can compete for binding of PD1 with an antibody selected from FIGS. 1-4, or having the CDRs of an antibody selected from FIGS. 1-4.

In some embodiments, the antibody, antibody reagent, antigen-binding portion thereof, and/or CAR as described herein can be a variant of a sequence described herein, e.g., a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or portion thereof that retains activity, e.g., antigen-specific binding activity for the relevant target polypeptide, e.g., PD1. A wide variety of PCR-based site-specific mutagenesis approaches are also known in the art and can be applied by the ordinarily skilled artisan.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g., PD1). Such conservatively modified variants are in addition to and do not exclude polymorphic variants, interspecies homologs, and alleles consistent with the disclosure.

Examples of substitution variants include conservative substitution of amino acids, e.g., in a $V_H$ or $V_L$ domain, that do not alter the sequence of a CDR. A conservative substitution in a sequence not comprised by a CDR can be a substitution relative to a wild-type or naturally-occurring sequence, e.g., human or murine framework and/or constant regions of an antibody sequence. In some embodiments, a conservatively modified variant of an antibody reagent can comprise alterations other than in the CDRs, e.g., a conservatively modified variant of an antibody, antibody reagent, antigen-binding portion thereof, or CAR can comprise CDRs having the sequence of one or more of SEQ ID NOs 23-88. In some embodiments, a conservatively modified variant of an antibody, antibody reagent, antigen-binding portion thereof, or CAR can comprise CDRs having the sequences of an antibody of Table 1.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val;

Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In particular embodiments wherein an antibody, antigen-binding portion thereof, or CAR as described herein comprises at least one CDR which is not identical to the sequence of SEQ ID NOs: 23-88, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding portion thereof as described herein, will result in an antigen or antigen-binding portion thereof which will bind a cancer cell surface antigen. The method described in Fujii et al. also permits one of ordinary skill in the art to screen for a light chain sequence which will give the desired binding behavior when combined with a known heavy chain fragment and vice versa.

In some embodiments, a CAR comprises an extracellular domain comprising an anti-PD1 antibody or antigen-binding portion thereof that binds one or more epitopes of a PD1 polypeptide; a transmembrane domain, one or more intracellular co-stimulatory signaling domains, and a primary signaling domain. Exemplary anti-PD1 antibodies and antigen-binding portions thereof, as well as exemplary epitopes, are described elsewhere herein.

As used herein, "chimeric antigen receptor" or "CAR" refers to an artificially constructed hybrid polypeptide comprising an antigen-binding domain (e.g., an antigen-binding portion of an antibody (e.g., a scFV)), a transmembrane domain, and a T-cell signaling and/or T-cell activation domain. CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries), in various embodiments, this scFv is fused to a transmembrane domain and then to an intracellular signaling domain. "First-generation" CARs include those that solely provide CD3zeta (CD3$\zeta$) signals upon antigen binding, "Second-generation" CARs include those that provide both costimulation (e.g., CD28 or CD 137) and activation (CD3$\zeta$). "Third-generation" CARs include those that provide multiple costimulatory (e.g., CD28 and CD 137) domains and activation domains (e.g., CD3$\zeta$). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In some embodiments of any of the aspects, a CAR comprises an extracellular binding domain that comprises a humanized PD1-specific binding domain; a transmembrane domain; one or more intracellular co-stimulatory signaling domains; and a primary signaling domain. As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest, e.g., PD1. The binding domain may be derived either from a natural, synthetic, semi-synthetic, or recombinant source.

In some embodiments, the CARs contemplated herein may comprise linker residues between the various domains, e.g., added for appropriate spacing and conformation of the molecule. In particular embodiments the linker is a variable region linking sequence. A "variable region linking sequence," is an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, can comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation. The hinge domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8a, CD4, CD28 and CD7, which may be wild-type hinge regions from these molecules or may be altered. In another embodiment, the hinge domain comprises a CD8a hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from (i.e., comprise at least the transmembrane region(s) of) the alpha, beta or zeta chain of the T-cell receptor, CD3ε, CD3ζ, CD4, CD5, CD8a, CD9, CD 16, CD22, CD27, CD28, CD33, CD37, CD45, CD64, CD80, CD86, CD 134, CD137, CD152, CD 154, and PD1.

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are of particular use in the invention include those derived from TCRζ, FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, a CAR comprises one or more co-stimulatory signaling domains selected from the group consisting of CD28, CD137, and CD134, and a CD3ζ primary signaling domain.

In some embodiments, an antibody-drug conjugate is provided. In particular embodiments, an antibody-drug conjugate comprises an antibody, antibody reagent, or antigen-binding portion thereof as described herein. The drug can be, e.g., a chemotherapeutic molecule as described elsewhere herein. In some embodiments, the antibody-drug conjugate comprises a chemotherapeutic agent directly conjugated and/or bound to an antibody or antigen-binding portion thereof. In some embodiments, binding can be non-covalent, e.g., by hydrogen bonding, electrostatic, or van der Waals interactions; however, binding may also be covalent. By "conjugated" is meant the covalent linkage of at least two molecules. In some embodiments, the composition can be an antibody-drug conjugate.

In some embodiments, an antibody, antibody reagent, or antigen-binding portion thereof can be bound to and/or conjugated to multiple chemotherapeutic molecules. In some embodiments, an antibody-drug conjugate can be bound to and/or conjugated to multiple chemotherapeutic molecules. In some embodiments, the ratio of a given chemotherapeutic molecule to an antibody or antigen-binding portion thereof can be from about 1:1 to about 1,000:1, e.g., a single antibody reagent molecule can be linked to, conjugated to, etc. from about 1 to about 1,000 individual chemotherapeutic molecules.

In some embodiments, an antibody, or antigen-binding portion thereof, and the chemotherapeutic agent can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one to several billionths of a meter. The term "nanoparticle" includes nanospheres; nanorods; nanoshells; and nanoprisms; these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g., an antibody or antigen-binding portion thereof). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are super-absorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo. As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

In some embodiments, the technology described herein relates to a nucleic acid encoding an antibody, antibody reagent, antigen-binding portion thereof, or CAR as described herein. In some embodiments, the nucleic acid is a cDNA.

As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. In some embodiments, the nucleic acid can be a cDNA, e.g., a nucleic acid lacking introns.

Nucleic acid molecules encoding amino acid sequence variants of antibodies are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations can be used to construct nucleic acid sequences which encode a monoclonal antibody molecule, antibody reagent, antigen binding region thereof, or CAR.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art.

In some embodiments, a nucleic acid encoding an antibody, antibody reagent, antigen-binding portion thereof, or CAR as described herein is comprised by a vector. In some of the aspects described herein, a nucleic acid sequence encoding an antibody, antibody reagent, antigen-binding portion thereof, or CAR as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody, antigen-binding portion thereof, or CAR as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In one aspect of any of the embodiments, described herein is a cell comprising an antibody, antibody reagent, antigen-binding portion thereof, or CAR as described herein, or a nucleic acid encoding such an antibody, antibody reagent, antigen-binding portion thereof, or CAR.

The expression of an antibody, antibody reagent, antigen-binding portion thereof, or CAR as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Any of a series of yeast gene expression systems incorporating promoter and termination elements from the actively expressed genes coding for glycolytic enzymes produced in large quantities when yeast are grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of ordinary skill in the art.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli.*, for example. Other gene expression elements useful for the expression of cDNA encoding antibodies, antigen-binding portions thereof, or CARs include, but are not limited to (a) viral transcription promoters and their enhancer elements, such as the SV40 early promoter, Rous sarcoma virus LTR, and Moloney murine leukemia virus; (b) splice regions and polyadenylation sites such as those derived from the SV40 late region, and (c) polyadenylation sites such as in SV40. Immunoglobulin cDNA genes can be expressed, e.g., using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA, the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

A gene is assembled in, or inserted into, an expression vector. Recipient cells capable of expressing the chimeric immunoglobulin chain gene product are then transfected singly with an antibody, antigen-binding portion thereof, or CAR, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the genes encoding the antibody, antigen-binding portion thereof, CAR, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the genes can be assembled on the same expression vector.

For transfection of the expression vectors and production of the antibodies, antibody reagents, antigen-binding portions thereof, or CARs described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, antigen-binding portion thereof, and/or CAR as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment, as known to one of ordinary skill in the art.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

In one aspect, a cell comprising an isolated antibody, antigen-binding portion thereof, or CAR as described herein is provided. In some embodiments, the isolated antibody, antigen-binding portion thereof, or CAR as described herein is expressed on the cell surface. In some embodiments, the cell comprises a nucleic acid encoding an isolated antibody, antigen-binding portion thereof, or CAR as described herein.

In some embodiments, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the cell is a T cell; a NK cell; a NKT cell; lymphocytes, such as B cells and T cells; and myeloid cells, such as monocytes, macrophages, eosinophils, mast cells, basophils, and granulocytes.

In particular embodiments, a cell (e.g., an immune cell) is transduced with a retroviral vector, e.g., a lentiviral vector, encoding a CAR. For example, an immune effector cell is transduced with a vector encoding a CAR that comprises an anti-PD1 antibody or antigen binding portion thereof that binds a PD1 polypeptide, with an intracellular signaling domain of CD3ζ, CD28, 4-1BB, Ox40, or any combinations thereof. Thus, these transduced cells can elicit a CAR-mediated cytotoxic response.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

Retroviral vectors and more particularly lentiviral vectors may be used in practicing particular embodiments of the present invention. Accordingly, the term "retrovirus" or "retroviral vector", as used herein is meant to include "lentivirus" and "lentiviral vectors" respectively.

In one aspect of any of the embodiments, described herein is a compositions comprising an antibody, antibody reagent, antigen-binding portion thereof, or CAR as described herein or a nucleic acid encoding an antibody, antibody reagent, antigen-binding portion thereof, or CAR as described herein or a cell as described herein. In some embodiments, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, the composition comprising an antibody, antibody reagent, antigen-binding portion thereof, or CAR as described herein or a nucleic acid encoding an antibody, antibody reagent, antigen-binding portion thereof, or CAR as described herein can be a lyophilisate.

In some embodiments, the technology described herein relates to a syringe or catheter, including an organ-specific catheter (e.g., renal catheter, biliary catheter, cardiac catheter, etc.), comprising a therapeutically effective amount of a composition described herein.

As used herein, the phrase "therapeutically effective amount", "effective amount" or "effective dose" refers to an amount that provides a therapeutic or aesthetic benefit in the treatment, prevention, or management of a tumor or malignancy, e.g., an amount that provides a statistically significant decrease in at least one symptom, sign, or marker of a tumor or malignancy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents In one aspect, the technology described herein relates to a method comprising administering an antibody, antibody reagent, antigen-binding portion thereof, or CAR as described herein or a nucleic acid encoding an antibody, antibody reagent, antigen-binding portion thereof, or CAR as described herein to a subject. In some embodiments, the subject is in need of treatment for a cancer and/or malignancy. In some embodiments, the method is a method of treating a subject. In some embodiments, the method is a method of treating a cancer in a subject.

In one aspect, described herein is a method of treating cancer in a subject in need thereof, the method comprising administering a cell as described herein, e.g., a cell comprising an antibody, antibody reagent, antigen-binding portion thereof, or CAR as described herein. In some embodiments, the cell is an immune cell.

In one aspect, described herein is a method of treating cancer in a subject in need thereof, the method comprising administering a nucleic acid as described herein or an immune cell comprising the nucleic acid to the subject, wherein the subject's immune cells are caused to express the polypeptide encoded by the nucleic acid. In some embodiments, the immune cell is a T cell. Nucleic acids can be targeted to particular cell types by, e.g., use of a cell-type specific promoter and/or a composition that selectively binds to the desired cell type. For example, conjugation of a nucleic acid to an aptamer can permit targeted delivery (McNamara, J O., et al. (2006) Nat. Biotechnol. 24:1005-1015). In an alternative embodiment, the nucleic acid can be delivered using drug delivery systems such as a nanoparticle, a dendrimer, a polymer, liposomes, or a cationic delivery system. Positively charged cationic delivery systems facilitate binding of an nucleic acid molecule (negatively charged) and also enhance interactions at the negatively charged cell membrane to permit efficient uptake of a nucleic acid by the cell. Cationic lipids, dendrimers, or polymers can either be bound to a nucleic acid, or induced to form a vesicle or micelle (see e.g., Kim S H., et al. (2008) Journal of Controlled Release 129(2):107-116) that encases a nucleic acid. The formation of vesicles or micelles further prevents degradation of the nucleic acid when administered systemically. Methods for making and administering cationic-inhibitory nucleic acid complexes are well within the abilities of one skilled in the art. Some non-limiting examples of drug delivery systems useful for systemic delivery of nucleic acids include DOTAP Oligofectamine, "solid nucleic acid lipid particles", cardiolipin, polyethyleneimine, Arg-Gly-Asp (RGD) peptides, and polyamidoamines. In some embodiments, a nucleic acid forms a complex with cyclodextrin for systemic administration. Methods for administration and pharmaceutical compositions of nucleic acids and cyclodextrins can be found in U.S. Pat. No. 7,427,605, which is herein incorporated by reference in its entirety. Targeted delivery of nucleic acids is described, for example in Ikeda and Taira Pharmaceutical Res 2006 23:1631-1640; Soutschek et al., Nature 2004 432:173-8 and Lorenze et al. Bioorg. Med. Chem. Lett. 14, 4975-4977 (2004); each of which is incorporated by reference herein in its entirety. By way of example, the nucleic acid can be targeted to immune cells by encapsulating the inhibitor in a liposome comprising ligands of receptors expressed on immune cells, e.g., TCRs. In some embodiments, the liposome can comprise aptamers specific for immune cells.

In some embodiments, the methods described herein relate to CAR-T cell therapy. CAR-T cell and related therapies relate to adoptive cell transfer of immune cells (e.g., T cells) expressing a CAR that binds specifically to a targeted cell type (e.g., cancer cells) to treat a subject. In some embodiments, the cells administered as part of the therapy can be autologous to the subject. In some embodiments, the cells administered as part of the therapy are not autologous to the subject. In some embodiments, the cells are engineered and/or genetically modified to express the CAR. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments of any of the aspects, the cancer can be non-small cell lung cancer; melanoma; metastatic melanoma; renal cell carcinoma; squamous cell carcinoma of the head and neck; Hodgkin lymphoma; classical Hodgkin lymphoma; and/or urothelial carcinoma.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patients or subjects include any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, various cancers. In addition, the methods described herein can be used to treat domesticated animals and/or pets. A subject can be male or female.

A subject can be one who has been previously diagnosed with or identified as suffering from or having a condition in need of treatment (e.g., a cancer) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment. As used herein, the term "administering," refers to the placement of an agent, including but not limited to, an antibody, antibody reagent, antigen-binding portion thereof, or CAR as described herein or a nucleic acid encoding an antibody, antibody reagent, antigen-binding portion thereof, or CAR, or a cell comprising such an agent, as described herein into a subject by a method or route which results in at least partial localization of the agents at a desired site. The pharmaceutical composition comprising an antibody, antibody reagent, antigen-binding portion thereof, or CAR as described herein or a nucleic acid encoding an antibody, antibody reagent, antigen-binding portion thereof, or CAR, or a cell comprising such an agent as described herein disclosed herein can be administered by any appropriate route which results in an effective treatment in the subject.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

It can generally be stated that a pharmaceutical composition comprising the cells, e.g., T cells or immune cells, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^1$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. CAR expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response. In some embodiments, the dosage can be from about $1\times10^5$ cells to about $1\times10^8$ cells per kg of body weight. In some embodiments, the dosage can be from about $1\times10^6$ cells to about $1\times10^7$ cells per kg of body weight. In some embodiments, the dosage can be about $1\times10^6$ cells per kg of body weight. In some embodiments, one dose of cells can be administered. In some embodiments, the dose of cells can be repeated, e.g., once, twice, or more. In some embodiments, the dose of cells can be administered on, e.g., a daily, weekly, or monthly basis.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 0.5 mg/kg body weight. In some embodiments, the dose range is from 5 g/kg body weight to 100 g/kg body weight. Alternatively, the dose range can be titrated to maintain serum levels between 1 g/mL and 1000 g/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Administration of the doses recited above can be repeated. In some embodiments, the doses are given once a day, or multiple times a day, for example but not limited to three times a day. In a some embodiments, the doses recited above are administered daily for several weeks or months. The duration of treatment depends upon the subject's clinical progress and responsiveness to therapy.

In some embodiments, the dose can be from about 2 mg/kg to about 15 mg/kg. In some embodiments, the dose can be about 2 mg/kg. In some embodiments, the dose can be about 4 mg/kg. In some embodiments, the dose can be about 5 mg/kg. In some embodiments, the dose can be about 6 mg/kg. In some embodiments, the dose can be about 8 mg/kg. In some embodiments, the dose can be about 10 mg/kg. In some embodiments, the dose can be about 15 mg/kg. In some embodiments, the dose can be from about 100 mg/m$^2$ to about 700 mg/m$^2$. In some embodiments, the dose can be about 250 mg/m$^2$. In some embodiments, the dose can be about 375 mg/m$^2$. In some embodiments, the dose can be about 400 mg/m$^2$. In some embodiments, the dose can be about 500 mg/m$^2$.

In some embodiments, the dose can be administered intravenously. In some embodiments, the intravenous administration can be an infusion occurring over a period of from about 10 minute to about 3 hours. In some embodiments, the intravenous administration can be an infusion occurring over a period of from about 30 minutes to about 90 minutes.

In some embodiments the dose can be administered about weekly. In some embodiments, the dose can be administered weekly. In some embodiments, the dose can be administered weekly for from about 12 weeks to about 18 weeks. In some embodiments the dose can be administered about every 2 weeks. In some embodiments the dose can be administered about every 3 weeks. In some embodiments, the dose can be from about 2 mg/kg to about 15 mg/kg administered about every 2 weeks. In some embodiments, the dose can be from about 2 mg/kg to about 15 mg/kg administered about every 3 weeks. In some embodiments, the dose can be from about 2 mg/kg to about 15 mg/kg administered intravenously about every 2 weeks. In some embodiments, the dose can be from about 2 mg/kg to about 15 mg/kg administered intravenously about every 3 weeks. In some embodiments, the dose can be from about 200 mg/m$^2$ to about 400 mg/m$^2$ administered intravenously about every week. In some embodiments, the dose can be from about 200 mg/m$^2$ to about 400 mg/m$^2$ administered intravenously about every 2 weeks. In some embodiments, the dose can be from about 200 mg/m$^2$ to about 400 mg/m$^2$ administered intravenously about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

In some embodiments, the dose can be from about 1 mg to about 2000 mg. In some embodiments, the dose can be about 3 mg. In some embodiments, the dose can be about 10 mg. In some embodiments, the dose can be about 30 mg. In some embodiments, the dose can be about 1000 mg. In some embodiments, the dose can be about 2000 mg. In some embodiments, the dose can be about 3 mg given by intravenous infusion daily. In some embodiments, the dose can be about 10 mg given by intravenous infusion daily. In some embodiments, the dose can be about 30 mg given by intravenous infusion three times per week.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments, the methods further comprise administering the pharmaceutical composition described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, antibody reagents, and/or small molecules.

In some embodiments of the methods described herein, the methods further comprise administering one or more chemotherapeutic agents to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any one of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g., see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ Edition, 2000 Churchill Livingstone, Inc; Baltzer L, Berkery R (eds)). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments, the methods described herein can further comprise administering an additional immunotherapy to the subject. As used herein, "immunotherapy" refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g., interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat. No. 8,329,660. In some embodiments, the immunotherapy stimulates NK responses. In some embodiments, the immunotherapy is an adoptive cell transfer approach, i.e., adoptive immunotherapy.

In some embodiments, the methods described herein can further comprise administering an additional antibody, antibody reagent, antigen-binding portion thereof, or T cell comprising a CAR to the subject. In some embodiments, the methods described herein can further comprise administering cytokine to the subject. Antibody- and cytokine-based therapies are known in the art and can include, by way of non-limiting example, alemtuzumab; bevacizumab; brentuximab vedotin; cetuximab; gemtuzumab; ibritumomab tiuxetan; ipilimumab; ofatumumab; pantibumumab; rituximab; tositumomab; trastuzumab; interleukin-2, and interferon-alpha.

The efficacy of a given treatment for, e.g., cancer, can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc.

In one aspect, described herein is a method of detecting PD1, the method comprising contacting a biological sample with an antibody, antibody reagent, or antigen-binding portion thereof as described herein, wherein reaction of the antibody or antigen-binding portion thereof with PD1 indicates the presence of PD1.

In some embodiments, a detectable signal is generated by the antibody or antigen-binding portion thereof when a PD1 molecule is present. In some embodiments, the antibody or antigen-binding portion thereof is detectably labeled or capable of generating a detectable signal. In some embodiments, the level of the PD1 is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluorescence assay; mass spectroscopy; FACS; and immunoelectrophoresis assay. In some embodiments, the antibody or antigen-binding portion thereof is detectably labeled or generates a detectable signal. In some embodiments, the expression level of PD1 is normalized relative to the expression level of one or more reference genes or reference proteins. In some embodiments, the reference level of PD1 is the expression level of PD1 in a prior sample obtained from the subject.

In some embodiments, the level of PD1 can be the level of PD1 polypeptide. Detection of PD1 polypeptides can be according to any method known in the art. Immunological methods to detect PD1 polypeptides in accordance with the present technology include, but are not limited to antibody techniques such as immunohistochemistry, immunocytochemistry, flow cytometry, fluorescence-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g., the antigen or in the embodiments described herein, a PD1 polypeptide. In some embodiments, the assays, methods, and/or systems described herein can comprise: an anti-PD1 antibody reagent. In some embodiments, the antibody reagent can be detectably labeled. In some embodiments, the antibody reagent can be attached to a solid support (e.g., bound to a solid support). In some embodiments, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g., PD1). The solid support can then be contacted with a second labeled antibody reagent (e.g., a detection antibody reagent). The detection antibody reagent can, e.g., comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e., the presence of a signal indicated the presence of a PD1 molecule. Between each step the plate is typically washed with a mild detergent solution to remove any proteins or antibodies that are not specifically bound. After the final wash step the plate is developed by adding an enzymatic substrate to produce a visible signal, which indicates the quantity of PD1 polypeptides in the sample. Older ELISAs utilize chromogenic substrates, though newer assays employ fluorogenic substrates with much higher sensitivity. There are other different forms of ELISA, which are well known to those skilled in the art.

In one embodiment, the assays, systems, and methods described herein can comprise a lateral flow immunoassay test (LFIA), also known as the immunochromatographic assay, or strip test to measure or determine the level of PD1 polypeptide in a sample. LFIAs are a simple device intended to detect the presence (or absence) of PD1 in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of PD1 present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g., a PD1-specific antibody reagent). The test line will also contain antibody reagents (e.g., a PD1-specific antibody reagent). The test line will show as a colored band in positive samples. In some embodiments, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i.e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports has been described in the art in the context of an immunoassay for a number of antigen biomarkers. U.S. Pat. Nos. 4,943,522; 6,485,982; 6,187,598; 5,770,460; 5,622, 871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of PD1 polypeptides. In some embodiments, the dip stick (or LFIA) can be suitable for use with urine samples. In some embodiments, a dip stick can be suitable for use with blood samples.

Immunochemistry is a family of techniques based on the use of a specific antibody, wherein antibodies are used to specifically target molecules inside or on the surface of cells. In some embodiments, immunohistochemistry ("IHC") and immunocytochemistry ("ICC") techniques can be used to detect or measure the levels of PD1 polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in Burry "Immunocytochemistry: A Practical Guide for Biomedical Research" Springer (2009); which is incorporated by reference herein in its entirety.

In some embodiments, one or more of the antibody reagents described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is labeled with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4', 7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

In some embodiments, a detectable label can be a radiolabel including, but not limited to $^{3}H$, $^{125}I$, $^{35}S$, $^{14}C$, $^{32}P$, and $^{33}P$.

In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments, a detectable label is a chemiluminescent label, including, but not limited to lucigenin, luminol, luciferin, isoluminol, theromatic acridinium ester, imidazole, acridinium salt and oxalate ester.

In some embodiments, a detectable label can be a spectral colorimetric label including, but not limited to colloidal gold or colored glass or plastic (e.g., polystyrene, polypropylene, and latex) beads.

In some embodiments, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, CA.

An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

The term "sample" or "test sample" as used herein denotes a sample taken or isolated from an organism, e.g., a urine sample from a subject. Exemplary biological samples include, but are not limited to, a biofluid sample; serum; plasma; urine; saliva; and/or tumor sample, etc. The term also includes a mixture of the above-mentioned samples. The term "test sample" also includes untreated or pretreated (or pre-processed) biological samples. In some embodiments, a test sample can comprise cells from a subject. As used herein, the term "biofluid" refers to any fluid obtained from a biological source and includes, but is not limited to, blood, urine, and bodily secretions.

The test sample can be obtained by removing a sample from a subject, but can also be accomplished by using a previously isolated sample (e.g., isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, prepared by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of PD1 as described herein.

In some embodiments, the methods, assays, and systems described herein can further comprise a step of obtaining a test sample from a subject. In some embodiments, the subject can be a human subject.

In some embodiments, the assay or method can further comprise the step of administering an anti-PD1 therapy. In some embodiments, the anti-PD1 therapy comprises an isolated antibody, antibody reagent, antigen-binding portion thereof, or CAR or CAR T cell; nucleic acid; cell; or composition as described herein.

In one aspect of any of any of the embodiments, described herein is an antibody, antibody reagent, or antigen-binding portion thereof as described herein conjugated to or coupled to a detectable label.

In one aspect of any of any of the embodiments, described herein is a solid support comprising an antibody, antibody reagent, antigen-binding fragment thereof as described herein. In some embodiments of any of the aspects, the antibody, antibody reagent or antigen-binding fragment thereof is detectably labeled. In some embodiments of any of the aspects, the solid support comprises a particle, a bead, a polymer, or a substrate.

In one aspect of any of the embodiments, described herein is a molecular complex comprising at least one antibody, antibody reagent, antigen-binding fragment thereof, or CAR of as described herein bound to an PD1 polypeptide.

In one aspect, described herein is a kit comprising a composition as described herein, e.g., a composition comprising an antibody, antibody reagent, antigen-binding portion thereof, or CAR as described herein. A kit is any manufacture (e.g., a package or container) comprising at least one reagent, e.g., an antibody, the manufacture being promoted, distributed, or sold as a unit for performing the methods described herein. In some embodiments of any of the aspects, the antibody, antibody reagent, antigen-binding fragment thereof as described herein is immobilized on a solid support. In some embodiments of any of the aspects, the solid support comprises a particle, a bead, a polymer, or a substrate. In some embodiments of any of the aspects, the antibody, antibody reagent or antigen-binding fragment thereof is detectably labeled.

The kits described herein can optionally comprise additional components useful for performing the methods described herein. By way of example, the kit can comprise fluids (e.g., buffers) suitable for composition comprising an antibody, antigen-binding portion thereof, or CAR as described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments, a nucleic acid encoding a polypeptide as described herein (e.g. an antibody or antibody reagent) is comprised by a vector. In some of the aspects described herein, a nucleic acid sequence encoding a given polypeptide as described herein, or any module thereof, is operably linked to a vector. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more. In some embodiments, the antibody, antigen-binding portion thereof, or CAR described herein is isolated. In some embodiments, the antibody, antibody reagent, antigen-binding portion thereof, or CAR described herein is purified.

As used herein, "engineered" refers to the aspect of having been manipulated by the hand of man. For example, an antibody, antibody reagent, antigen-binding portion thereof, or CAR is considered to be "engineered" when the sequence of the antibody, antibody reagent, antigen-binding portion thereof, or CAR is manipulated by the hand of man to differ from the sequence of an antibody as it exists in nature. As is common practice and is understood by those in the art, progeny and copies of an engineered polynucleotide and/or polypeptide are typically still referred to as "engineered" even though the actual manipulation was performed on a prior entity.

As used herein, an "epitope" can be formed on a polypeptide both from contiguous amino acids, or noncontiguous amino acids juxtaposed by tertiary folding of a protein.

Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^{5}$ to $10^{12}$ liter/moles or more, such as $10^{7}$ to $10^{12}$ liter/moles or $10^{8}$ to $10^{12}$ liter/moles). Any KD value greater than $10^{-4}$ mol/liter (or any KA value lower than $10^{4}$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an peptide (e.g., an antibody, CAR or portion thereof) described herein to bind to a target, such as an antigen present on the cell-surface of a cancer cell, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody, antigen-binding portion thereof, or CAR is said to specifically bind an antigen when it preferentially recognizes its target antigen in a complex mixture of proteins and/or macromolecules.

In some embodiments, an antibody, antigen-binding portion thereof, and/or CAR as described herein binds to PD1 with a dissociation constant ($K_D$) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody, antigen-binding portion thereof, and/or CAR as described herein binds to PD1 with a dissociation constant ($K_D$) of from about $10^{-5}$ M to $10^{-6}$ M. In some embodiments, an antibody, antigen-binding portion thereof, and/or CAR as described herein binds to PD1 with a dissociation constant ($K_D$) of from about $10^{-6}$ M to $10^{-7}$ M. In some embodiments, an antibody, antigen-binding portion thereof, and/or CAR as described herein binds to PD1 with a dissociation constant ($K_D$) of from about $10^{-7}$ M to $10^{-8}$ M. In some embodiments, an antibody, antigen-binding portion thereof, and/or CAR as described herein binds to PD1 with a dissociation constant ($K_D$) of from about $10^{-8}$ M to $10^{-9}$ M. In some embodiments, an antibody, antigen-binding portion thereof, and/or CAR as described herein binds to PD1 with a dissociation constant ($K_D$) of from about $10^{-9}$ M to $10^{-10}$ M. In some embodiments, an antibody, antigen-binding portion thereof, and/or CAR as described herein binds to PD1 with a dissociation constant ($K_D$) of from about $10^{-10}$ M to $10^{-11}$ M. In some embodiments, an antibody, antigen-binding portion thereof, and/or CAR as described herein binds to PD1 with a dissociation constant ($K_D$) of from about $10^{-11}$ M to $10^{-12}$ M. In some embodiments, an antibody, antigen-binding portion thereof, and/or CAR as described herein binds to PD1 with a dissociation constant ($K_D$) of less than $10^{-12}$ M.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier;

and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An antibody, antibody reagent, antigen-binding fragment thereof, or chimaeric antigen receptor (CAR), that specifically binds an PD1 polypeptide, said antibody reagent, antigen-binding portion thereof, or CAR comprising at least one heavy or light chain complementarity determining region (CDR) selected from the group consisting of:

(a) a heavy chain CDR1 having the amino acid sequence of SEQ ID NO: 23;

(b) a heavy chain CDR2 having the amino acid sequence of SEQ ID NO: 24;

(c) a heavy chain CDR3 having the amino acid sequence of SEQ ID NO: 25;

(d) a light chain CDR1 having the amino acid sequence of SEQ ID NO: 26;

(e) a light chain CDR2 having the amino acid sequence of SEQ ID NO: 27; and (f) a light chain CDR3 having the amino acid sequence of SEQ ID NO: 28; or selected from the group consisting of:

(a) a heavy chain CDR1 having the amino acid sequence of SEQ ID NO: 29;

(b) a heavy chain CDR2 having the amino acid sequence of SEQ ID NO: 30;

(c) a heavy chain CDR3 having the amino acid sequence of SEQ ID NO: 31;

(d) a light chain CDR1 having the amino acid sequence of SEQ ID NO: 32;

(e) a light chain CDR2 having the amino acid sequence of SEQ ID NO: 33; and (f) a light chain CDR3 having the amino acid sequence of SEQ ID NO: 34; or selected from the group consisting of:

(a) a heavy chain CDR1 having the amino acid sequence of SEQ ID NO: 35;

(b) a heavy chain CDR2 having the amino acid sequence of SEQ ID NO: 36;

(c) a heavy chain CDR3 having the amino acid sequence of SEQ ID NO: 37;

(d) a light chain CDR1 having the amino acid sequence of SEQ ID NO: 38;

(e) a light chain CDR2 having the amino acid sequence of SEQ ID NO: 39; and (f) a light chain CDR3 having the amino acid sequence of SEQ ID NO: 40; or selected from the group consisting of:

(a) a heavy chain CDR1 having the amino acid sequence of SEQ ID NO: 41;

(b) a heavy chain CDR2 having the amino acid sequence of SEQ ID NO: 42;

(c) a heavy chain CDR3 having the amino acid sequence of SEQ ID NO: 43;

(d) a light chain CDR1 having the amino acid sequence of SEQ ID NO: 44;

(e) a light chain CDR2 having the amino acid sequence of SEQ ID NO: 45; and (f) a light chain CDR3 having the amino acid sequence of SEQ ID NO: 46; or selected from the group consisting of:

(a) a heavy chain CDR1 having the amino acid sequence of SEQ ID NO: 47;

(b) a heavy chain CDR2 having the amino acid sequence of SEQ ID NO: 48;

(c) a heavy chain CDR3 having the amino acid sequence of SEQ ID NO: 49;

(d) a light chain CDR1 having the amino acid sequence of SEQ ID NO: 50;

(e) a light chain CDR2 having the amino acid sequence of SEQ ID NO: 51; and (f) a light chain CDR3 having the amino acid sequence of SEQ ID NO: 52; or selected from the group consisting of:

(a) a heavy chain CDR1 having the amino acid sequence of SEQ ID NO: 53;

(b) a heavy chain CDR2 having the amino acid sequence of SEQ ID NO: 54;

(c) a heavy chain CDR3 having the amino acid sequence of SEQ ID NO: 55;

(d) a light chain CDR1 having the amino acid sequence of SEQ ID NO: 56;

(e) a light chain CDR2 having the amino acid sequence of SEQ ID NO: 57; and (f) a light chain CDR3 having the amino acid sequence of SEQ ID NO: 58; or selected from the group consisting of:

(a) a heavy chain CDR1 having the amino acid sequence of SEQ ID NO: 59;

(b) a heavy chain CDR2 having the amino acid sequence of SEQ ID NO: 60;

(c) a heavy chain CDR3 having the amino acid sequence of SEQ ID NO: 61;

(d) a light chain CDR1 having the amino acid sequence of SEQ ID NO: 62;

(e) a light chain CDR2 having the amino acid sequence of SEQ ID NO: 63; and (f) a light chain CDR3 having the amino acid sequence of SEQ ID NO: 64; or selected from the group consisting of:

(a) a heavy chain CDR1 having the amino acid sequence of SEQ ID NO: 65;

(b) a heavy chain CDR2 having the amino acid sequence of SEQ ID NO: 66;

(c) a heavy chain CDR3 having the amino acid sequence of SEQ ID NO: 67;

(d) a light chain CDR1 having the amino acid sequence of SEQ ID NO: 68;

(e) a light chain CDR2 having the amino acid sequence of SEQ ID NO: 69; and (f) a light chain CDR3 having the amino acid sequence of SEQ ID NO: 70; or selected from the group consisting of:

(a) a heavy chain CDR1 having the amino acid sequence of SEQ ID NO: 71;

(b) a heavy chain CDR2 having the amino acid sequence of SEQ ID NO: 72;

(c) a heavy chain CDR3 having the amino acid sequence of SEQ ID NO: 73;

(d) a light chain CDR1 having the amino acid sequence of SEQ ID NO: 74;

(e) a light chain CDR2 having the amino acid sequence of SEQ ID NO: 75; and (f) a light chain CDR3 having the amino acid sequence of SEQ ID NO: 76; or selected from the group consisting of:

(a) a heavy chain CDR1 having the amino acid sequence of SEQ ID NO: 77;

(b) a heavy chain CDR2 having the amino acid sequence of SEQ ID NO: 78;

(c) a heavy chain CDR3 having the amino acid sequence of SEQ ID NO: 79;

(d) a light chain CDR1 having the amino acid sequence of SEQ ID NO: 80;

(e) a light chain CDR2 having the amino acid sequence of SEQ ID NO: 81; and (f) a light chain CDR3 having the amino acid sequence of SEQ ID NO: 82; or selected from the group consisting of:

(a) a heavy chain CDR1 having the amino acid sequence of SEQ ID NO: 83;

(b) a heavy chain CDR2 having the amino acid sequence of SEQ ID NO: 84;

(c) a heavy chain CDR3 having the amino acid sequence of SEQ ID NO: 85;

(d) a light chain CDR1 having the amino acid sequence of SEQ ID NO: 86;

(e) a light chain CDR2 having the amino acid sequence of SEQ ID NO: 87; and (f) a light chain CDR3 having the amino acid sequence of SEQ ID NO: 88; or a conservative substitution variant of one or more of (a)-(f).

2. The antibody, antibody reagent, antigen-binding portion thereof, or CAR of paragraph 1, which comprises heavy chain CDRs having the amino acid sequences of SEQ ID NOs: 23-25, or 29-31, or 35-37, or 41-43, or 47-49, or 53-55, or 59-61, or 65-67, or 71-73, or 77-79, or 83-85, or a conservative substitution variant of such amino acid sequence.

3. The antibody, antibody reagent, antigen-binding portion thereof, or CAR of any of paragraphs 1-2, which comprises light chain CDRs having the amino acid sequences of SEQ ID NOs: 26-28, or 32-34, or 38-40, or 44-46, or 50-52, or 56-58, or 62-64, or 68-70, or 74-76, or 80-82, or 86-88, or a conservative substitution variant of such amino acid sequence.

4. The antibody, antibody reagent, antigen-binding portion thereof, or CAR of any of paragraphs 1-3, which comprises:

heavy chain CDRs having the amino acid sequences of SEQ ID NOs: 23-25 and light chain CDRs having the amino acid sequences of SEQ ID NOs: 26-28 or a conservative substitution variant of such amino acid sequence; or heavy chain CDRs having the amino acid sequences of SEQ ID NOs: 29-31 and light chain CDRs having the amino acid sequences of SEQ ID NOs: 32-34 or a conservative substitution variant of such amino acid sequence; or heavy chain CDRs having the amino acid sequences of SEQ ID NOs: 35-37 and light chain CDRs having the amino acid sequences of SEQ ID NOs: 38-40 or a conservative substitution variant of such amino acid sequence; or heavy chain CDRs having the amino acid sequences of SEQ ID NOs: 41-43 and light chain CDRs having the amino acid sequences of SEQ ID NOs: 44-46 or a conservative substitution variant of such amino acid sequence; or heavy chain CDRs having the amino acid sequences of SEQ ID NOs: 47-49 and light chain CDRs having the amino acid sequences of SEQ ID NOs: 50-52 or a conservative substitution variant of such amino acid sequence; or heavy chain CDRs having the amino acid sequences of SEQ ID NOs: 53-55 and light chain CDRs having the amino acid sequences of SEQ ID NOs: 56-58 or a conservative substitution variant of such amino acid sequence; or heavy chain CDRs having the amino acid sequences of SEQ ID NOs: 59-61 and light chain CDRs having the amino acid sequences of SEQ ID NOs: 62-64 or a conservative substitution variant of such amino acid sequence; or heavy chain CDRs having the amino acid sequences of SEQ ID NOs: 65-67 and light chain CDRs having the amino acid sequences of SEQ ID NOs: 68-70 or a conservative substitution variant of such amino acid sequence; or heavy chain CDRs having the amino acid sequences of SEQ ID NOs: 71-73 and light chain CDRs having the amino acid sequences of SEQ ID NOs: 74-76 or a conservative substitution variant of such amino acid sequence; or heavy chain CDRs having the amino acid sequences of SEQ ID NOs: 77-79 and light chain CDRs having the amino acid sequences of SEQ ID NOs: 80-82 or a conservative substitution variant of such amino acid sequence; or heavy chain CDRs having the amino acid sequences of SEQ ID NOs: 83-85 and light chain CDRs having the amino acid sequences of SEQ ID NOs: 86-88 or a conservative substitution variant of such amino acid sequence.

5. A first antibody, antibody reagent, antigen-binding portion thereof, or CAR that specifically binds an PD1 polypeptide, and can compete for binding of PD1 with a second antibody comprising:

heavy chain CDRs having the amino acid sequences of SEQ ID NOs: 23-25 and heavy chain CDRs having the amino acid sequences of SEQ ID NOs: 26-28 or a conservative substitution variant of such amino acid sequence; or heavy chain CDRs having the amino acid sequences of SEQ ID NOs: 29-31 and light chain CDRs having the amino acid sequences of SEQ ID NOs: 32-34 or a conservative substitution variant of such amino acid sequence; or heavy chain CDRs having the amino acid sequences of SEQ ID NOs: 35-37 and light chain CDRs having the amino acid sequences of SEQ ID NOs: 38-40 or a conservative substitution variant of such amino acid sequence; or heavy chain CDRs having the amino acid sequences of SEQ ID NOs: 41-43 and light chain CDRs having the amino acid sequences of SEQ ID NOs: 44-46 or a conservative substitution variant of such amino acid sequence; or heavy chain CDRs having the amino acid sequences of SEQ ID NOs: 47-49 and light chain CDRs having the amino acid sequences of SEQ ID NOs: 50-52 or a conservative substitution variant of such amino acid sequence; or heavy chain CDRs having the amino acid sequences of SEQ ID NOs: 53-55 and light chain CDRs having the amino acid sequences of SEQ ID NOs: 56-58 or a conservative substitution variant of such amino acid sequence; or heavy chain CDRs having the amino acid sequences of SEQ ID NOs: 59-61 and light chain CDRs having the amino acid sequences of SEQ ID NOs: 62-64 or a conservative substitution variant of such amino acid sequence; or heavy chain CDRs having the amino acid sequences of SEQ ID NOs: 65-67 and light chain CDRs having the amino acid sequences of SEQ ID NOs: 68-70 or a conservative substitution variant of such amino acid sequence; or heavy chain CDRs having the amino acid sequences of SEQ ID NOs: 71-73 and light chain CDRs having the amino acid sequences of SEQ ID NOs: 74-76 or a conservative substitution variant of such amino acid sequence; or heavy chain CDRs having the amino acid sequences of SEQ ID NOs: 77-79 and light chain CDRs having the amino acid sequences of SEQ ID NOs: 80-82 or a conservative substitution variant of such amino acid sequence; or heavy chain CDRs having the amino acid sequences of SEQ ID NOs: 83-85 and light chain CDRs having the amino acid sequences of SEQ ID NOs: 86-88 or a conservative substitution variant of such amino acid sequence.

6. The first antibody, antibody reagent, antigen-binding fragment thereof, or chimaeric antigen receptor (CAR) of paragraph 5, comprising at least one heavy or light chain complementarity determining region (CDR) selected from the group consisting of:

(a) a heavy chain CDR1 having the amino acid sequence of SEQ ID NO: 23;

(b) a heavy chain CDR2 having the amino acid sequence of SEQ ID NO: 24;

(c) a heavy chain CDR3 having the amino acid sequence of SEQ ID NO: 25;

(d) a light chain CDR1 having the amino acid sequence of SEQ ID NO: 26;

(e) a light chain CDR2 having the amino acid sequence of SEQ ID NO: 27; and (f) a light chain CDR3 having the amino acid sequence of SEQ ID NO: 28; or selected from the group consisting of:

(a) a heavy chain CDR1 having the amino acid sequence of SEQ ID NO: 29;

(b) a heavy chain CDR2 having the amino acid sequence of SEQ ID NO: 30;

(c) a heavy chain CDR3 having the amino acid sequence of SEQ ID NO: 31;

(d) a light chain CDR1 having the amino acid sequence of SEQ ID NO: 32;

(e) a light chain CDR2 having the amino acid sequence of SEQ ID NO: 33; and (f) a light chain CDR3 having the amino acid sequence of SEQ ID NO: 34; or selected from the group consisting of:

(a) a heavy chain CDR1 having the amino acid sequence of SEQ ID NO: 35;

(b) a heavy chain CDR2 having the amino acid sequence of SEQ ID NO: 36;

(c) a heavy chain CDR3 having the amino acid sequence of SEQ ID NO: 37;

(d) a light chain CDR1 having the amino acid sequence of SEQ ID NO: 38;

(e) a light chain CDR2 having the amino acid sequence of SEQ ID NO: 39; and (f) a light chain CDR3 having the amino acid sequence of SEQ ID NO: 40; or selected from the group consisting of:

(a) a heavy chain CDR1 having the amino acid sequence of SEQ ID NO: 41;

(b) a heavy chain CDR2 having the amino acid sequence of SEQ ID NO: 42;

(c) a heavy chain CDR3 having the amino acid sequence of SEQ ID NO: 43;

(d) a light chain CDR1 having the amino acid sequence of SEQ ID NO: 44;

(e) a light chain CDR2 having the amino acid sequence of SEQ ID NO: 45; and (f) a light chain CDR3 having the amino acid sequence of SEQ ID NO: 46; or selected from the group consisting of:

(a) a heavy chain CDR1 having the amino acid sequence of SEQ ID NO: 47;

(b) a heavy chain CDR2 having the amino acid sequence of SEQ ID NO: 48;

(c) a heavy chain CDR3 having the amino acid sequence of SEQ ID NO: 49;

(d) a light chain CDR1 having the amino acid sequence of SEQ ID NO: 50;

(e) a light chain CDR2 having the amino acid sequence of SEQ ID NO: 51; and (f) a light chain CDR3 having the amino acid sequence of SEQ ID NO: 52; or selected from the group consisting of:

(a) a heavy chain CDR1 having the amino acid sequence of SEQ ID NO: 53;

(b) a heavy chain CDR2 having the amino acid sequence of SEQ ID NO: 54;

(c) a heavy chain CDR3 having the amino acid sequence of SEQ ID NO: 55;

(d) a light chain CDR1 having the amino acid sequence of SEQ ID NO: 56;

(e) a light chain CDR2 having the amino acid sequence of SEQ ID NO: 57; and (f) a light chain CDR3 having the amino acid sequence of SEQ ID NO: 58; or selected from the group consisting of:

(a) a heavy chain CDR1 having the amino acid sequence of SEQ ID NO: 59;

(b) a heavy chain CDR2 having the amino acid sequence of SEQ ID NO: 60;

(c) a heavy chain CDR3 having the amino acid sequence of SEQ ID NO: 61;

(d) a light chain CDR1 having the amino acid sequence of SEQ ID NO: 62;

(e) a light chain CDR2 having the amino acid sequence of SEQ ID NO: 63; and (f) a light chain CDR3 having the amino acid sequence of SEQ ID NO: 64; or selected from the group consisting of:

(a) a heavy chain CDR1 having the amino acid sequence of SEQ ID NO: 65;

(b) a heavy chain CDR2 having the amino acid sequence of SEQ ID NO: 66;

(c) a heavy chain CDR3 having the amino acid sequence of SEQ ID NO: 67;

(d) a light chain CDR1 having the amino acid sequence of SEQ ID NO: 68;

(e) a light chain CDR2 having the amino acid sequence of SEQ ID NO: 69; and (f) a light chain CDR3 having the amino acid sequence of SEQ ID NO: 70; or selected from the group consisting of:

(a) a heavy chain CDR1 having the amino acid sequence of SEQ ID NO: 71;

(b) a heavy chain CDR2 having the amino acid sequence of SEQ ID NO: 72;

(c) a heavy chain CDR3 having the amino acid sequence of SEQ ID NO: 73;

(d) a light chain CDR1 having the amino acid sequence of SEQ ID NO: 74;

(e) a light chain CDR2 having the amino acid sequence of SEQ ID NO: 75; and (f) a light chain CDR3 having the amino acid sequence of SEQ ID NO: 76; or selected from the group consisting of:

(a) a heavy chain CDR1 having the amino acid sequence of SEQ ID NO: 77;

(b) a heavy chain CDR2 having the amino acid sequence of SEQ ID NO: 78;

(c) a heavy chain CDR3 having the amino acid sequence of SEQ ID NO: 79;

(d) a light chain CDR1 having the amino acid sequence of SEQ ID NO: 80;

(e) a light chain CDR2 having the amino acid sequence of SEQ ID NO: 81; and (f) a light chain CDR3 having the amino acid sequence of SEQ ID NO: 82; or selected from the group consisting of:

(a) a heavy chain CDR1 having the amino acid sequence of SEQ ID NO: 83;

(b) a heavy chain CDR2 having the amino acid sequence of SEQ ID NO: 84;

(c) a heavy chain CDR3 having the amino acid sequence of SEQ ID NO: 85;

(d) a light chain CDR1 having the amino acid sequence of SEQ ID NO: 86;

(e) a light chain CDR2 having the amino acid sequence of SEQ ID NO: 87; and (f) a light chain CDR3 having the amino acid sequence of SEQ ID NO: 88; or a conservative substitution variant of one or more of (a)-(f).

7. The antibody, antibody reagent, antigen-binding portion thereof, or CAR of paragraph 5 or 6, which comprises heavy chain CDRs having the amino acid sequences of SEQ ID NOs: 23-25, or 29-31, or 35-37, or 41-43, or 47-49, or 53-55, or 59-61, or 65-67, or 71-73, or 77-79, or 83-85, or a conservative substitution variant of such amino acid sequence.

8. The antibody, antibody reagent, antigen-binding portion thereof, or CAR of any of paragraphs 5-7, which comprises light chain CDRs having the amino acid sequences of SEQ ID NOs: 26-28, or 32-34, or 38-40, or 44-46, or 50-52, or 56-58, or 62-64, or 68-70, or 74-76, or 80-82, or 86-88, or a conservative substitution variant of such amino acid sequence.

9. The antibody, antibody reagent, antigen-binding portion thereof, or CAR of any of paragraphs 5-8, which comprises:

heavy chain CDRs having the amino acid sequences of SEQ ID NOs: 23-25 and light chain CDRs having the amino acid sequences of SEQ ID NOs: 26-28 or a conservative substitution variant of such amino acid sequence; or heavy chain CDRs having the amino acid sequences of SEQ ID NOs: 29-31 and light chain CDRs having the amino acid sequences of SEQ ID NOs: 32-34 or a conservative substitution variant of such amino acid sequence; or heavy chain CDRs having the amino acid sequences of SEQ ID NOs: 35-37 and light chain CDRs having the amino acid sequences of SEQ ID NOs: 38-40 or a conservative substitution variant of such amino acid sequence; or heavy chain CDRs having the amino acid sequences of SEQ ID NOs: 41-43 and light chain CDRs having the amino acid sequences of SEQ ID NOs: 44-46 or a conservative substitution variant of such amino acid sequence; or heavy chain CDRs having the amino acid sequences of SEQ ID NOs: 47-49 and light chain CDRs having the amino acid sequences of SEQ ID NOs: 50-52 or a conservative substitution variant of such amino acid sequence; or heavy chain CDRs having the amino acid sequences of SEQ ID NOs: 53-55 and light chain CDRs having the amino acid sequences of SEQ ID NOs: 56-58 or a conservative substitution variant of such amino acid sequence; or heavy chain CDRs having the amino acid sequences of SEQ ID NOs: 59-61 and light chain CDRs having the amino acid sequences of SEQ ID NOs: 62-64 or a conservative substitution variant of such amino acid sequence; or heavy chain CDRs having the amino acid sequences of SEQ ID NOs: 65-67 and light chain CDRs having the amino acid sequences of SEQ ID NOs: 68-70 or a conservative substitution variant of such amino acid sequence; or heavy chain CDRs having the amino acid sequences of SEQ ID NOs: 71-73 and light chain CDRs having the amino acid sequences of SEQ ID NOs: 74-76 or a conservative substitution variant of such amino acid sequence; or heavy chain CDRs having the amino acid sequences of SEQ ID NOs: 77-79 and light chain CDRs having the amino acid sequences of SEQ ID NOs: 80-82 or a conservative substitution variant of such amino acid sequence; or heavy chain CDRs having the amino acid sequences of SEQ ID NOs: 83-85 and light chain CDRs having the amino acid sequences of SEQ ID NOs: 86-88 or a conservative substitution variant of such amino acid sequence.

10. The antibody, antibody reagent, antigen-binding portion thereof, or CAR of any of paragraphs 1-9, comprising the heavy chain sequence of any of SEQ ID NOs: 1, 3, 5, 7, 9, 11, 13, 15, 17, 19 or 21.

11. The antibody, antibody reagent, antigen-binding portion thereof, or CAR of any of paragraphs 1-10, comprising the light chain sequence of any of SEQ ID NOs: 2, 4, 6, 8, 10, 12, 14, 16, 18, 20, or 22.

12. The antibody, antibody reagent, antigen-binding portion thereof, or CAR of any of paragraphs 1-11, comprising:

the heavy chain sequence of SEQ ID NO: 1 and the light chain sequence of SEQ ID NO: 2; or the heavy chain sequence of SEQ ID NO: 3 and the light chain sequence of SEQ ID NO: 4; or the heavy chain sequence of SEQ ID NO: 5 and the light chain sequence of SEQ ID NO: 6; or the heavy chain sequence of SEQ ID NO: 7 and the light chain sequence of SEQ ID NO: 8; or the heavy chain sequence of SEQ ID NO: 9 and the light chain sequence of SEQ ID NO: 10; or the heavy chain sequence of SEQ ID NO: 11 and the light chain sequence of SEQ ID NO: 12; or the heavy chain sequence of SEQ ID NO: 13 and the light chain sequence of SEQ ID NO: 14; or the heavy chain sequence of SEQ ID NO: 15 and the light chain sequence of SEQ ID NO: 16; or the heavy chain sequence of SEQ ID NO: 17 and the light chain sequence of SEQ ID NO: 18; or the heavy chain sequence of SEQ ID NO: 19 and the light chain sequence of SEQ ID NO: 20; or the heavy chain sequence of SEQ ID NO: 21 and the light chain sequence of SEQ ID NO: 22.

13. The antibody, antibody reagent, antigen-binding portion thereof, or CAR of any of paragraphs 1-12, further comprising a conservative substitution in a sequence not comprised by a CDR.

14. The antibody, antibody reagent, antigen-binding portion thereof, or CAR of any of paragraphs 1-13, wherein the antibody reagent or antigen-binding fragment thereof is fully human or fully humanized.

15. The antibody, antibody reagent, antigen-binding portion thereof, or CAR of any of paragraphs 1-14, wherein the antibody reagent or antigen-binding fragment thereof is fully humanized except for the CDR sequences.

16. The antibody, antibody reagent, antigen-binding portion thereof, or CAR of any of paragraphs 1-15, wherein the reagent or fragment is selected from the group consisting of:

an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

17. A composition comprising the antibody, antibody reagent, antigen-binding portion thereof, or CAR of any one of paragraphs 1-16, and a chemotherapeutic agent.

18. The composition of paragraph 17, wherein the antibody, antibody reagent, or antigen-binding portion thereof is conjugated to the chemotherapeutic agent.

19. A nucleic acid sequence encoding the antibody, antibody reagent, antigen-binding fragment thereof, or CAR of any of paragraphs 1-16.

20. A cell comprising the antibody, antibody reagent, antigen-binding fragment thereof, or CAR of any of paragraphs 1-16 or the nucleic acid sequence of paragraph 19.

21. A pharmaceutical composition comprising the antibody, antibody reagent, antigen-binding fragment thereof, or CAR of any of paragraphs 1-16; or the composition of any of paragraphs 17-18; or the cell of paragraph 20, and a pharmaceutically acceptable carrier.

22. A solid support comprising the antibody, antibody reagent, antigen-binding fragment thereof, or CAR of any of paragraphs 1-16.

23. The solid support of paragraph 22, wherein the antibody, antibody reagent or antigen-binding fragment thereof is detectably labeled.

24. The solid support of any of paragraphs 22-23, wherein the solid support comprises a particle, a bead, a polymer, or a substrate.

25. A kit for the detection of PD1 polypeptide in a sample, the kit comprising at least a first antibody, antibody reagent, antigen-binding fragment thereof, or CAR of any of paragraphs 1-16 immobilized on a solid support and comprising a detectable label.

26. A molecular complex comprising at least one antibody, antibody reagent, antigen-binding fragment thereof, or CAR of any of paragraphs 1-16 bound to an PD1 polypeptide.

27. A method of treating cancer in a subject in need thereof, the method comprising administering the antibody, antibody reagent, antigen-binding fragment thereof, or CAR of any of paragraphs 1-16; or the composition of any of paragraphs 17-18; or the cell of paragraph 20, to the subject.

28. The method of paragraph 27, wherein the cancer is selected from the group consisting of: Non-small cell lung cancer; melanoma; metastatic melanoma; renal cell carcinoma; squamous cell carcinoma of the head and neck; Hodgkin lymphoma; classical Hodgkin lymphoma; and urothelial carcinoma.

29. The antibody, antibody reagent, antigen-binding fragment thereof, or CAR of any of paragraphs 1-16; or the composition of any of paragraphs 17-18; or the cell of paragraph 20, for use in a method of treating cancer in a subject in need thereof.

30. The composition of paragraph 29, wherein the cancer is selected from the group consisting of Non-small cell lung cancer; melanoma; metastatic melanoma; renal cell carcinoma; squamous cell carcinoma of the head and neck; Hodgkin lymphoma; classical Hodgkin lymphoma; and urothelial carcinoma.

EXAMPLES

Example 1

The efficacy of therapeutic antibodies is dependent on their binding affinity and specificity toward target antigens. Some therapeutic antibodies developed with currently available technology have not been optimized for these critical parameters. The antibodies described herein were developed with technology designed to address this issue. Briefly, the immunoglobulin genes encoding a specific therapeutic antibody are introduced into the mouse immunoglobulin locus. During B cell maturation, the original human antibody is diversified extensively by V(D)J recombination to form a large repertoire of primary mouse B cells in which many of which express a different variant of the original antibodies. The animals are immunized with a target antigen to select for and expand B cells expressing the best binder for the antigen. During immune response, the human antibody undergoes affinity maturation, a natural process of antibody optimization.

After repeated immunizations, the immunoglobulin genes encoding high affinity antibodies for the target antigen are isolated. This approach is demonstrated herein using an existing anti-PD1 antibody as an initial starting point to develop new, more effective antibodies. Previously, this antibody had proven to be effective in boosting T cell activity towards tumor cells. As demonstrated herein, the initial anti-PD1 antibody, when subjected to more affinity maturation, can be optimized for heavy chain CDR3 usage to gain higher affinity and increased specificity. To achieve this goal, the original anti-PD1 antibody was diversified in the described mouse system to create a much greater range of the CDR3 sequence which is often critical for antigen binding, exceeding the complexity achievable in any humanized mouse model. Members of this large set of anti-PD1-related antibodies underwent additional affinity maturation in response to immunization with PD1 antigen.

With this system, a large set of variants of the original anti-PD1 antibody were generated, and some of these variants differ substantially from the original antibody (up to 20% sequence divergence including novel CDR3 sequences). Based on preliminary analysis, at least some of these antibodies bind to PD1 with higher affinity and specificity than the original antibody (FIGS. 5 and 6).

Antibody sequences. The protein sequences of heavy chain (HC) and light chain (LC) for 11 antibodies are listed below:

```
319-8-2 Heavy Chain
                                          (SEQ ID NO: 1)
QVQLVESGGDVVQPGGSLRLSCAASGVAFSDSGMHWVRQAPGKGLEWLAVIWYDGSK

KHYAEAVKGRFTISRDNSKNMLYLQMNSLRVDDTAIYYCAKAHSQDDYWGQGTLVTV

SS 319-8-2 Light Chain
                                          (SEQ ID NO: 2)
EIVLTQSPATLSLSPGERATLSCRATPSIDSYLAWYQQKSGQSPRLIIHDASIRATGIPDRFS

GSGSGTDFTLTISSLEPEDFAVYYCQQRDSWPLAFGGGTKVEFK 319-9-17 Heavy Chain
                                          (SEQ ID NO: 3)
QEWLVESGGDVVQPGGSLRLSCATSKVTFNDFGIHWVRQAPGKGLEWVAIIWYDGSR

NHYADSVRGRFTLSRDNSKNMVHLHMSSLRTEDTAMYYCARGIHSNDDYWGQGTMV

TVSS 319-9-17 Light Chain
                                          (SEQ ID NO: 4)
EIVLTQSPATLSLSPGERATLSCRTSQSVSSDLAWFQQKPGQAPRLFIFDASKRVNGIPARF

SGSGSGTDFTLTISSLEPEDFAVYYCQQRTDWPLTFGGGSRVEIK
```

-continued 319-9-53 Heavy Chain
                                                        (SEQ ID NO: 5)
QVQLVESGGDVVQSGGSLRLSCAVSGVVFSDYGFEWVRQAPGKGLEWVAVIWYDGS

RKHYADSVQGRFTISRDNFRNMLYLQMTGLRVEDTAKYYCTRSHSHEDYWGQGTLVT

VSS 319-9-53 Light Chain
                                                        (SEQ ID NO: 6)
EIVLTQSPATLSLSPGERATLSCGASQNIDNSLAWFQQKPGQAPRLIIYDASKRATGIPAR

FSGSGSGTDFTLTISTLEPEDFAVYYCQQRDHWPLNFGGGTKVEVK 319-9-27 Heavy Chain
                                                        (SEQ ID NO: 7)
QVQLVESGGDVVQPGGSLRLSCAVSGVTFGDFGFEWVRQAPGKGLEWVAVIWYDGS

RKHYAESVRGRFTISRDNSRNMMYLEMTGLRVEDTAKYYCTRSHSHEDYWGQGTLVT

VSS 319-9-27 Light Chain
                                                        (SEQ ID NO: 8)
EIVLTQSPATLSLSPGERATLSCRASQSISNYLAWFQQKSGQAPRLIIHDAFKRAAGIPTR

FSGSGSGTDFTLTISSLEPEDFAVYYCQQRDNWPLNFGGGTKVEIK 397-27-93 Heavy Chain
                                                        (SEQ ID NO: 9)
QVQLVESGGDVVQPGGSLRLSCAASGVVFSDYGLYWVRQAPGKGLEWVALIWYDGS

KKFYADSVKGRFSISRDNSKNMLYLQMNNLRADDSAIYYCSRGIRQGPWFAYWGQG

TRVTVSP 397-27-93 Light Chain
                                                        (SEQ ID NO: 10)
EIVLTQSPATLSLSPGERATLSCRASQSISSDLTWFQQKPGQAPRLIIYDASNRATGIPARFS

GSGSGTDFTLTISSLEPEDFVVYYCLQRSDWPLTFGGGTKVEIK 319-9-34 Heavy Chain
                                                        (SEQ ID NO: 11)
QVQLVESGGDVVQPGGSLRLSCTVSGAVFRDLGMEWVRQAPGKGLEWLAVIWYDGGR

KHYADSVKGRFTISRDNSRNMLFLQMNGLRVDDTAMYYCTRSHSTDDYWGQGTLVTV

SS 319-9-34 Light Chain
                                                        (SEQ ID NO: 12)
EIVLTQSPATLSVSPGERATLSCRASQSISSDLAWFQQKPGQAPRLIIHGASKRATGIPARF

SGSGSGTDFTLTISSLEPEDFAVYYCQQRDSWPLNFGGGTKVEIK 397-27-23 Heavy Chain
                                                        (SEQ ID NO: 13)
QVQLVESGGDVVQPGGSLRLSCSASGLVISDYGMNWVRQAPGKGLEWVGLIWYDGSK

KYYSDFVKGRFTISRDNSKNILYLQMNNLRAEDTAMYYCARFLIGATRRGNAMDYWGQ

GTSVTVSS 397-27-23 Light Chain
                                                        (SEQ ID NO: 14)
EVVLTQSPATLSLSPGERATLSCRASQSIDSDLAWSQQKPGQPPRLIIYDASNRATGIPARF

SGSGSGTDFTLTISSLEPEDFAVYYCQQRSDWPLTFGGGTKVEIR 397-27-3 Heavy Chain
                                                        (SEQ ID NO: 15)
QVQLVESGGDVVQPGGSLRLSCSASGLVFRDYGMNWVRQAPGKGLEWVGLIWYDGTK

KYYSDFVKGRFTISRDNSKNMLYLQMNNLRAEDTAIYYCARFLIGATRRGNAMDYWGQ

GTSVIVSS

-continued 397-27-3 Light Chain
(SEQ ID NO: 16)
EVVLTQSPATLSLSPGERATLSCRASQSIDSDLAWSQQKTGQPPRLIIYDASNRATGIPARF

SGSGSGTDFTLTISSLEPEDFAVYYCQQRSDWPLTFGGGTKVEIR 397-9-75 Heavy Chain
(SEQ ID NO: 17)
QLQLVESGGDVVQPGGSLRLSCAASGVVFSDFGLEWVRQAPGKGLEWLAVIWYDGSRK

HYADSVKGRFTISRDNSKNMLYLQMNSLRVEDTAMYYCARCHSKEDYWGQGTLVTVSS 397-9-75 Light Chain
(SEQ ID NO: 18)
EIEVTQSPATLSLSPGERATLSCRASQSIDTDLAWFQQRPGQTPRLIIYDASKRATGIPAR

FSGGGSGTDFTLTISSLEPEDFAVYYCQQRTTWPLTFGGGTKVEIK 397-27-35 Heavy Chain
(SEQ ID NO: 19)
QVQLVESGGDVVQPGGSLRLSCSASGLVISDYGMNWVRQAPGKGLEWVGLIWYDGSK

KYYSDFVKGRFTISRDNSKNILYLQMNNLRAEDTAMYYCARFLIGATRRGNAMDYWGQ

GTSVTVSS 397-27-35 Light Chain
(SEQ ID NO: 20)
EVVLTQSPATLSLSPGERATLSCRASQSIDSDLAWSQQKPGQPPRLIIYDASNRATGIPA

RFSGSGSGTDFTLTISSLEDEDFAVYYCQQRSDWPLTFGGGTKVEIR 397-27-37 Heavy Chain
(SEQ ID NO: 21)
QVQLVESGGDVVQPGGSLRLSCAASGVAFRNYGMHWVRQAPGKGLEWVAIIWYDG

SNKYYADSVKGRFTISRDNSKNMLYLQMNSLRAEDTAMYYCARLSIGTTHYFDTDDY

WGQGTSVTVSS 397-27-37 Light Chain
(SEQ ID NO: 22)
EIVLTQSPATLSLSPGERATLSCRASQSVSSYLAWYQQKVGQAPRLIIFDASNRATGIPA

RFSGSGSGTDFTLTITSLDPEDFAVYYCQQRSAWPLTFGGGTKVEIR

TABLE 1

|  | Sequence | SEQ ID NO |
| --- | --- | --- |
| Antibody: 319-8-2 | | |
| Heavy Chain CDR1 | GVAFSDSG | 23 |
| Heavy Chain CDR2 | IWYDGSKK | 24 |
| Heavy Chain CDR3 | AKAHSQDDY | 25 |
| Light Chain CDR1 | PSIDSY | 26 |
| Light Chain CDR2 | DAS | |
| Light Chain CDR3 | QQRDSWPLA | 28 |
| Antibody: 319-8-17 | | |
| Heavy Chain CDR1 | KVTFNDFG | 29 |
| Heavy Chain CDR2 | IWYDGSRN | 30 |
| Heavy Chain CDR3 | ARGIHSNDDY | 31 |
| Light Chain CDR1 | QSVSSD | 32 |
| Light Chain CDR2 | DAS | |
| Light Chain CDR3 | QQRTDWPLT | 34 |
| Antibody: 319-9-53 | | |
| Heavy Chain CDR1 | GVVFSDYG | 35 |
| Heavy Chain CDR2 | IWYDGSRK | 36 |
| Heavy Chain CDR3 | TRSHSHEDY | 37 |
| Light Chain CDR1 | QNIDNS | 38 |
| Light Chain CDR2 | DAS | |
| Light Chain CDR3 | QQRDHWPLN | 40 |

TABLE 1-continued

|  | Sequence | SEQ ID NO |
| --- | --- | --- |
| Antibody: 319-9-27 | | |
| Heavy Chain CDR1 | GVTFGDFG | 41 |
| Heavy Chain CDR2 | IWYDGSRK | 42 |
| Heavy Chain CDR3 | TRSHSHEDY | 43 |
| Light Chain CDR1 | QSISNY | 44 |
| Light Chain CDR2 | DAF | |
| Light Chain CDR3 | QQRDNWPLN | 46 |
| Antibody: 319-27-93 | | |
| Heavy Chain CDR1 | GVVFSDYG | 47 |
| Heavy Chain CDR2 | IWYDGSKK | 48 |
| Heavy Chain CDR3 | SRGIRQGPWFAY | 49 |
| Light Chain CDR1 | QSISSD | 50 |
| Light Chain CDR2 | DAS | |
| Light Chain CDR3 | LQRSDWPLT | 52 |
| Antibody: 319-9-34 | | |
| Heavy Chain CDR1 | GAVFRDLG | 53 |
| Heavy Chain CDR2 | IWYDGGRK | 54 |
| Heavy Chain CDR3 | TRSHSTDDY | 55 |
| Light Chain CDR1 | QSISSD | 56 |
| Light Chain CDR2 | GAS | |
| Light Chain CDR3 | QQRDSWPLN | 58 |

TABLE 1-continued

|  | Sequence | SEQ ID NO |
|---|---|---|
| Antibody: 319-27-23 | | |
| Heavy Chain CDR1 | GLVISDYG | 59 |
| Heavy Chain CDR2 | IWYDGSKK | 60 |
| Heavy Chain CDR3 | ARFLIGATRRGNAMDY | 61 |
| Light Chain CDR1 | QSIDSD | 62 |
| Light Chain CDR2 | DAS | |
| Light Chain CDR3 | QQRSDWPLT | 64 |
| Antibody: 319-27-3 | | |
| Heavy Chain CDR1 | GLVFRDYG | 65 |
| Heavy Chain CDR2 | IWYDGTKK | 66 |
| Heavy Chain CDR3 | ARFLIGATRRGNAMDY | 67 |
| Light Chain CDR1 | QSIDSD | 68 |
| Light Chain CDR2 | DAS | |
| Light Chain CDR3 | QQRSDWPLT | 70 |
| Antibody: 319-9-75 | | |
| Heavy Chain CDR1 | GVVFSDFG | 71 |
| Heavy Chain CDR2 | IWYDGSRK | 72 |
| Heavy Chain CDR3 | ARCHSKEDY | 73 |

TABLE 1-continued

|  | Sequence | SEQ ID NO |
|---|---|---|
| Light Chain CDR1 | QSIDTD | 74 |
| Light Chain CDR2 | DAS | |
| Light Chain CDR3 | QQRTTWPLT | 76 |
| Antibody: 319-27-35 | | |
| Heavy Chain CDR1 | GLVISDYG | 77 |
| Heavy Chain CDR2 | IWYDGSKK | 78 |
| Heavy Chain CDR3 | ARFLIGATRRGNAMDY | 79 |
| Light Chain CDR1 | QSIDSD | 80 |
| Light Chain CDR2 | DAS | |
| Light Chain CDR3 | QQRSDWPLT | 82 |
| Antibody: 319-27-37 | | |
| Heavy Chain CDR1 | GVAFRNYG | 83 |
| Heavy Chain CDR2 | IWYDGSNK | 84 |
| Heavy Chain CDR3 | ARLSIGTTHYFDTDDY | 85 |
| Light Chain CDR1 | QSVSSY | 86 |
| Light Chain CDR2 | DAS | |
| Light Chain CDR3 | QQRSAWPLT | 88 |

What is claimed herein is:

1. A nucleic acid sequence encoding an antibody, antibody reagent, antigen-binding fragment thereof, or chimaeric antigen receptor (CAR), that specifically binds an PD1 polypeptide, said antibody reagent, antigen-binding portion thereof, or CAR comprising:

heavy chain complementarity determining regions (CDRs) having the amino acid sequences of SEQ ID NOs: 23-25 and light chain CDRs having the amino acid sequences of SEQ ID NO: 26, DAS and SEQ ID NO: 28; or heavy chain CDRs having the amino acid sequences of SEQ ID NOs: 29-31 and light chain CDRs having the amino acid sequences of SEQ ID NO: 32, DAS and SEQ ID NO: 34; or heavy chain CDRs having the amino acid sequences of SEQ ID NOs: 35-37 and light chain CDRs having the amino acid sequences of SEQ ID NO: 38, DAS and SEQ ID NO: 40; or heavy chain CDRs having the amino acid sequences of SEQ ID NOs: 41-43 and light chain CDRs having the amino acid sequences of SEQ ID NO: 44, DAF and SEQ ID NO:46; or heavy chain CDRs having the amino acid sequences of SEQ ID NOs: 47-49 and light chain CDRs having the amino acid sequences of SEQ ID NO: 50, DAS and SEQ ID NO: 52; or heavy chain CDRs having the amino acid sequences of SEQ ID NOs: 53-55 and light chain CDRs having the amino acid sequences of SEQ ID NO: 56, GAS and SEQ ID NO: 58; or heavy chain CDRs having the amino acid sequences of SEQ ID NOs: 59-61 and light chain CDRs having the amino acid sequences of SEQ ID NO: 62, DAS and SEQ ID NO: 64; or heavy chain CDRs having the amino acid sequences of SEQ ID NOs: 65-67 and light chain CDRs having the amino acid sequences of SEQ ID NO: 68, DAS and SEQ ID NO: 70; or heavy chain CDRs having the amino acid sequences of SEQ ID NOs: 71-73 and light chain CDRs having the amino acid sequences of SEQ ID NO: 74, DAS and SEQ ID NO: 76; or heavy chain CDRs having the amino acid sequences of SEQ ID NOs: 77-79 and light chain CDRs having the amino acid sequences of SEQ ID NO: 80, DAS and SEQ ID NO: 82; or heavy chain CDRs having the amino acid sequences of SEQ ID NOs: 83-85 and light chain CDRs having the amino acid sequences of SEQ ID NO: 86, DAS and SEQ ID NO: 88.

2. The nucleic acid of claim 1, wherein the antibody, antibody reagent, antigen-binding portion thereof, or CAR comprises the heavy chain sequence of any of SEQ ID NOs: 1, 3, 5, 7, 9, 11, 13, 15, 17, 19 or 21.

3. The nucleic acid of claim 1, wherein the antibody, antibody reagent, antigen-binding portion thereof, or CAR comprises the light chain sequence of any of SEQ ID NOs: 2, 4, 6, 8, 10, 12, 14, 16, 18, 20, or 22.

4. The nucleic acid of claim 1, wherein the antibody, antibody reagent, antigen-binding portion thereof, or CAR comprises:

the heavy chain sequence of SEQ ID NO: 1 and the light chain sequence of SEQ ID NO: 2; or the heavy chain sequence of SEQ ID NO: 3 and the light chain sequence of SEQ ID NO: 4; or the heavy chain sequence of SEQ ID NO: 5 and the light chain sequence of SEQ ID NO: 6; or the heavy chain sequence of SEQ ID NO: 7 and the light chain sequence of SEQ ID NO: 8; or the heavy chain sequence of SEQ ID NO: 9 and the light chain sequence of SEQ ID NO: 10; or the heavy chain sequence of SEQ ID NO: 11 and the light chain sequence of SEQ ID NO: 12; or the heavy chain sequence of SEQ ID NO: 13 and the light chain sequence of SEQ ID NO: 14; or the heavy chain sequence of SEQ ID NO: 15 and the light chain sequence of SEQ ID NO: 16; or the heavy chain sequence of SEQ ID NO: 17 and the light chain sequence of SEQ ID NO: 18; or the heavy chain sequence of SEQ ID NO: 19 and the light chain sequence of SEQ ID NO: 20; or the heavy chain sequence of SEQ ID NO: 21 and the light chain sequence of SEQ ID NO: 22.

5. The nucleic acid of claim 1, wherein the antibody, antibody reagent, antigen-binding portion thereof, or CAR further comprises a conservative substitution in a sequence not comprised by a CDR.

6. The nucleic acid of claim 1, wherein the antibody, antibody reagent, antigen-binding portion thereof, or CAR is fully human or fully humanized.

7. The nucleic acid of claim 1, wherein the antibody, antibody reagent, antigen-binding portion thereof, or CAR is fully humanized except for the CDR sequences.

8. The nucleic acid of claim 1, wherein the antibody, antibody reagent, antigen-binding portion thereof, or CAR is selected from the group consisting of:

an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a diabody, a multispecific antibody, a dual specific antibody, an anti-idiotypic antibody, and a bispecific antibody.

9. A cell comprising an antibody, antibody reagent, antigen-binding fragment thereof, or chimaeric antigen receptor (CAR), that specifically binds an PD1 polypeptide, said antibody reagent, antigen-binding portion thereof, or CAR is encoded by a nucleic acid sequence of claim 1.

10. A solid support comprising an antibody, antibody reagent, or antigen-binding fragment thereof, that specifically binds an PD1 polypeptide, said antibody reagent, or antigen-binding portion thereof is encoded by a nucleic acid sequence of claim 1.

11. The solid support of claim 10, wherein the antibody, antibody reagent or antigen-binding fragment thereof is detectably labeled.

12. The solid support of claim 10, wherein the solid support comprises a particle, a bead, a polymer, or a substrate.

13. A kit for the detection of PD1 polypeptide in a sample, the kit comprising a solid support of claim 10.

14. The nucleic acid sequence of claim 1, wherein the antibody reagent, antigen-binding portion thereof, or CAR comprises:

heavy chain CDRs having the amino acid sequences of SEQ ID NOs: 23-25 and light chain CDRs having the amino acid sequences of SEQ ID NO: 26, DAS and SEQ ID NO: 28; or heavy chain CDRs having the amino acid sequences of SEQ ID NOs: 29-31 and light chain CDRs having the amino acid sequences of SEQ ID NO: 32, DAS and SEQ ID NO: 34; or heavy chain CDRs having the amino acid sequences of SEQ ID NOs: 35-37 and light chain CDRs having the amino acid sequences of SEQ ID NO: 38, DAS and SEQ ID NO: 40; or heavy chain CDRs having the amino acid sequences of SEQ ID NOs: 41-43 and light chain CDRs having the amino acid sequences of SEQ ID NO: 44, DAF and SEQ ID NO:46; or heavy chain CDRs having the amino acid sequences of SEQ ID NOs: 47-49 and light chain CDRs having the amino acid sequences of SEQ ID NO: 50, DAS and SEQ ID NO: 52; or heavy chain CDRs having the amino acid sequences of SEQ ID NOs: 59-61 and light chain CDRs having the amino acid sequences of SEQ ID NO: 62, DAS and SEQ ID NO: 64; or heavy chain CDRs having the amino acid sequences of SEQ ID NOs: 65-67 and light chain CDRs having the amino acid sequences of SEQ ID NO: 68, DAS and SEQ ID NO: 70; or heavy chain CDRs having the amino acid sequences of SEQ ID NOs: 71-73 and light chain CDRs having the amino acid sequences of SEQ ID NO: 74, DAS and SEQ ID NO: 76; or heavy chain CDRs having the amino acid sequences of SEQ ID NOs: 77-79 and light chain CDRs having the amino acid sequences of SEQ ID NO: 80, DAS and SEQ ID NO: 82; or heavy chain CDRs having the amino acid sequences of SEQ ID NOs: 83-85 and light chain CDRs having the amino acid sequences of SEQ ID NO: 86, DAS and SEQ ID NO: 88.

15. The nucleic acid sequence of claim 1, wherein the antibody reagent, antigen-binding portion thereof, or CAR comprises heavy chain CDRs having the amino acid sequences of SEQ ID NOs: 71-73 and light chain CDRs having the amino acid sequences of SEQ ID NO: 74, DAS and SEQ ID NO: 76.

* * * * *

SEQUENCE LISTING

```
Sequence total quantity: 248
SEQ ID NO: 1              moltype = AA   length = 116
FEATURE                   Location/Qualifiers
source                    1..116
                          mol_type = protein
                          organism = synthetic construct
                          note = Description of Artificial Sequence: Synthetic
                          polypeptide
SEQUENCE: 1
QVQLVESGGD VVQPGGSLRL SCAASGVAFS DSGMHWVRQA PGKGLEWLAV IWYDGSKKHY    60
AEAVKGRFTI SRDNSKNMLY LQMNSLRVDD TAIYYCAKAH SQDDYWGQGT LVTVSS        116

SEQ ID NO: 2              moltype = AA   length = 107
FEATURE                   Location/Qualifiers
source                    1..107
                          mol_type = protein
                          organism = synthetic construct
                          note = Description of Artificial Sequence: Synthetic
                          polypeptide
SEQUENCE: 2
EIVLTQSPAT LSLSPGERAT LSCRATPSID SYLAWYQQKS GQSPRLIIHD ASIRATGIPD    60
RFSGSGSGTD FTLTISSLEP EDFAVYYCQQ RDSWPLAFGG GTKVEFK                  107

SEQ ID NO: 3              moltype = AA   length = 117
FEATURE                   Location/Qualifiers
source                    1..117
                          mol_type = protein
                          organism = synthetic construct
                          note = Description of Artificial Sequence: Synthetic
                          polypeptide
SEQUENCE: 3
QEWLVESGGD VVQPGGSLRL SCATSKVTFN DFGIHWVRQA PGKGLEWVAI IWYDGSRNHY    60
ADSVRGRFTL SRDNSKNMVH LHMSSLRTED TAMYYCARGI HSNDDYWGQG TMVTVSS       117

SEQ ID NO: 4              moltype = AA   length = 107
FEATURE                   Location/Qualifiers
source                    1..107
                          mol_type = protein
                          organism = synthetic construct
                          note = Description of Artificial Sequence: Synthetic
                          polypeptide
SEQUENCE: 4
EIVLTQSPAT LSLSPGERAT LSCRTSQSVS SDLAWFQQKP GQAPRLFIFD ASKRVNGIPA    60
RFSGSGSGTD FTLTISSLEP EDFAVYYCQQ RTDWPLTFGG GSRVEIK                  107

SEQ ID NO: 5              moltype = AA   length = 116
FEATURE                   Location/Qualifiers
source                    1..116
```

```
                              mol_type = protein
                              organism = synthetic construct
                              note = Description of Artificial Sequence: Synthetic
                               polypeptide
SEQUENCE: 5
QVQLVESGGD VVQSGGSLRL SCAVSGVVFS DYGFEWVRQA PGKGLEWVAV IWYDGSRKHY  60
ADSVQGRFTI SRDNFRNMLY LQMTGLRVED TAKYYCTRSH SHEDYWGQGT LVTVSS       116

SEQ ID NO: 6                  moltype = AA  length = 107
FEATURE                       Location/Qualifiers
source                        1..107
                              mol_type = protein
                              organism = synthetic construct
                              note = Description of Artificial Sequence: Synthetic
                               polypeptide
SEQUENCE: 6
EIVLTQSPAT LSLSPGERAT LSCGASQNID NSLAWFQQKP GQAPRLIIYD ASKRATGIPA  60
RFSGSGSGTD FTLTISTLEP EDFAVYYCQQ RDHWPLNFGG GTKVEVK               107

SEQ ID NO: 7                  moltype = AA  length = 116
FEATURE                       Location/Qualifiers
source                        1..116
                              mol_type = protein
                              organism = synthetic construct
                              note = Description of Artificial Sequence: Synthetic
                               polypeptide
SEQUENCE: 7
QVQLVESGGD VVQPGGSLRL SCAVSGVTFG DFGFEWVRQA PGKGLEWVAV IWYDGSRKHY  60
AESVRGRFTI SRDNSRNMMY LEMTGLRVED TAKYYCTRSH SHEDYWGQGT LVTVSS       116

SEQ ID NO: 8                  moltype = AA  length = 107
FEATURE                       Location/Qualifiers
source                        1..107
                              mol_type = protein
                              organism = synthetic construct
                              note = Description of Artificial Sequence: Synthetic
                               polypeptide
SEQUENCE: 8
EIVLTQSPAT LSLSPGERAT LSCRASQSIS NYLAWFQQKS GQAPRLIIHD AFKRAAGIPT  60
RFSGSGSGTD FTLTISSLEP EDFAVYYCQQ RDNWPLNFGG GTKVEIK               107

SEQ ID NO: 9                  moltype = AA  length = 119
FEATURE                       Location/Qualifiers
source                        1..119
                              mol_type = protein
                              organism = synthetic construct
                              note = Description of Artificial Sequence: Synthetic
                               polypeptide
SEQUENCE: 9
QVQLVESGGD VVQPGGSLRL SCAASGVVFS DYGLYWVRQA PGKGLEWVAL IWYDGSKKFY  60
ADSVKGRFSI SRDNSKNMLY LQMNNLRADD SAIYYCSRGI RQGPWFAYWG QGTRVTVSP   119

SEQ ID NO: 10                 moltype = AA  length = 107
FEATURE                       Location/Qualifiers
source                        1..107
                              mol_type = protein
                              organism = synthetic construct
                              note = Description of Artificial Sequence: Synthetic
                               polypeptide
SEQUENCE: 10
EIVLTQSPAT LSLSPGERAT LSCRASQSIS SDLTWFQQKP GQAPRLIIYD ASNRATGIPA  60
RFSGSGSGTD FTLTISSLEP EDFVVYYCLQ RSDWPLTFGG GTKVEIK               107

SEQ ID NO: 11                 moltype = AA  length = 116
FEATURE                       Location/Qualifiers
source                        1..116
                              mol_type = protein
                              organism = synthetic construct
                              note = Description of Artificial Sequence: Synthetic
                               polypeptide
SEQUENCE: 11
QVQLVESGGD VVQPGGSLRL SCTVSGAVFR DLGMEWVRQA PGKGLEWLAV IWYDGGRKHY  60
ADSVKGRFTI SRDNSRNMLF LQMNGLRVDD TAMYYCTRSH STDDYWGQGT LVTVSS       116

SEQ ID NO: 12                 moltype = AA  length = 107
FEATURE                       Location/Qualifiers
source                        1..107
                              mol_type = protein
                              organism = synthetic construct
```

-continued

```
                                note = Description of Artificial Sequence: Synthetic
                                  polypeptide
SEQUENCE: 12
EIVLTQSPAT LSVSPGERAT LSCRASQSIS SDLAWFQQKP GQAPRLIIHG ASKRATGIPA  60
RFSGSGSGTD FTLTISSLEP EDFAVYYCQQ RDSWPLNFGG GTKVEIK                107

SEQ ID NO: 13           moltype = AA  length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 13
QVQLVESGGD VVQPGGSLRL SCSASGLVIS DYGMNWVRQA PGKGLEWVGL IWYDGSKKYY  60
SDFVKGRFTI SRDNSKNILY LQMNNLRAED TAMYYCARFL IGATRRGNAM DYWGQGTSVT  120
VSS                                                                123

SEQ ID NO: 14           moltype = AA  length = 107
FEATURE                 Location/Qualifiers
source                  1..107
                        mol_type = protein
                        organism = synthetic construct
                        note = Description of Artificial Sequence: Synthetic
                          polypeptide
SEQUENCE: 14
EVVLTQSPAT LSLSPGERAT LSCRASQSID SDLAWSQQKP GQPPRLIIYD ASNRATGIPA  60
RFSGSGSGTD FTLTISSLEP EDFAVYYCQQ RSDWPLTFGG GTKVEIR                107

SEQ ID NO: 15           moltype = AA  length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 15
QVQLVESGGD VVQPGGSLRL SCSASGLVFR DYGMNWVRQA PGKGLEWVGL IWYDGTKKYY  60
SDFVKGRFTI SRDNSKNMLY LQMNNLRAED TAIYYCARFL IGATRRGNAM DYWGQGTSVI  120
VSS                                                                123

SEQ ID NO: 16           moltype = AA  length = 107
FEATURE                 Location/Qualifiers
source                  1..107
                        mol_type = protein
                        organism = synthetic construct
                        note = Description of Artificial Sequence: Synthetic
                          polypeptide
SEQUENCE: 16
EVVLTQSPAT LSLSPGERAT LSCRASQSID SDLAWSQQKT GQPPRLIIYD ASNRATGIPA  60
RFSGSGSGTD FTLTISSLEP EDFAVYYCQQ RSDWPLTFGG GTKVEIR                107

SEQ ID NO: 17           moltype = AA  length = 116
FEATURE                 Location/Qualifiers
source                  1..116
                        mol_type = protein
                        organism = synthetic construct
                        note = Description of Artificial Sequence: Synthetic
                          polypeptide
SEQUENCE: 17
QLQLVESGGD VVQPGGSLRL SCAASGVVFS DFGLEWVRQA PGKGLEWLAV IWYDGSRKHY  60
ADSVKGRFTI SRDNSKNMLY LQMNSLRVED TAMYYCARCH SKEDYWGQGT LVTVSS      116

SEQ ID NO: 18           moltype = AA  length = 107
FEATURE                 Location/Qualifiers
source                  1..107
                        mol_type = protein
                        organism = synthetic construct
                        note = Description of Artificial Sequence: Synthetic
                          polypeptide
SEQUENCE: 18
EIEVTQSPAT LSLSPGERAT LSCRASQSID TDLAWFQQRP GQTPRLIIYD ASKRATGIPA  60
RFSGGGSGTD FTLTISSLEP EDFAVYYCQQ RTTWPLTFGG GTKVEIK                107

SEQ ID NO: 19           moltype = AA  length = 123
FEATURE                 Location/Qualifiers
source                  1..123
                        mol_type = protein
                        organism = synthetic construct
```

-continued

```
                               note = Description of Artificial Sequence: Synthetic
                                 polypeptide
SEQUENCE: 19
QVQLVESGGD VVQPGGSLRL SCSASGLVIS DYGMNWVRQA PGKGLEWVGL IWYDGSKKYY   60
SDFVKGRFTI SRDNSKNILY LQMNNLRAED TAMYYCARFL IGATRRGNAM DYWGQGTSVT   120
VSS                                                                123

SEQ ID NO: 20          moltype = AA  length = 107
FEATURE                Location/Qualifiers
source                 1..107
                       mol_type = protein
                       organism = synthetic construct
                       note = Description of Artificial Sequence: Synthetic
                         polypeptide
SEQUENCE: 20
EVVLTQSPAT LSLSPGERAT LSCRASQSID SDLAWSQQKP GQPPRLIIYD ASNRATGIPA   60
RFSGSGSGTD FTLTISSLED EDFAVYYCQQ RSDWPLTFGG GTKVEIR                 107

SEQ ID NO: 21          moltype = AA  length = 123
FEATURE                Location/Qualifiers
source                 1..123
                       mol_type = protein
                       organism = synthetic construct
                       note = Description of Artificial Sequence: Synthetic
                         polypeptide
SEQUENCE: 21
QVQLVESGGD VVQPGGSLRL SCAASGVAFR NYGMHWVRQA PGKGLEWVAI IWYDGSNKYY   60
ADSVKGRFTI SRDNSKNMLY LQMNSLRAED TAMYYCARLS IGTTHYFDTD DYWGQGTSVT   120
VSS                                                                123

SEQ ID NO: 22          moltype = AA  length = 107
FEATURE                Location/Qualifiers
source                 1..107
                       mol_type = protein
                       organism = synthetic construct
                       note = Description of Artificial Sequence: Synthetic
                         polypeptide
SEQUENCE: 22
EIVLTQSPAT LSLSPGERAT LSCRASQSVS SYLAWYQQKV GQAPRLIIFD ASNRATGIPA   60
RFSGSGSGTD FTLTITSLDP EDFAVYYCQQ RSAWPLTFGG GTKVEIR                 107

SEQ ID NO: 23          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 23
GVAFSDSG                                                            8

SEQ ID NO: 24          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 24
IWYDGSKK                                                            8

SEQ ID NO: 25          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 25
AKAHSQDDY                                                           9

SEQ ID NO: 26          moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 26
PSIDSY                                                              6

SEQ ID NO: 27          moltype =   length =
SEQUENCE: 27
```

-continued

```
000

SEQ ID NO: 28          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 28
QQRDSWPLA                                                          9

SEQ ID NO: 29          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 29
KVTFNDFG                                                           8

SEQ ID NO: 30          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 30
IWYDGSRN                                                           8

SEQ ID NO: 31          moltype = AA  length = 10
FEATURE                Location/Qualifiers
source                 1..10
                       mol_type = protein
                       organism = synthetic construct
                       note = Description of Artificial Sequence: Synthetic peptide
SEQUENCE: 31
ARGIHSNDDY                                                         10

SEQ ID NO: 32          moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 32
QSVSSD                                                             6

SEQ ID NO: 33          moltype =    length =
SEQUENCE: 33
000

SEQ ID NO: 34          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 34
QQRTDWPLT                                                          9

SEQ ID NO: 35          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 35
GVVFSDYG                                                           8

SEQ ID NO: 36          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 36
IWYDGSRK                                                           8

SEQ ID NO: 37          moltype = AA  length = 9
```

-continued

```
FEATURE                   Location/Qualifiers
source                    1..9
                          mol_type = protein
                          organism = synthetic construct
                          note = Description of Artificial Sequence: Synthetic peptide
SEQUENCE: 37
TRSHSHEDY                                                                        9

SEQ ID NO: 38             moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 38
QNIDNS                                                                           6

SEQ ID NO: 39             moltype =   length =
SEQUENCE: 39
000

SEQ ID NO: 40             moltype = AA   length = 9
FEATURE                   Location/Qualifiers
source                    1..9
                          mol_type = protein
                          organism = synthetic construct
                          note = Description of Artificial Sequence: Synthetic peptide
SEQUENCE: 40
QQRDHWPLN                                                                        9

SEQ ID NO: 41             moltype = AA   length = 8
FEATURE                   Location/Qualifiers
source                    1..8
                          mol_type = protein
                          organism = synthetic construct
                          note = Description of Artificial Sequence: Synthetic peptide
SEQUENCE: 41
GVTFGDFG                                                                         8

SEQ ID NO: 42             moltype = AA   length = 8
FEATURE                   Location/Qualifiers
source                    1..8
                          mol_type = protein
                          organism = synthetic construct
                          note = Description of Artificial Sequence: Synthetic peptide
SEQUENCE: 42
IWYDGSRK                                                                         8

SEQ ID NO: 43             moltype = AA   length = 9
FEATURE                   Location/Qualifiers
source                    1..9
                          mol_type = protein
                          organism = synthetic construct
                          note = Description of Artificial Sequence: Synthetic peptide
SEQUENCE: 43
TRSHSHEDY                                                                        9

SEQ ID NO: 44             moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 44
QSISNY                                                                           6

SEQ ID NO: 45             moltype =   length =
SEQUENCE: 45
000

SEQ ID NO: 46             moltype = AA   length = 9
FEATURE                   Location/Qualifiers
source                    1..9
                          mol_type = protein
                          organism = synthetic construct
                          note = Description of Artificial Sequence: Synthetic peptide
SEQUENCE: 46
QQRDNWPLN                                                                        9
```

-continued

```
SEQ ID NO: 47      moltype = AA  length = 8
FEATURE            Location/Qualifiers
source             1..8
                   mol_type = protein
                   organism = synthetic construct
                   note = Description of Artificial Sequence: Synthetic peptide
SEQUENCE: 47
GVVFSDYG                                                    8

SEQ ID NO: 48      moltype = AA  length = 8
FEATURE            Location/Qualifiers
source             1..8
                   mol_type = protein
                   organism = synthetic construct
                   note = Description of Artificial Sequence: Synthetic peptide
SEQUENCE: 48
IWYDGSKK                                                    8

SEQ ID NO: 49      moltype = AA  length = 12
FEATURE            Location/Qualifiers
source             1..12
                   mol_type = protein
                   organism = synthetic construct
                   note = Description of Artificial Sequence: Synthetic peptide
SEQUENCE: 49
SRGIRQGPWF AY                                               12

SEQ ID NO: 50      moltype = AA  length = 6
FEATURE            Location/Qualifiers
source             1..6
                   mol_type = protein
                   organism = synthetic construct
                   note = Description of Artificial Sequence: Synthetic peptide
SEQUENCE: 50
QSISSD                                                      6

SEQ ID NO: 51      moltype =    length =
SEQUENCE: 51
000

SEQ ID NO: 52      moltype = AA  length = 9
FEATURE            Location/Qualifiers
source             1..9
                   mol_type = protein
                   organism = synthetic construct
                   note = Description of Artificial Sequence: Synthetic peptide
SEQUENCE: 52
LQRSDWPLT                                                   9

SEQ ID NO: 53      moltype = AA  length = 8
FEATURE            Location/Qualifiers
source             1..8
                   mol_type = protein
                   organism = synthetic construct
                   note = Description of Artificial Sequence: Synthetic peptide
SEQUENCE: 53
GAVFRDLG                                                    8

SEQ ID NO: 54      moltype = AA  length = 8
FEATURE            Location/Qualifiers
source             1..8
                   mol_type = protein
                   organism = synthetic construct
                   note = Description of Artificial Sequence: Synthetic peptide
SEQUENCE: 54
IWYDGGRK                                                    8

SEQ ID NO: 55      moltype = AA  length = 9
FEATURE            Location/Qualifiers
source             1..9
                   mol_type = protein
                   organism = synthetic construct
                   note = Description of Artificial Sequence: Synthetic peptide
SEQUENCE: 55
TRSHSTDDY                                                   9

SEQ ID NO: 56      moltype = AA  length = 6
FEATURE            Location/Qualifiers
source             1..6
```

```
                          mol_type = protein
                          organism = synthetic construct
                          note = Description of Artificial Sequence: Synthetic peptide
SEQUENCE: 56
QSISSD                                                                    6

SEQ ID NO: 57            moltype =   length =
SEQUENCE: 57
000

SEQ ID NO: 58            moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 58
QQRDSWPLN                                                                 9

SEQ ID NO: 59            moltype = AA   length = 8
FEATURE                  Location/Qualifiers
source                   1..8
                         mol_type = protein
                         organism = synthetic construct
                         note = Description of Artificial Sequence: Synthetic peptide
SEQUENCE: 59
GLVISDYG                                                                  8

SEQ ID NO: 60            moltype = AA   length = 8
FEATURE                  Location/Qualifiers
source                   1..8
                         mol_type = protein
                         organism = synthetic construct
                         note = Description of Artificial Sequence: Synthetic peptide
SEQUENCE: 60
IWYDGSKK                                                                  8

SEQ ID NO: 61            moltype = AA   length = 16
FEATURE                  Location/Qualifiers
source                   1..16
                         mol_type = protein
                         organism = synthetic construct
                         note = Description of Artificial Sequence: Synthetic peptide
SEQUENCE: 61
ARFLIGATRR GNAMDY                                                        16

SEQ ID NO: 62            moltype = AA   length = 6
FEATURE                  Location/Qualifiers
source                   1..6
                         mol_type = protein
                         organism = synthetic construct
                         note = Description of Artificial Sequence: Synthetic peptide
SEQUENCE: 62
QSIDSD                                                                    6

SEQ ID NO: 63            moltype =   length =
SEQUENCE: 63
000

SEQ ID NO: 64            moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 64
QQRSDWPLT                                                                 9

SEQ ID NO: 65            moltype = AA   length = 8
FEATURE                  Location/Qualifiers
source                   1..8
                         mol_type = protein
                         organism = synthetic construct
                         note = Description of Artificial Sequence: Synthetic peptide
SEQUENCE: 65
GLVFRDYG                                                                  8

SEQ ID NO: 66            moltype = AA   length = 8
FEATURE                  Location/Qualifiers
```

-continued

```
source                1..8
                      mol_type = protein
                      organism = synthetic construct
                      note = Description of Artificial Sequence: Synthetic peptide
SEQUENCE: 66
IWYDGTKK                                                    8

SEQ ID NO: 67         moltype = AA  length = 16
FEATURE               Location/Qualifiers
source                1..16
                      mol_type = protein
                      organism = synthetic construct
                      note = Description of Artificial Sequence: Synthetic peptide
SEQUENCE: 67
ARFLIGATRR GNAMDY                                          16

SEQ ID NO: 68         moltype = AA  length = 6
FEATURE               Location/Qualifiers
source                1..6
                      mol_type = protein
                      organism = synthetic construct
                      note = Description of Artificial Sequence: Synthetic peptide
SEQUENCE: 68
QSIDSD                                                      6

SEQ ID NO: 69         moltype =    length =
SEQUENCE: 69
000

SEQ ID NO: 70         moltype = AA  length = 9
FEATURE               Location/Qualifiers
source                1..9
                      mol_type = protein
                      organism = synthetic construct
                      note = Description of Artificial Sequence: Synthetic peptide
SEQUENCE: 70
QQRSDWPLT                                                   9

SEQ ID NO: 71         moltype = AA  length = 8
FEATURE               Location/Qualifiers
source                1..8
                      mol_type = protein
                      organism = synthetic construct
                      note = Description of Artificial Sequence: Synthetic peptide
SEQUENCE: 71
GVVFSDFG                                                    8

SEQ ID NO: 72         moltype = AA  length = 8
FEATURE               Location/Qualifiers
source                1..8
                      mol_type = protein
                      organism = synthetic construct
                      note = Description of Artificial Sequence: Synthetic peptide
SEQUENCE: 72
IWYDGSRK                                                    8

SEQ ID NO: 73         moltype = AA  length = 9
FEATURE               Location/Qualifiers
source                1..9
                      mol_type = protein
                      organism = synthetic construct
                      note = Description of Artificial Sequence: Synthetic peptide
SEQUENCE: 73
ARCHSKEDY                                                   9

SEQ ID NO: 74         moltype = AA  length = 6
FEATURE               Location/Qualifiers
source                1..6
                      mol_type = protein
                      organism = synthetic construct
                      note = Description of Artificial Sequence: Synthetic peptide
SEQUENCE: 74
QSIDTD                                                      6

SEQ ID NO: 75         moltype =    length =
SEQUENCE: 75
000

SEQ ID NO: 76         moltype = AA  length = 9
```

-continued

```
FEATURE                Location/Qualifiers
source                 1..9
                       mol_type = protein
                       organism = synthetic construct
                       note = Description of Artificial Sequence: Synthetic peptide
SEQUENCE: 76
QQRTTWPLT                                                              9

SEQ ID NO: 77          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 77
GLVISDYG                                                               8

SEQ ID NO: 78          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 78
IWYDGSKK                                                               8

SEQ ID NO: 79          moltype = AA  length = 16
FEATURE                Location/Qualifiers
source                 1..16
                       mol_type = protein
                       organism = synthetic construct
                       note = Description of Artificial Sequence: Synthetic peptide
SEQUENCE: 79
ARFLIGATRR GNAMDY                                                      16

SEQ ID NO: 80          moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 80
QSIDSD                                                                 6

SEQ ID NO: 81          moltype =   length =
SEQUENCE: 81
000

SEQ ID NO: 82          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 82
QQRSDWPLT                                                              9

SEQ ID NO: 83          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 83
GVAFRNYG                                                               8

SEQ ID NO: 84          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 84
IWYDGSNK                                                               8

SEQ ID NO: 85          moltype = AA  length = 16
FEATURE                Location/Qualifiers
source                 1..16
                       mol_type = protein
```

-continued

```
                            organism = synthetic construct
                            note = Description of Artificial Sequence: Synthetic peptide
SEQUENCE: 85
ARLSIGTTHY FDTDDY                                                   16

SEQ ID NO: 86               moltype = AA   length = 6
FEATURE                     Location/Qualifiers
source                      1..6
                            mol_type = protein
                            organism = synthetic construct
                            note = Description of Artificial Sequence: Synthetic peptide
SEQUENCE: 86
QSVSSY                                                              6

SEQ ID NO: 87               moltype =    length =
SEQUENCE: 87
000

SEQ ID NO: 88               moltype = AA   length = 9
FEATURE                     Location/Qualifiers
source                      1..9
                            mol_type = protein
                            organism = synthetic construct
                            note = Description of Artificial Sequence: Synthetic peptide
SEQUENCE: 88
QQRSAWPLT                                                           9

SEQ ID NO: 89               moltype = AA   length = 6
FEATURE                     Location/Qualifiers
source                      1..6
                            mol_type = protein
                            organism = synthetic construct
                            note = Description of Artificial Sequence: Synthetic 6xHis
                             tag
SEQUENCE: 89
HHHHHH                                                              6

SEQ ID NO: 90               moltype = AA   length = 5
FEATURE                     Location/Qualifiers
source                      1..5
                            mol_type = protein
                            organism = synthetic construct
                            note = Description of Artificial Sequence: Synthetic peptide
SEQUENCE: 90
GGGGS                                                               5

SEQ ID NO: 91               moltype = AA   length = 113
FEATURE                     Location/Qualifiers
source                      1..113
                            mol_type = protein
                            organism = synthetic construct
                            note = Description of Artificial Sequence: Synthetic
                             polypeptide
SEQUENCE: 91
QVQLVESGGD VVQPGGSLRL SCAASGVAFS NYGMHWVRQA PGKGLEWVAV IWYDGSNKYY  60
ADSVKGRFTI SRDNSKNMLY LQMNSLRAED TAMYYCARND DYWGQGTLVT VSS         113

SEQ ID NO: 92               moltype = AA   length = 117
FEATURE                     Location/Qualifiers
source                      1..117
                            mol_type = protein
                            organism = synthetic construct
                            note = Description of Artificial Sequence: Synthetic
                             polypeptide
SEQUENCE: 92
QVQLVESGGD VVQPGGSLRL SCAASGVAFS DSGMHWVRQA PGKGLEWLAV IWYDGSKKHY  60
AEAVKGRFTI SRDNSKNMLY LQMNSLRVDD TAIYYCAKAH SQDDYWGQGT LVTVSSA     117

SEQ ID NO: 93               moltype = AA   length = 114
FEATURE                     Location/Qualifiers
source                      1..114
                            mol_type = protein
                            organism = synthetic construct
                            note = Description of Artificial Sequence: Synthetic
                             polypeptide
SEQUENCE: 93
QVQMVESGGD VVQPGGSLRL SCAASGVAFS NYGMHWVRQA PGKGLEWVAV IWYDGSNKNY  60
ADSVKGRFTI SRDNSKNMLY LQMNSLRVED TAMYYCASND DYWGQGTLVT VSSA        114
```

-continued

```
SEQ ID NO: 94              moltype = AA  length = 113
FEATURE                    Location/Qualifiers
source                     1..113
                           mol_type = protein
                           organism = synthetic construct
                           note = Description of Artificial Sequence: Synthetic
                            polypeptide
SEQUENCE: 94
QVQLVESGGD VVQPGGGSLRL SCAASGVAFR DYGMHWVRQA PGKGLEWVAV IWYDGSKKYY  60
GDSVKGRFTV SRDNSKNMLY LEMNGLKAED TAMYYCARND DYWGQGTLVT VSS         113

SEQ ID NO: 95              moltype = AA  length = 116
FEATURE                    Location/Qualifiers
source                     1..116
                           mol_type = protein
                           organism = synthetic construct
                           note = Description of Artificial Sequence: Synthetic
                            polypeptide
SEQUENCE: 95
QVQLVESGGD VVQPGGGSLRL SCAASGVAFS DYGMEWVRQA PGKGLEWLAV IWYDGSRKHY  60
ADSVKGRFTI SRDNSKNILY LQMNSLRAED TAMYYCARCH SKDDYWGQGT LVTVSS      116

SEQ ID NO: 96              moltype = AA  length = 117
FEATURE                    Location/Qualifiers
source                     1..117
                           mol_type = protein
                           organism = synthetic construct
                           note = Description of Artificial Sequence: Synthetic
                            polypeptide
SEQUENCE: 96
QEWLVESGGD VVQPGGGSLRL SCATSKVTFN DFGIHWVRQA PGKGLEWVAI IWYDGSRNHY  60
ADSVRGRFTL SRDNSKNMVH LHMSSLRTED TAMYYCARGI HSNDDYWGQG TMVTVSS     117

SEQ ID NO: 97              moltype = AA  length = 113
FEATURE                    Location/Qualifiers
source                     1..113
                           mol_type = protein
                           organism = synthetic construct
                           note = Description of Artificial Sequence: Synthetic
                            polypeptide
SEQUENCE: 97
QVQLVESGGD VVQPGGGSLTL SCAASGAAFS NYGMHWVRQA PGKGLEWVAV IWYDGSNKYY  60
GDSVKGRFTI SRDNSKNMLY LQMNSLRAED TAMYYCARND DYWGQGTLVT VSS         113

SEQ ID NO: 98              moltype = AA  length = 117
FEATURE                    Location/Qualifiers
source                     1..117
                           mol_type = protein
                           organism = synthetic construct
                           note = Description of Artificial Sequence: Synthetic
                            polypeptide
SEQUENCE: 98
QEWLVESGGD VVQPGGGSLRL SCATSKVTFN DFGIHWVRQA PGKGLEWVAI IWYDGSRNHY  60
ADSVRGRFTL SRDNSKNMVH LHMSSLRTED TAMYYCARGI HSNDDYWGQG TMVTVSS     117

SEQ ID NO: 99              moltype = AA  length = 116
FEATURE                    Location/Qualifiers
source                     1..116
                           mol_type = protein
                           organism = synthetic construct
                           note = Description of Artificial Sequence: Synthetic
                            polypeptide
SEQUENCE: 99
QVQLVESGGD VVQPGGGSLRL SCAVSGVTFG DFGFEWVRQA PGKGLEWVAV IWYDGSRKHY  60
AESVRGRFTI SRDNSRNMMY LEMTGLRVED TAKYYCTRSH SHEDYWGQGT LVTVSS      116

SEQ ID NO: 100             moltype = AA  length = 113
FEATURE                    Location/Qualifiers
source                     1..113
                           mol_type = protein
                           organism = synthetic construct
                           note = Description of Artificial Sequence: Synthetic
                            polypeptide
SEQUENCE: 100
QVQLVESGGD VVQPGGGSLRL SCAASGVAFR DYGMHWVRQA PGKGLEWVAV IWYDGSKKYY  60
GDSVKGRFTV SRDNSKNMLY LEMNGLKAED TAMYYCARND DYWGQGTLVT VSS         113

SEQ ID NO: 101             moltype = AA  length = 116
FEATURE                    Location/Qualifiers
```

```
source                  1..116
                        mol_type = protein
                        organism = synthetic construct
                        note = Description of Artificial Sequence: Synthetic
                         polypeptide
SEQUENCE: 101
QVQLVESGGD VVQPGGSLRL SCTVSGAVFR DLGMEWVRQA PGKGLEWLAV IWYDGGRKHY  60
ADSVKGRFTI SRDNSRNMLF LQMNGLRVDD TAMYYCTRSH STDDYWGQGT LVTVSS      116

SEQ ID NO: 102          moltype = AA  length = 116
FEATURE                 Location/Qualifiers
source                  1..116
                        mol_type = protein
                        organism = synthetic construct
                        note = Description of Artificial Sequence: Synthetic
                         polypeptide
SEQUENCE: 102
QVQLVESGGD VVQPGGSLRL SCAVSGAVFR DLGMEWVRQA PGKGLEWLAV IWYDGSRKHY  60
ADSVKGRFTI SRDNSRNMLY LQMNGLRVDD TAMYYCTRSH STDDYWGQGT LVTVSS      116

SEQ ID NO: 103          moltype = AA  length = 114
FEATURE                 Location/Qualifiers
source                  1..114
                        mol_type = protein
                        organism = synthetic construct
                        note = Description of Artificial Sequence: Synthetic
                         polypeptide
SEQUENCE: 103
QVQLVESGGD VVQPGGSLRL SCAASGVAFS NYGMHWVRQA PGKGLEWVAV IWYDGSKKYY  60
ADSVKGRFTI SRDNSKNMLY LQMNSLRAED TAMYYCANHS DDFWGQGTLV TVSS        114

SEQ ID NO: 104          moltype = AA  length = 113
FEATURE                 Location/Qualifiers
source                  1..113
                        mol_type = protein
                        organism = synthetic construct
                        note = Description of Artificial Sequence: Synthetic
                         polypeptide
SEQUENCE: 104
QVQLVESGGD VVQPGGSLRL SCAASGVAFR DYGMHWVRQA PGKGLEWVAV IWYDGSKKYY  60
ADSVKGRFTV SRDNSKNMLY LQMNGLRAED TAMYYCARND DYWGQGTLVT VSS         113

SEQ ID NO: 105          moltype = AA  length = 113
FEATURE                 Location/Qualifiers
source                  1..113
                        mol_type = protein
                        organism = synthetic construct
                        note = Description of Artificial Sequence: Synthetic
                         polypeptide
SEQUENCE: 105
QVQLVESGGD VVQPGGSLRL SCAASGVAFS NYGMHWVRQA PGKGLEWVAV IWYDGSKKYY  60
GDSVKGRFTI SRDNSKNMLY LQMNSLRAED TAMYYCARND DYWGQGTLVT VSS         113

SEQ ID NO: 106          moltype = AA  length = 116
FEATURE                 Location/Qualifiers
source                  1..116
                        mol_type = protein
                        organism = synthetic construct
                        note = Description of Artificial Sequence: Synthetic
                         polypeptide
SEQUENCE: 106
QVQLVESGGD VVQSGGSLRL SCAVSGVVFS DYGFEWVRQA PGKGLEWVAV IWYDGSRKHY  60
ADSVQGRFTI SRDNFRNMLY LQMTGLRVED TAKYYCTRSH SHEDYWGQGT LVTVSS      116

SEQ ID NO: 107          moltype = AA  length = 113
FEATURE                 Location/Qualifiers
source                  1..113
                        mol_type = protein
                        organism = synthetic construct
                        note = Description of Artificial Sequence: Synthetic
                         polypeptide
SEQUENCE: 107
QVQLVESGGD VVQPGGSLRL SCAASGVAFR DYGMHWVRQA PGKGLEWVAV IWYDGSKKYY  60
GDSVKGRFTV SRDNSKNMLY LEMNGLKAED TAMYYCARND DYWGQGTLVT VSS         113

SEQ ID NO: 108          moltype = AA  length = 113
FEATURE                 Location/Qualifiers
source                  1..113
                        mol_type = protein
```

```
                              organism = synthetic construct
                              note = Description of Artificial Sequence: Synthetic
                               polypeptide
SEQUENCE: 108
QVQLVESGGD VVQPGGSLRV SCAASGVAFS NYGMHWVRQA PGKGLEWVAV IWYDGSKKYY  60
AESVKGRFTI SRDNSKNMLY LQMHSLRAED TAMYYCARND DYWGQGTLVT VSS         113

SEQ ID NO: 109            moltype = AA  length = 115
FEATURE                   Location/Qualifiers
source                    1..115
                          mol_type = protein
                          organism = synthetic construct
                          note = Description of Artificial Sequence: Synthetic
                           polypeptide
SEQUENCE: 109
QVQLVESGGD VVKPGGSLRI SCGVSGVAFS DYGMSWVRQA PGKGLEWLAV IWYDGSKKHY  60
ADSVKGRFTI SRDNSKNMLY LQMNNLRAED TAMYFCARSH SDDYWGQGTL VTVSS       115

SEQ ID NO: 110            moltype = AA  length = 116
FEATURE                   Location/Qualifiers
source                    1..116
                          mol_type = protein
                          organism = synthetic construct
                          note = Description of Artificial Sequence: Synthetic
                           polypeptide
SEQUENCE: 110
QVQLVESGGD VVQPGGSLRL SCAASGVAFS DYGMEWVRQA PGKGLEWLAV IWYDGSRKHY  60
AESVKGRFTI SRDNSKNILY LQMNSLRAED TAMYYCVRCH SKDNYWGQGT LVTVSS      116

SEQ ID NO: 111            moltype = AA  length = 113
FEATURE                   Location/Qualifiers
source                    1..113
                          mol_type = protein
                          organism = synthetic construct
                          note = Description of Artificial Sequence: Synthetic
                           polypeptide
SEQUENCE: 111
QVQLVESGGD VVQPGGSLRV SCAASGGALS NYGMHWVRQA PGKGLEWVAV IWYDGSKKYY  60
ADSVKGRFTI SRDNSMNMLY LQMNSLRTDD TAMYYCARND DYWGQGTLVT VSS         113

SEQ ID NO: 112            moltype = AA  length = 114
FEATURE                   Location/Qualifiers
source                    1..114
                          mol_type = protein
                          organism = synthetic construct
                          note = Description of Artificial Sequence: Synthetic
                           polypeptide
SEQUENCE: 112
QVQLVESGGD VVKPGGSLRI SCGVSGVAFS DYGMSWVRQA PGKGLEWLAV IWYDGSKKHY  60
ADSVKGRFTI SRDNSKNMLY LQMNNLRAED TAMYFCASHS DDYWGQGTLV TVSS        114

SEQ ID NO: 113            moltype = AA  length = 113
FEATURE                   Location/Qualifiers
source                    1..113
                          mol_type = protein
                          organism = synthetic construct
                          note = Description of Artificial Sequence: Synthetic
                           polypeptide
SEQUENCE: 113
QVQLVESGGD VVQPGGSLRL SCAASGVAFS NYGMHWVRQA PGKGLEWVAV IWYDGSKKYY  60
KDSVKGRFTI SRDNSKNVLY LQMNSLRAED TAMYYCARND DYWGRGTLVT VSS         113

SEQ ID NO: 114            moltype = AA  length = 116
FEATURE                   Location/Qualifiers
source                    1..116
                          mol_type = protein
                          organism = synthetic construct
                          note = Description of Artificial Sequence: Synthetic
                           polypeptide
SEQUENCE: 114
QLQLVESGGD VVQPGGSLRL SCAASGVVFS DFGLEWVRQA PGKGLEWLAV IWYDGSRKHY  60
ADSVKGRFTI SRDNSKNMLY LQMNSLRVED TAMYYCARCH SKEDYWGQGT LVTVSS      116

SEQ ID NO: 115            moltype = AA  length = 113
FEATURE                   Location/Qualifiers
source                    1..113
                          mol_type = protein
                          organism = synthetic construct
                          note = Description of Artificial Sequence: Synthetic
```

```
                         polypeptide
SEQUENCE: 115
QVQLVEFGGD VVQPGGSLRL SCAASGVAFS NYGMHWVRQA PGKGLEWVAV IWYDGSNKYY   60
ADSVKGRFTI SRDNSKNMLY LQMNSLRAED TAMYYCARND DYWGQGTLVT VSS          113

SEQ ID NO: 116        moltype = AA   length = 116
FEATURE               Location/Qualifiers
source                1..116
                      mol_type = protein
                      organism = synthetic construct
                      note = Description of Artificial Sequence: Synthetic
                       polypeptide
SEQUENCE: 116
QVQLVESGGD VVQPGGSLRL SCAASGVAFR DYGMHWVRQA PGKGLEWVAV IWYDGSRKEY   60
ADSVKGRFTI SRDNSKNMLY LQMNSLRDDD TAMYFCAKAH SQDDYWGQGT LVTVSS       116

SEQ ID NO: 117        moltype = AA   length = 116
FEATURE               Location/Qualifiers
source                1..116
                      mol_type = protein
                      organism = synthetic construct
                      note = Description of Artificial Sequence: Synthetic
                       polypeptide
SEQUENCE: 117
QVQLVESGGD VVRPGGSLRL SCVVSGVVFS DFGFEWVRQA PGKGLEWVAV IWYDGSRKHY   60
ADSVKGRFTI SRDNSKSMMY LQMNNLRVED TALYYCARSH SNDVYWGQHT LVTVSS       116

SEQ ID NO: 118        moltype = AA   length = 116
FEATURE               Location/Qualifiers
source                1..116
                      mol_type = protein
                      organism = synthetic construct
                      note = Description of Artificial Sequence: Synthetic
                       polypeptide
SEQUENCE: 118
QVQLVESGGD VVQPGGSLRL SCRATGVAFI DYGMHWVRQA PGKGLEWLAV IWYDGSRKHY   60
ADSVKGRFTI SRDNSENMLY LQMNNLRAED TAVYYCARAH SKDDYWGQGT LVTVSS       116

SEQ ID NO: 119        moltype = AA   length = 113
FEATURE               Location/Qualifiers
source                1..113
                      mol_type = protein
                      organism = synthetic construct
                      note = Description of Artificial Sequence: Synthetic
                       polypeptide
SEQUENCE: 119
QVQLVESGGD VVQPGGSLRL SCAASGVAFS NYGMHWVRQA PGKGLEWVAV IWYDGSNKYY   60
ADSVKGRFTI SRDNSKNMLY LQMSSLRAED TAMYYCASNN DYWGQGTLVT VSS          113

SEQ ID NO: 120        moltype = AA   length = 116
FEATURE               Location/Qualifiers
source                1..116
                      mol_type = protein
                      organism = synthetic construct
                      note = Description of Artificial Sequence: Synthetic
                       polypeptide
SEQUENCE: 120
QVHLVESGGD VVQPGGSLTL SCAASGVAFS DFGMHWVRQA PGQGLEWLAV IWYDGSRKHY   60
ADSVKGRFTI SRDNSNNMLF LHMSGLRAED TAIYYCARAH TSDDFWGQGT LVTVSS       116

SEQ ID NO: 121        moltype = AA   length = 113
FEATURE               Location/Qualifiers
source                1..113
                      mol_type = protein
                      organism = synthetic construct
                      note = Description of Artificial Sequence: Synthetic
                       polypeptide
SEQUENCE: 121
QVQLVESGGD VVQPGGSLRL SCAASGVAFS NYGMHWVRQT PGKGLEWVAV IWYDGSNKYY   60
ADSVKGRFTI SRDNSKNMLY LQMSSLRAED TAMYYCASNN DYWGQGTLVT VSS          113

SEQ ID NO: 122        moltype = AA   length = 116
FEATURE               Location/Qualifiers
source                1..116
                      mol_type = protein
                      organism = synthetic construct
                      note = Description of Artificial Sequence: Synthetic
                       polypeptide
SEQUENCE: 122
```

-continued

```
QVQLVESGGD VVQSGGSLRL SCAVSGVVFS DYGFEWVRQA PGKGLEWVAV IWYDGSRKHY  60
ADSVRGRFTI SRDNFRNMLY LQMTGLRVDD TAKYYCTRSH SHEDYWGQGT LVTVSS     116

SEQ ID NO: 123              moltype = AA   length = 113
FEATURE                     Location/Qualifiers
source                      1..113
                            mol_type = protein
                            organism = synthetic construct
                            note = Description of Artificial Sequence: Synthetic
                              polypeptide
SEQUENCE: 123
QVQLVESGGD VVQPGGSLRL SCAASGVAFR DYVMHWVRQA PGKGLEWVAV IWYDGSKKYY  60
GDSVKGRFTV SRDNSKNMLY LEMNGLTAED TAMYYCARND DYWGQGTLVT VSS        113

SEQ ID NO: 124              moltype = AA   length = 107
FEATURE                     Location/Qualifiers
source                      1..107
                            mol_type = protein
                            organism = synthetic construct
                            note = Description of Artificial Sequence: Synthetic
                              polypeptide
SEQUENCE: 124
EIVLTQSPAT LSLSPGERAT LSCRASQSVS SYLAWYQQKP GQAPRLIIYD ASNRATGIPA  60
RFSGSGSGTD FTLTISSLEP EDFAVYYCQQ RSNWPLTFGG GTKVEIK              107

SEQ ID NO: 125              moltype = AA   length = 103
FEATURE                     Location/Qualifiers
source                      1..103
                            mol_type = protein
                            organism = synthetic construct
                            note = Description of Artificial Sequence: Synthetic
                              polypeptide
SEQUENCE: 125
QSPATLSLSP GERATLSCRA TPSIDSYLAW YQQKSGQSPR LIIHDASIRA TGIPDRFSGS  60
GSGTDFTLTI SSLEPEDFAV YYCQQRDSWP LAFGGGTKVE FKR                 103

SEQ ID NO: 126              moltype = AA   length = 103
FEATURE                     Location/Qualifiers
source                      1..103
                            mol_type = protein
                            organism = synthetic construct
                            note = Description of Artificial Sequence: Synthetic
                              polypeptide
SEQUENCE: 126
QSPATLSLSP GERATLSCRA SQSVSNYLAW YQQKPGQAPR LIIYDASNRA TGIPARFSGS  60
GSATDFTLSI SSLEPEDFAV YYCHQRSNWP LTFGGGTKVE IKR                 103

SEQ ID NO: 127              moltype = AA   length = 107
FEATURE                     Location/Qualifiers
source                      1..107
                            mol_type = protein
                            organism = synthetic construct
                            note = Description of Artificial Sequence: Synthetic
                              polypeptide
SEQUENCE: 127
EIVLTQSPAT LSLSPGERAT LSCRASQSVS NSLSWYQQNP GQSPRLIIYD TSKRATGIPA  60
RFSGSGSGTD FTLTINNLET EDFAVYYCHQ RSDWPLTFGG GTKVEIK             107

SEQ ID NO: 128              moltype = AA   length = 107
FEATURE                     Location/Qualifiers
source                      1..107
                            mol_type = protein
                            organism = synthetic construct
                            note = Description of Artificial Sequence: Synthetic
                              polypeptide
SEQUENCE: 128
EIVLTQFPAT LSLSPGERAT LSCRTSQNID SDLAWFQQKP GQAPRLIIYD ASNRATGIPA  60
RFSGGGSGTD FTLTITSLEP EDFAVYYCQQ RTTWPLTFGG GTKVEIK             107

SEQ ID NO: 129              moltype = AA   length = 107
FEATURE                     Location/Qualifiers
source                      1..107
                            mol_type = protein
                            organism = synthetic construct
                            note = Description of Artificial Sequence: Synthetic
                              polypeptide
SEQUENCE: 129
EIVLTQSPAT LSLSPGERAT LSCRTSQSVS SDLAWFQQKP GQAPRLFIFD ASKRVNGIPA  60
RFSGSGSGTD FTLTISSLEP EDFAVYYCQQ RTDWPLTFGG GSRVEIK             107
```

-continued

```
SEQ ID NO: 130          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 130
EIVLTQSPAT LSLSPGERAT LSCRASQSVS SYLAWYQQKP GQAPRLIVYD ASNRATGIPA  60
RFSGSGSGTD FTLTISSLEP EDFAVYYCHQ RSNWPLTFGG GTRVEIK            107

SEQ ID NO: 131          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 131
EIVLTQSPAT LSLSPGERAT LSCRTSQSVS SDLAWFQQKP GQAPRLFIFD ASKRVNGIPA  60
RFSGSGSGTD FTLTISSLEP EDFAVYYCQQ RTDWPLTFGG GSRVEIK            107

SEQ ID NO: 132          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 132
EIVLTQSPAT LSLSPGERAT LSCRASQSIS NYLAWFQQKS GQAPRLIIHD AFKRAAGIPT  60
RFSGSGSGTD FTLTISSLEP EDFAVYYCQQ RDNWPLNFGG GTKVEIK            107

SEQ ID NO: 133          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 133
EIVLTQSPAT LSLSPGERAT LSCRASQSVS NSLSWYQQKP GQSPRLIIYD TSKRATGIPA  60
RFSGSGSGTD FTLTISSLET EDFVVYYCHQ RSDWPLTFGG GTKVEIK            107

SEQ ID NO: 134          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 134
EIVLTQSPAT LSVSPGERAT LSCRASQSIS SDLAWFQQKP GQAPRLIIHG ASKRATGIPA  60
RFSGSGSGTD FTLTISSLEP EDFAVYYCQQ RDSWPLNFGG GTKVEIK            107

SEQ ID NO: 135          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 135
EIVLTQSPAT LSVSPGERAT LSCRASQSIS SDLAWFQQKP GQAPRLIIHG ASKRATGIPA  60
RFSGSGSGTD FTLTISSLEP EDFAVYYCQQ RDSWPLNFGG GTKVEIK            107

SEQ ID NO: 136          moltype = AA   length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 136
EIVLTQSPAT LSLSPGERAT LSCRTSQNID NYLAWYQQKP GQTPRRIIND ASNRATGIPA  60
RFSGSGSGTD FTLTISSLEP EDFAAYYCQQ RSSWPLSFGG GTKLEIK            107

SEQ ID NO: 137          moltype = AA   length = 107
```

-continued

```
FEATURE                  Location/Qualifiers
source                   1..107
                         mol_type = protein
                         organism = synthetic construct
                         note = Description of Artificial Sequence: Synthetic
                          polypeptide
SEQUENCE: 137
EIVLTQSPAT LSLSPGERAT LSCRASQSVS SSLSWYQQKP GQSPRLIIYD TSNRATGIPA  60
RFSGSGSGTD FTLTISSLET EDFAVYYCHQ RSDWPLTFGG GTKVEIK               107

SEQ ID NO: 138           moltype = AA   length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 138
EIVLTQSPAT LSLSPGERAT LSCRASQSVS SDLAWYQQQP GQAPRLIIYD TSNRATGIPA  60
RFSGRGSGTD FTLTINSLEP EDFAVYYCHQ RSDWPLTFGG GTKVEIK               107

SEQ ID NO: 139           moltype = AA   length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 139
EIVLTQSPAT LSLSPGERAT LSCGASQNID NSLAWFQQKP GQAPRLIIYD ASKRATGIPA  60
RFSGSGSGTD FTLTISTLEP EDFAVYYCQQ RDHWPLNFGG GTKVEVK               107

SEQ ID NO: 140           moltype = AA   length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 140
EIVLTQSPAT LSLSPGERAT LSCRASQSVS NSLSWYQQNP GQSPRLIIYD TSKRATGIPA  60
RFSGSGSGTD FTLTISSLET EDFAVYYCHQ RSDWPLTFGG GTKVEIK               107

SEQ ID NO: 141           moltype = AA   length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 141
EIVLTQSPAT LSLSPGERAT LSCRASQSVS SDLSWYQQKP GQAPRLIIYD ASNRATGIPA  60
RFSGSGSGTD FTLTISSLEP EDFAVYYCQQ RSDWPLTFGG GTKVEIK               107

SEQ ID NO: 142           moltype = AA   length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 142
EIVLTQSPAT LSLSPGERAT LSCRTSQSVS SYLAWYQQKP GQAPRLIIYD ASNRATGIPA  60
RFSGSGSGTD FTLTISSLEP EDFAVYYCQQ RDSWPLIFGG GTKVEIK               107

SEQ ID NO: 143           moltype = AA   length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 143
EIVLTQFPAT LSLSPGERAT LSCRTSQNVD SDLAWFQQKP GQAPRLLIYD ASKRATGVPA  60
RFSGGGSGTD FTLTVTSLEP EDFAVYYCQQ RTTWPLVFGG GTKVEIK               107

SEQ ID NO: 144           moltype = AA   length = 107
FEATURE                  Location/Qualifiers
source                   1..107
```

```
                          mol_type = protein
                          organism = synthetic construct
                          note = Description of Artificial Sequence: Synthetic
                           polypeptide
SEQUENCE: 144
EIVLTQSPAT LSLSPGERAT LSCRASQSVS SDLSWYQQKP GQAPRLIIYD ASSRATGIPA   60
RFSGSGSGTD FTLTISSLEP EDFAVYYCQQ RSSWPLTFGG GTKVEIK               107

SEQ ID NO: 145            moltype = AA  length = 107
FEATURE                   Location/Qualifiers
source                    1..107
                          mol_type = protein
                          organism = synthetic construct
                          note = Description of Artificial Sequence: Synthetic
                           polypeptide
SEQUENCE: 145
EIVLTQSPAT LSLSPGERAT LSCRTSQSVS SYLAWYQQKP GQAPRLIIYD ASNRATGIPA   60
RFSGSGSGTD FTLTISSLEP EDFAVYYCQQ RDSWPLIFGG GTKVEIK               107

SEQ ID NO: 146            moltype = AA  length = 107
FEATURE                   Location/Qualifiers
source                    1..107
                          mol_type = protein
                          organism = synthetic construct
                          note = Description of Artificial Sequence: Synthetic
                           polypeptide
SEQUENCE: 146
EIVLTQSPAS LSLSPGERAT LSCRASQSIS SDISWYQQKP GQAPRLIIYD ASNRATGIPA   60
RFSGSGSETD FTLTISSLEP EDFATYYCQQ RSNWPLTFGG GTTVEIT               107

SEQ ID NO: 147            moltype = AA  length = 107
FEATURE                   Location/Qualifiers
source                    1..107
                          mol_type = protein
                          organism = synthetic construct
                          note = Description of Artificial Sequence: Synthetic
                           polypeptide
SEQUENCE: 147
EIEVTQSPAT LSLSPGERAT LSCRASQSID TDLAWFQQRP GQTPRLIIYD ASKRATGIPA   60
RFSGGGSGTD FTLTISSLEP EDFAVYYCQQ RTTWPLTFGG GTKVEIK               107

SEQ ID NO: 148            moltype = AA  length = 107
FEATURE                   Location/Qualifiers
source                    1..107
                          mol_type = protein
                          organism = synthetic construct
                          note = Description of Artificial Sequence: Synthetic
                           polypeptide
SEQUENCE: 148
EIVLTQSPAT LSLSPGERTT LSCRASQSVN SDLSWYQQKP GQAPRLIIFD ASNRATGIPA   60
RFSGSGSGTD FTLTISSLEP EDFAVYYCQQ RSNWPLTFGG GTKVEFK               107

SEQ ID NO: 149            moltype = AA  length = 107
FEATURE                   Location/Qualifiers
source                    1..107
                          mol_type = protein
                          organism = synthetic construct
                          note = Description of Artificial Sequence: Synthetic
                           polypeptide
SEQUENCE: 149
EIVLTQSPAT LSLSPGERAT LSCRASQNLD TYLAWYQQRP GQAPRLILYD ASNRASGVPA   60
RFTGRGSGTD FTLTISSLEP EDFAVYYCQQ RSIWPLKFGG GSKVEIK               107

SEQ ID NO: 150            moltype = AA  length = 107
FEATURE                   Location/Qualifiers
source                    1..107
                          mol_type = protein
                          organism = synthetic construct
                          note = Description of Artificial Sequence: Synthetic
                           polypeptide
SEQUENCE: 150
EIVLTQSPAT LSLSPGERAT LSCRASQSIS NYLAWFQQKP GQAPRLIIYD ASKRATGIPA   60
RFSGSGSGTD FTLTINSLES EDFAVYYCQQ RDNWPLSFGG GTKVEIK               107

SEQ ID NO: 151            moltype = AA  length = 108
FEATURE                   Location/Qualifiers
source                    1..108
                          mol_type = protein
                          organism = synthetic construct
```

-continued

```
                          note = Description of Artificial Sequence: Synthetic
                            polypeptide
SEQUENCE: 151
EIVLTQSPAT LSLSPGERAT LSCRASQSIS TDLAWYRQKP GQAPRLIFYD ASNRATGIPP  60
RFSGSGSGTD FTLTISSLEP EDFAVYYCQQ RSTWPLNFGG GTKVEIKR              108

SEQ ID NO: 152            moltype = AA  length = 107
FEATURE                   Location/Qualifiers
source                    1..107
                          mol_type = protein
                          organism = synthetic construct
                          note = Description of Artificial Sequence: Synthetic
                            polypeptide
SEQUENCE: 152
EIVLTQSPAT LSLSPGERAT LSCRASQSVS SDLAWYQQKP GQAPRLIIYD ASNRATGIPA  60
RFSGSGSGTD FTLTISSLEP EDFAVYYCHQ RSNWPLTFGG GTKVEIK               107

SEQ ID NO: 153            moltype = AA  length = 107
FEATURE                   Location/Qualifiers
source                    1..107
                          mol_type = protein
                          organism = synthetic construct
                          note = Description of Artificial Sequence: Synthetic
                            polypeptide
SEQUENCE: 153
EIVLTQSPAT LSLSPGERAT LSCRASQSVS SDLAWYQQKP GQAPRLIIYD ASNRATGIPA  60
RFSGSGSGTD FTLTISSLEP EDFAVYYCHQ RSNWPLTFGG GTKVEIK               107

SEQ ID NO: 154            moltype = AA  length = 107
FEATURE                   Location/Qualifiers
source                    1..107
                          mol_type = protein
                          organism = synthetic construct
                          note = Description of Artificial Sequence: Synthetic
                            polypeptide
SEQUENCE: 154
EIVLTQSPAT LSLSPGERAT LSCRASQSVS NSLSWYQQKP GQSPRLIIYD TSKRATGIPA  60
RFSGSGSGTD FTLTISSLET EDFAVYYCHQ RSDWPLTFGG GTKVEIK               107

SEQ ID NO: 155            moltype = AA  length = 113
FEATURE                   Location/Qualifiers
source                    1..113
                          mol_type = protein
                          organism = synthetic construct
                          note = Description of Artificial Sequence: Synthetic
                            polypeptide
SEQUENCE: 155
QVQLVESGGD VVQPGGSLRL SCAASGVAFS NYGMHWVRQA PGKGLEWVAV IWYDGSNKYY  60
ADSVKGRFTI SRDNSKNMLY LQMNSLRAED TAMYYCARND DYWGQGTLVT VSS        113

SEQ ID NO: 156            moltype = AA  length = 119
FEATURE                   Location/Qualifiers
source                    1..119
                          mol_type = protein
                          organism = synthetic construct
                          note = Description of Artificial Sequence: Synthetic
                            polypeptide
SEQUENCE: 156
QVQLVESGGD VVQPGGSLRL SCAASGVVFS DYGMHWVRQA PGKGLEWVAV IWYDGSKKYY  60
GDSVKGRFTI SRDNSKNMLF LEMNSLRVED TAIYYCSRGV RQGPWFVYWG QGTLVTVSA  119

SEQ ID NO: 157            moltype = AA  length = 119
FEATURE                   Location/Qualifiers
source                    1..119
                          mol_type = protein
                          organism = synthetic construct
                          note = Description of Artificial Sequence: Synthetic
                            polypeptide
SEQUENCE: 157
QVQLVESGGD VVQPGGSLRL SCAASGVAFS DYGMHWVRQA PGKGLEWVAV IWYDGSKKYY  60
ADSLKGRFTI SRDNSKNMLY LQMNSLRAED TAMYYCARGI RQGAWFAYWG QGTLVTVSA  119

SEQ ID NO: 158            moltype = AA  length = 120
FEATURE                   Location/Qualifiers
source                    1..120
                          mol_type = protein
                          organism = synthetic construct
                          note = Description of Artificial Sequence: Synthetic
                            polypeptide
```

-continued

```
SEQUENCE: 158
QVQLVESGGD VVQPGGSLRL SCAASGVVFS DYGLYWVRQA PGKGLEWVAL IWFDGSKKFY  60
ADSVKGRFTI SRDNSKNMLY LQMNSLRVDD SAMYYCSRGI RQGPWFAYWG QGTLVTVSPA  120

SEQ ID NO: 159         moltype = AA  length = 119
FEATURE                Location/Qualifiers
source                 1..119
                       mol_type = protein
                       organism = synthetic construct
                       note = Description of Artificial Sequence: Synthetic
                        polypeptide
SEQUENCE: 159
QGHLVESGGD VVLPGGSLRL SCAASGVALS NYGMHWVRQA PGKGLEWVAV IWYDGSKKYY  60
ADSVKGRFTI SRDNSKNMLY LQMISLRAED TAMYYCARGV RQGPWFAYWG QGTLVTVSA  119

SEQ ID NO: 160         moltype = AA  length = 119
FEATURE                Location/Qualifiers
source                 1..119
                       mol_type = protein
                       organism = synthetic construct
                       note = Description of Artificial Sequence: Synthetic
                        polypeptide
SEQUENCE: 160
QVQLVESGGD VVQPGGSLRL SCAASGVVFS NYGMHWVRQA PGKGLEWVAV IWYDGSKKYY  60
GDSVKGRFTI SRDNSKNMLY LQMNSLRVED TAMYYCTRGV RQGPWFAYWG QGTLVTVSA  119

SEQ ID NO: 161         moltype = AA  length = 119
FEATURE                Location/Qualifiers
source                 1..119
                       mol_type = protein
                       organism = synthetic construct
                       note = Description of Artificial Sequence: Synthetic
                        polypeptide
SEQUENCE: 161
QVQLVESGGD VVQPGGSLRL SCAASGVVFS DYGMHWVRQV PGKGLEWVAV IWYDGSRKYY  60
GDSVKGRFTI SRDNSKNMLY LQMSSLRVED TAIYFCSRGI RQGPWFVYWG QGTLVTVSA  119

SEQ ID NO: 162         moltype = AA  length = 119
FEATURE                Location/Qualifiers
source                 1..119
                       mol_type = protein
                       organism = synthetic construct
                       note = Description of Artificial Sequence: Synthetic
                        polypeptide
SEQUENCE: 162
QVQLVESGGD VVQPGGSLRL SCAASGVVFS DYGLHWVRQA PGKGLEWVAV IWYDGSKKFY  60
ADSVKGRFTI SRDNSKNMLY LQMNSLRADD TAMYYCSRGV RQGPWFAYWG QGTLVTVSA  119

SEQ ID NO: 163         moltype = AA  length = 119
FEATURE                Location/Qualifiers
source                 1..119
                       mol_type = protein
                       organism = synthetic construct
                       note = Description of Artificial Sequence: Synthetic
                        polypeptide
SEQUENCE: 163
QVQLVESGGD VVQPGGSLRL SCAASGVVFS DYGLYWVRQA PGKGLEWVAL IWYDGSKKFY  60
ADSVKGRFTI SRDNSKNMLY LQMNSLRADD SAMYYCSRGI RQGPWFAYWG QGTLVTVSP  119

SEQ ID NO: 164         moltype = AA  length = 119
FEATURE                Location/Qualifiers
source                 1..119
                       mol_type = protein
                       organism = synthetic construct
                       note = Description of Artificial Sequence: Synthetic
                        polypeptide
SEQUENCE: 164
QVQLVESGGD VVQPGGSLRL SCAASGVVIS DYGMHWVRQA PGKGLEWVAV IWYDGSKKYY  60
GDSVKGRFTI SRDNSKNMLY LQMNSLRVED TATYYCTRGV RQGPWFVYWG QGTLVRVSA  119

SEQ ID NO: 165         moltype = AA  length = 119
FEATURE                Location/Qualifiers
source                 1..119
                       mol_type = protein
                       organism = synthetic construct
                       note = Description of Artificial Sequence: Synthetic
                        polypeptide
SEQUENCE: 165
QVQLVESGGD VVQPGGSLRL SCAASGVVFS DYGLYWVRQA PGKGLEWVAL IWYDGSKKFY  60
```

```
ADSVKGRFTI SRDNSKNMLY LQMSSSRADD SAMYYCSRGI RQGPWFAYWG QGTLVTVSP     119

SEQ ID NO: 166           moltype = AA  length = 119
FEATURE                  Location/Qualifiers
source                   1..119
                         mol_type = protein
                         organism = synthetic construct
                         note = Description of Artificial Sequence: Synthetic
                          polypeptide
SEQUENCE: 166
QVHLVESGGD VVQPGGSLRL SCAASGVVFS DYGMHWVRQA PGKGLEWVAL IWYDGSKKYY     60
GDSVKGRFTI SRDNSKNMLY LQMNSLRADD TAIYYCTRGV RQGPWFAYWG QGTLVTVSA     119

SEQ ID NO: 167           moltype = AA  length = 119
FEATURE                  Location/Qualifiers
source                   1..119
                         mol_type = protein
                         organism = synthetic construct
                         note = Description of Artificial Sequence: Synthetic
                          polypeptide
SEQUENCE: 167
QVHLVESGGD VVQPGGSLRL SCAASGVVFS DYGMHWVRQA PGKGLEWVAL IWYDGSKKYY     60
GDSVKGRFTI SRDNSKNILY LQMNSLRVDD TAIYYCSRGV RQGPWFAYWG QGTLVTVSA     119

SEQ ID NO: 168           moltype = AA  length = 119
FEATURE                  Location/Qualifiers
source                   1..119
                         mol_type = protein
                         organism = synthetic construct
                         note = Description of Artificial Sequence: Synthetic
                          polypeptide
SEQUENCE: 168
QGHLVESGGD VVLPGGSLRL SCTESGVDLS DFGIHWVRQT PGKGLEWVAL IWYDGSKKFY     60
ADSVKDRFTI SRDNSKNMVY LEMISLRVED TAMYFCARGI RRGPWFTYWG PGTLVTVST     119

SEQ ID NO: 169           moltype = AA  length = 119
FEATURE                  Location/Qualifiers
source                   1..119
                         mol_type = protein
                         organism = synthetic construct
                         note = Description of Artificial Sequence: Synthetic
                          polypeptide
SEQUENCE: 169
QVQLVESGGD VVQPGGSLRL SCAASGVVFS DYGMHWVRQA PGKGLEWVAV IWYDGSRKYY     60
GDSVRGRFTI SRDNSRNILY LQMNSLRVDD TAMYYCARGV RQGPWFAYWG QGTPVIVSA     119

SEQ ID NO: 170           moltype = AA  length = 119
FEATURE                  Location/Qualifiers
source                   1..119
                         mol_type = protein
                         organism = synthetic construct
                         note = Description of Artificial Sequence: Synthetic
                          polypeptide
SEQUENCE: 170
QVQLVESGGD VVQPGGSLRL SCAASGVVFS DYGMHWVRQA PGKGLEWVAL IWYDGSKKYY     60
ADSVKGRFTI SRDNSKNMLY LQMNSLRADD TAMYYCSRGV RQGPWFAYWG QGTLVTVSA     119

SEQ ID NO: 171           moltype = AA  length = 119
FEATURE                  Location/Qualifiers
source                   1..119
                         mol_type = protein
                         organism = synthetic construct
                         note = Description of Artificial Sequence: Synthetic
                          polypeptide
SEQUENCE: 171
QVQLVESGGD VVQPGGSLRL SCAASGVALR DYGMHWVRQT PGKGLEWMAV IWYDGSKKYY     60
ADSLKGRFTI SRDNSKNILY LQMTNLRVED TAIYYCSRGI RQGAWFAYWG QGTLVTVSA     119

SEQ ID NO: 172           moltype = AA  length = 119
FEATURE                  Location/Qualifiers
source                   1..119
                         mol_type = protein
                         organism = synthetic construct
                         note = Description of Artificial Sequence: Synthetic
                          polypeptide
SEQUENCE: 172
QVQLVESGGT VVQPGGSLRL SCAVSGVVFS DYGMHWVRQA PGKGLEWVAL IWYDGTKKYY     60
GDSVKGRFTI SRDNSKNMVY LQMNRLRADD TALYYCTRGI RRGPWFVYWG QGTLVTVSA     119
```

-continued

```
SEQ ID NO: 173              moltype = AA  length = 119
FEATURE                     Location/Qualifiers
source                      1..119
                            mol_type = protein
                            organism = synthetic construct
                            note = Description of Artificial Sequence: Synthetic
                             polypeptide
SEQUENCE: 173
QVHLVESGGD VVQPGGSLRL SCAASGVVFS DYGMHWVRQA PGKGLEWVAL IWYDGSKKYY  60
GDSVKGRFTI SRDNSKNMLY LQMNSLRADD TAIYYCTRGV RQGPWFAYWG QGTLVTVSA  119

SEQ ID NO: 174              moltype = AA  length = 119
FEATURE                     Location/Qualifiers
source                      1..119
                            mol_type = protein
                            organism = synthetic construct
                            note = Description of Artificial Sequence: Synthetic
                             polypeptide
SEQUENCE: 174
QVQLVESGGD VVQPGGSLRL SCAASGVVFS DYGLHWVRQA PGKGLEWVAV IWYDGSKKYY  60
GDSVKGRFTI SRDNSKSVLF LQMNSLRVED TAMYYCARGV RQGPWFAYWG QGTLVTVSA  119

SEQ ID NO: 175              moltype = AA  length = 119
FEATURE                     Location/Qualifiers
source                      1..119
                            mol_type = protein
                            organism = synthetic construct
                            note = Description of Artificial Sequence: Synthetic
                             polypeptide
SEQUENCE: 175
QVHLVESGGD VVLPGGSLRL SCAASGVAFS NYGMHWVRQA PGKGLEWVAV IWYDGSKKYY  60
ADSVKGRFTI SRDNSKNMLY LQMISLRAED TAMYYCARGV RQGPWFAYWG QGTLVTVSA  119

SEQ ID NO: 176              moltype = AA  length = 119
FEATURE                     Location/Qualifiers
source                      1..119
                            mol_type = protein
                            organism = synthetic construct
                            note = Description of Artificial Sequence: Synthetic
                             polypeptide
SEQUENCE: 176
QVQLVESGGD VVQPGGSLRL SCAASGVVFS DYGLSWVRQA PGKGLEWVAL IWFDGSKKFY  60
ADSVKGRFTI SRDNSKNMLY LQMNSLRADD SAVYYCSRGI RQGPWFAYWG QGTLVTVSP  119

SEQ ID NO: 177              moltype = AA  length = 119
FEATURE                     Location/Qualifiers
source                      1..119
                            mol_type = protein
                            organism = synthetic construct
                            note = Description of Artificial Sequence: Synthetic
                             polypeptide
SEQUENCE: 177
QVQLVESGGD VVQPGGSLRL SCAASGVAFS NYGMHWVRQA PGKGLEWVAV IWYDGSNKYY  60
GDSVKGRFTI SRDNSKNMLY LQMNSLRAED TAMYYCARGV RQGPWFAYWG QGTLVTVSA  119

SEQ ID NO: 178              moltype = AA  length = 119
FEATURE                     Location/Qualifiers
source                      1..119
                            mol_type = protein
                            organism = synthetic construct
                            note = Description of Artificial Sequence: Synthetic
                             polypeptide
SEQUENCE: 178
QVQLVESGGD VVQPGGSLRL SCAASGVVFS DYGMHWVRQA PGKGLEWVGV IWYDGSKKYY  60
ADSLKGRFTI SRDNSKNMLY LQMNSLRAED TAIYYCSRGV RQGAWFAYWG QGTRVTVSA  119

SEQ ID NO: 179              moltype = AA  length = 119
FEATURE                     Location/Qualifiers
source                      1..119
                            mol_type = protein
                            organism = synthetic construct
                            note = Description of Artificial Sequence: Synthetic
                             polypeptide
SEQUENCE: 179
QVQLVESGGD VVQPGGSLRL SCAASGVAFS DYGMHWVRQA PGKGLEWVAV IWYDGSRKYY  60
ADSLKGRFTI SRDNSKNMLY LQMNSLRAED TAIYYCSRGV RQGAWFAYWG QGTRVTVSA  119

SEQ ID NO: 180              moltype = AA  length = 119
FEATURE                     Location/Qualifiers
```

-continued

```
source                   1..119
                         mol_type = protein
                         organism = synthetic construct
                         note = Description of Artificial Sequence: Synthetic
                           polypeptide
SEQUENCE: 180
QVQLVESGGD VVQPGGSLRL SCAASGVVFS DYGMHWVRQA PGKGLEWVAV IWYDGSKKYY  60
GDSVKGRFTI SRDNSKNMLY LQMNSLRVED TATYYCARGV RQGPWFVYWG QGTLVSVSA   119

SEQ ID NO: 181          moltype = AA  length = 119
FEATURE                 Location/Qualifiers
source                  1..119
                        mol_type = protein
                        organism = synthetic construct
                        note = Description of Artificial Sequence: Synthetic
                          polypeptide
SEQUENCE: 181
QVQLVESGGD VVQPGGSLRL SCAASGVVFS DYGLYWVRQA PGKGLEWVAL IWYDGSKKFY  60
ADSVKGRFTI SRDNSKNMLY LQMNSLRADD SAMYYCSRGI RQGPWFAYWG QGTLVTVSP   119

SEQ ID NO: 182          moltype = AA  length = 119
FEATURE                 Location/Qualifiers
source                  1..119
                        mol_type = protein
                        organism = synthetic construct
                        note = Description of Artificial Sequence: Synthetic
                          polypeptide
SEQUENCE: 182
QVQLVESGGD VVQPGGSLRL SCAASGVAFS DYGMHWVRQA PGKGLEWVAV IWYDGSRKYY  60
ADSLKGRFTI SRDNSKNMLY LQMNSLRAED TAMYYCSRGV RQGAWFAYWG QGTRVTVSA   119

SEQ ID NO: 183          moltype = AA  length = 119
FEATURE                 Location/Qualifiers
source                  1..119
                        mol_type = protein
                        organism = synthetic construct
                        note = Description of Artificial Sequence: Synthetic
                          polypeptide
SEQUENCE: 183
QVQLVESGGD VVQPGGSLRL SCAASGVAFS DYGMHWVRQT PGRGLEWMAV IWYDGTKKYY  60
ADSLRGRFTI SRDNSKNILF LQMTNLRVED TAIYYCSRGI RQGAWFAYWG QGTLVTVSA   119

SEQ ID NO: 184          moltype = AA  length = 119
FEATURE                 Location/Qualifiers
source                  1..119
                        mol_type = protein
                        organism = synthetic construct
                        note = Description of Artificial Sequence: Synthetic
                          polypeptide
SEQUENCE: 184
QVQLVESGGD VVQPGGSLRL SCAASGVVFS DYGLYWVRQA PGKGLEWVAL IWYDGSKKFY  60
ADSVKGRFTI SRDNSKNMLY LQMNSLRADD SAMYYCSRGI RQGPWFAYWG QGTLVTVSP   119

SEQ ID NO: 185          moltype = AA  length = 119
FEATURE                 Location/Qualifiers
source                  1..119
                        mol_type = protein
                        organism = synthetic construct
                        note = Description of Artificial Sequence: Synthetic
                          polypeptide
SEQUENCE: 185
QVQLVESGGD VVQPGGSLRL SCAASGVAFS DYGMHWVRQA PGKALEWVAV IWYDGSKKYY  60
ADSLKGRFTI SRDNSKNMLY LQMNSLRAED TAMYYCSRGV RQGAWFAYWG QGTLVTVSA   119

SEQ ID NO: 186          moltype = AA  length = 119
FEATURE                 Location/Qualifiers
source                  1..119
                        mol_type = protein
                        organism = synthetic construct
                        note = Description of Artificial Sequence: Synthetic
                          polypeptide
SEQUENCE: 186
QVQLVESGGD VVQPGGSLRL SCAASGVVFS DYGLYWVRQA PGKGLEWVAL IWYDGSKKFY  60
ADSVKGRFTI SRDNSKNMLY LQMNSLRADD SAMYYCSRGI RQGPWFAYWG QGTLVTVSP   119

SEQ ID NO: 187          moltype = AA  length = 119
FEATURE                 Location/Qualifiers
source                  1..119
                        mol_type = protein
```

```
                        organism = synthetic construct
                        note = Description of Artificial Sequence: Synthetic
                          polypeptide
SEQUENCE: 187
QVHLVESGGD VVQPGGSLRL SCAASGVVFS DYGMHWVRQA PGKGLEWVAL IWYDGSKKYY  60
GDSVKGRFTI SRDNSKNMLY LQMNSLRADD TAIYYCTRGV RQGPWFAYWG QGTLVTVSA   119

SEQ ID NO: 188         moltype = AA  length = 119
FEATURE                Location/Qualifiers
source                 1..119
                        mol_type = protein
                        organism = synthetic construct
                        note = Description of Artificial Sequence: Synthetic
                          polypeptide
SEQUENCE: 188
QVQLVESGGK VVQPGGSLRL SCAVSGVVFS DYGIHWVRQA PGKGLEWVAL IWFDGSKKYY  60
GDSVKGRFTI SRDNSKNMVY LQMNSLRADD TALYYCTRGI RQGPWFVYWG QGTLVTVST   119

SEQ ID NO: 189         moltype = AA  length = 119
FEATURE                Location/Qualifiers
source                 1..119
                        mol_type = protein
                        organism = synthetic construct
                        note = Description of Artificial Sequence: Synthetic
                          polypeptide
SEQUENCE: 189
QVQLVESGGD VVQPGGSLRL SCAASGVVFS DYGLYWVRQA PGKGLEWVAL IWYDGSKKFY  60
ADSVKGRFTI SRDNSKNMLY LQMNSLRADD SAMYYCSRGI RQGPWFAYWG QGTRVTVSP   119

SEQ ID NO: 190         moltype = AA  length = 119
FEATURE                Location/Qualifiers
source                 1..119
                        mol_type = protein
                        organism = synthetic construct
                        note = Description of Artificial Sequence: Synthetic
                          polypeptide
SEQUENCE: 190
QVQLVESGGD VVQPGGSLRL SCAASGVVFS DYGMHWVRQA PGKGLEWVAL IWYDGSKKYY  60
ADSVKGRFTI SRDNFKNMLY LQMNSLRADD TAMYYCSRGV RQGPWFAYWG QGTLVTVSA   119

SEQ ID NO: 191         moltype = AA  length = 121
FEATURE                Location/Qualifiers
source                 1..121
                        mol_type = protein
                        organism = synthetic construct
                        note = Description of Artificial Sequence: Synthetic
                          polypeptide
SEQUENCE: 191
QCQVQLVESG GDVVQPGGSL RLSCAASGVA FSDYGMHWVR QAPGKGLEWV AVIWYDGSRK  60
YYADSLKGRF TISRDNSKNM LYLQMNSLRA EDTAIYYCSR GVRQGAWFAY WGQGTRVTVS  120
A                                                                  121

SEQ ID NO: 192         moltype = AA  length = 119
FEATURE                Location/Qualifiers
source                 1..119
                        mol_type = protein
                        organism = synthetic construct
                        note = Description of Artificial Sequence: Synthetic
                          polypeptide
SEQUENCE: 192
RVQLVESGGD VVQPGDSLRL SCSVSGVVFS DYGMHWVRQA PGKGLEWVAV IWYDGSKKYY  60
ADSVKGRFTI SRDNSKNILY LQMNSLRAED TAIYYCTRGI RQGPWFVYWG QGTLVTVSA   119

SEQ ID NO: 193         moltype = AA  length = 119
FEATURE                Location/Qualifiers
source                 1..119
                        mol_type = protein
                        organism = synthetic construct
                        note = Description of Artificial Sequence: Synthetic
                          polypeptide
SEQUENCE: 193
QGQLVESGGD VVRPGGSLRL SCVASGVAFS DYGMHWVRQA PGKGLEWVAV IWYDGSRRYY  60
ADSLKGRFTI SRDNSKNTLY LQMNSLRAED TAMYYCSRGV RQGAWFAYWG QGTLVTVSA   119

SEQ ID NO: 194         moltype = AA  length = 119
FEATURE                Location/Qualifiers
source                 1..119
                        mol_type = protein
                        organism = synthetic construct
```

```
                         note = Description of Artificial Sequence: Synthetic
                            polypeptide
SEQUENCE: 194
QVQLVESGGD VVQPGGSLRL SCAASGVAFS DYGMHWVRQA PGKGLEWVAV IWFDGSKKYY   60
ADSLKGRFTI SRDNSKNMLY LQMNSLRAED TAMYYCTRGI RQGAWFAYWG QGTLVTVSA    119

SEQ ID NO: 195          moltype = AA  length = 119
FEATURE                 Location/Qualifiers
source                  1..119
                        mol_type = protein
                        organism = synthetic construct
                        note = Description of Artificial Sequence: Synthetic
                           polypeptide
SEQUENCE: 195
QVQLVESGGD VVQPGGSLRL SCAASGVVFS DYGLYWVRQA PGKGLEWVAL IWYDGSKKFY   60
ADSVKGRFSI SRDNSKNMLY LQMNNLRADD SAIYYCSRGI RQGPWFAYWG QGTRVTVSP    119

SEQ ID NO: 196          moltype = AA  length = 119
FEATURE                 Location/Qualifiers
source                  1..119
                        mol_type = protein
                        organism = synthetic construct
                        note = Description of Artificial Sequence: Synthetic
                           polypeptide
SEQUENCE: 196
QGQLVESGGD VVQPGGSLRL SCAASGVAFS DYGMHWVRQA PGKGLEWVAV IWFDGSKKYY   60
GDSVKGRFTI SRDNSKNMLY LQMNSLRVDD TAIYYCSRGI RQGPWFVYWG QGTLVTVSE    119

SEQ ID NO: 197          moltype = AA  length = 123
FEATURE                 Location/Qualifiers
source                  1..123
                        mol_type = protein
                        organism = synthetic construct
                        note = Description of Artificial Sequence: Synthetic
                           polypeptide
SEQUENCE: 197
QVQLVESGGD VVQPGGSLRL SCSASGLVFR DYGMNWVRQA PGKGLEWVGL IWYDGTKKYY   60
SDFVKGRFTI SRDNSKNMLY LQMNNLRAED TAIYYCARFL IGATRRGNAM DYWGQGTSVI  120
VSS                                                               123

SEQ ID NO: 198          moltype = AA  length = 123
FEATURE                 Location/Qualifiers
source                  1..123
                        mol_type = protein
                        organism = synthetic construct
                        note = Description of Artificial Sequence: Synthetic
                           polypeptide
SEQUENCE: 198
QVQLVESGGD VVQPGGSLRL SCSASGLVIS DYGMNWVRQA PGKGLEWVGL IWYDGSKKYY   60
SDFVKGRFTI SRDNSKNILY LQMNNLRAED TAMYYCARFL IGATRRGNAM DYWGQGTSVT  120
VSS                                                               123

SEQ ID NO: 199          moltype = AA  length = 123
FEATURE                 Location/Qualifiers
source                  1..123
                        mol_type = protein
                        organism = synthetic construct
                        note = Description of Artificial Sequence: Synthetic
                           polypeptide
SEQUENCE: 199
QVQLVESGGD VVQPGGSLRL SCSASGLVIS DYGMNWVRQA PGKGLEWVGL IWYDGSKKYY   60
SDFVKGRFTI SRDNSKNILY LQMNNLRAED TAMYYCARFL IGATRRGNAM DYWGQGTSVT  120
VSS                                                               123

SEQ ID NO: 200          moltype = AA  length = 123
FEATURE                 Location/Qualifiers
source                  1..123
                        mol_type = protein
                        organism = synthetic construct
                        note = Description of Artificial Sequence: Synthetic
                           polypeptide
SEQUENCE: 200
QVQLVESGGD VVQPGGSLRL SCSASGLVFR DYGMNWVRQA PGKGLEWVGL IWYDGTKKYY   60
SDFVKGRFTI SRDNSKNMLY LQMNNLRAED TAMYYCARFL IGATRRGNAM DYWGQGTSVI  120
VSS                                                               123

SEQ ID NO: 201          moltype = AA  length = 123
FEATURE                 Location/Qualifiers
source                  1..123
```

-continued

```
                          mol_type = protein
                          organism = synthetic construct
                          note = Description of Artificial Sequence: Synthetic
                            polypeptide
SEQUENCE: 201
QVQLVESGGD VVQPGGSLRL SCSASGLVIS DYGMNWVRQA PGKGLEWVGL IWYDGSKKYY   60
SDFVKGRFTI SRDNSKNILY LQMNNLRAED TAMYYCARFL IGATRRGNAM DYWGQGTSVT  120
VSS                                                                123

SEQ ID NO: 202            moltype = AA   length = 123
FEATURE                   Location/Qualifiers
source                    1..123
                          mol_type = protein
                          organism = synthetic construct
                          note = Description of Artificial Sequence: Synthetic
                            polypeptide
SEQUENCE: 202
QVQLVESGGD VVQPGGSLRL SCSASGLVIS DYGMNWVRQA PGKGLEWVGL IWYDGSKKYY   60
SDFVKGRFTI SRDNSKNILY LQMNNLRAED TAMYYCARFL IGATRRGNAM DYWGQGTSVT  120
VSS                                                                123

SEQ ID NO: 203            moltype = AA   length = 123
FEATURE                   Location/Qualifiers
source                    1..123
                          mol_type = protein
                          organism = synthetic construct
                          note = Description of Artificial Sequence: Synthetic
                            polypeptide
SEQUENCE: 203
QVQLVESGGD VVQPGGSLRL SCSTSGLVFS DYGMNWVRQA PGKGLEWVGL IWFDGSKKYY   60
SDFVKGRFTI SRDNSKNMLY LQMNNLRAED TAIYYCARFL IGATRRGNAM DYWGQGTSVT  120
VSP                                                                123

SEQ ID NO: 204            moltype = AA   length = 123
FEATURE                   Location/Qualifiers
source                    1..123
                          mol_type = protein
                          organism = synthetic construct
                          note = Description of Artificial Sequence: Synthetic
                            polypeptide
SEQUENCE: 204
QVQLVESGGD VVQPGGSLRL SCVASGVAFS NYGMHWVRQA PGKGLEWVAI IWYDGTNKYY   60
ADSVKGRFTI SRDNSKNILY LQMNSLRAED TAIYYCARLS IGTTHYFDMD DYWGQGTSVI  120
VSS                                                                123

SEQ ID NO: 205            moltype = AA   length = 123
FEATURE                   Location/Qualifiers
source                    1..123
                          mol_type = protein
                          organism = synthetic construct
                          note = Description of Artificial Sequence: Synthetic
                            polypeptide
SEQUENCE: 205
QVQLVESGGD VVQPGGSLRL SCAASGVAFS NYGMHWVRQA PGKGLEWVAI IWYDGSNKYY   60
ADSVKGRFTI SRDNSKNMLY LQMNSLRAED TAMYYCARLS IGTTHYFDTD DYWGQGTSVT  120
VSS                                                                123

SEQ ID NO: 206            moltype = AA   length = 123
FEATURE                   Location/Qualifiers
source                    1..123
                          mol_type = protein
                          organism = synthetic construct
                          note = Description of Artificial Sequence: Synthetic
                            polypeptide
SEQUENCE: 206
QVQLVESGGD VVQPGGSLRL SCAASGVAFS NYGMHWVRQA PGKGLEWVAI IWYDGSNKYY   60
ADSVKGRFTI SRDNSKNMLY LQMNSLRAED TAMYYCARLS IGTTHYFDTD DYWGQGTSVT  120
VSS                                                                123

SEQ ID NO: 207            moltype = AA   length = 123
FEATURE                   Location/Qualifiers
source                    1..123
                          mol_type = protein
                          organism = synthetic construct
                          note = Description of Artificial Sequence: Synthetic
                            polypeptide
SEQUENCE: 207
QVQLVESGGD VVQPGGSLRL SCAASGVAFR NYGMHWVRQA PGKGLEWVAI IWYDGSNKYY   60
ADSVKGRFTI SRDNSKNMLY LQMNSLRAED TAMYYCARLS IGTTHYFDTD DYWGQGTSVT  120
```

-continued

```
VSS                                                                  123

SEQ ID NO: 208          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 208
QVQLVESGGD VVQPGGSLRL SCAASGVAFR NYGMHWVRQA PGKGLEWVAI IWYDGSNKYY   60
ADSVKGRFTI SRDNSKNMLY LQMDSLRAED TAMYYCARLS IGTTHYFDTD DYWGQGTSVT  120
VSS                                                                  123

SEQ ID NO: 209          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 209
QVQLVESGGD VVQPGGSLRL SCAASGVAFS NYGMHWVRQA PGKGLEWVAI IWYDGSNKYY   60
TDSVKGRFTI SRDNSKNMLY LQMNSLRAED TAMYYCARLS IGTTHYFDTD DYWGQGTSVT  120
VSS                                                                  123

SEQ ID NO: 210          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 210
QVQLVESGGD VVQPGGSLRL SCAASGVAFS NYGMHWVRQA PGKGLEWVAI IWFDGSNKYY   60
ADSVKGRFTI SRDNSKNMLY LQMKSLRAED TAMYYCARLS IGTTHYFDTD DYWGQGTSVT  120
VSS                                                                  123

SEQ ID NO: 211          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 211
QVQLVESGGD VVQPGGSLKL SCAASGVAFS NYGMHWVRQA PGKGLEWVAI IWYDGSNKYY   60
TDSVKGRFTI SRDNSKNMLY LQMNSLRAED TAMYYCARLS IGTTHYFDMD DYWGQGTSVT  120
VSS                                                                  123

SEQ ID NO: 212          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 212
QVQLVESGGD VVQPGGSLRL SCAASGVAFS NYGMHWVRQA PGKGLEWVAI IWYDGSNKYY   60
TDSVKGRFTI SRDNSKNMLY LQMNSLRAED TAMYYCARLS IGATHYFDTD DYWGQGTSVT  120
VSS                                                                  123

SEQ ID NO: 213          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 213
QVQLVESGGD VVQPGGSLRL SCAASGVAFS NYGMHWVRQA PGKGLEWVAI IWYDGSNKYY   60
ADSVKGRFTI SRDNSKNMLY LQMNSLRAED TAMYYCARLS IGTTHYFDTD DYWGQGTSVT  120
VSS                                                                  123

SEQ ID NO: 214          moltype = AA  length = 121
FEATURE                 Location/Qualifiers
source                  1..121
                        mol_type = protein
                        organism = synthetic construct
```

```
                              note = Description of Artificial Sequence: Synthetic
                              polypeptide
SEQUENCE: 214
QVRLVESGGD VVQPGGSLRL SCAASGVAFS DYGMHWVRQA PGKGLEWVAV IWYDGSKKYY    60
VDSVKGRFTI SRDNSKNMLY LQMNSLRAED TAMYYCARFL IGTAGDVMDY WGQGTSVTVS   120
S                                                                    121

SEQ ID NO: 215           moltype = AA  length = 119
FEATURE                  Location/Qualifiers
source                   1..119
                         mol_type = protein
                         organism = synthetic construct
                         note = Description of Artificial Sequence: Synthetic
                            polypeptide
SEQUENCE: 215
QVQLVESGGD VVQPGGSLRL SCAASGVAFS NYGMHWVRQA PGKGLEWVAV IWYDGSNKYY    60
ADSVKGRFTI SRDNSKNMLY LQMNSLRAED TAMYYCARGY SSGYDLAYWG QGTLVTVSA    119

SEQ ID NO: 216           moltype = AA  length = 121
FEATURE                  Location/Qualifiers
source                   1..121
                         mol_type = protein
                         organism = synthetic construct
                         note = Description of Artificial Sequence: Synthetic
                            polypeptide
SEQUENCE: 216
QVQLVESGGD VVQPGGSLRL SCAASGVAFS NFGMHWVRQA PGKGLEWVAV IWYDGSNKYY    60
GDSVKGRFTI SRDNSKNILY LQMNNLRAED TAMYYCAREG LRWYFDVDDY WGAGTTVTVS   120
S                                                                    121

SEQ ID NO: 217           moltype = AA  length = 107
FEATURE                  Location/Qualifiers
source                   1..107
                         mol_type = protein
                         organism = synthetic construct
                         note = Description of Artificial Sequence: Synthetic
                            polypeptide
SEQUENCE: 217
EIVLTQSPAT LSLSPGERAT LSCRASQSVS SYLAWYQQKP GQAPRLIIYD ASNRATGIPA    60
RFSGSGSGTD FTLTISSLEP EDFAVYYCQQ RSNWPLTFGG GTKVEIK                 107

SEQ ID NO: 218           moltype = AA  length = 107
FEATURE                  Location/Qualifiers
source                   1..107
                         mol_type = protein
                         organism = synthetic construct
                         note = Description of Artificial Sequence: Synthetic
                            polypeptide
SEQUENCE: 218
EIVLTQSPAT LSMSPGERAT LSCRASQSVS SSLAWFQQRP GQAPRLIIYD ASNRATGIPA    60
RFRGSGSGTD FTLTISSLEP EDFAIYYCQQ RDNWPLTFGG GTKVEIR                 107

SEQ ID NO: 219           moltype = AA  length = 107
FEATURE                  Location/Qualifiers
source                   1..107
                         mol_type = protein
                         organism = synthetic construct
                         note = Description of Artificial Sequence: Synthetic
                            polypeptide
SEQUENCE: 219
DIVLTQSPAT LSLSPGERAT LSCRASQSIS SDLTWFQQKP GQAPRLIIHD ASNRATGIPA    60
RFSGSGSGTD FTLTISSLEP EDFAVYYCLQ RSDWPLTFGG GTKVEIK                 107

SEQ ID NO: 220           moltype = AA  length = 107
FEATURE                  Location/Qualifiers
source                   1..107
                         mol_type = protein
                         organism = synthetic construct
                         note = Description of Artificial Sequence: Synthetic
                            polypeptide
SEQUENCE: 220
EVVLTQSPAT LSLSPGERAT LSCRASQSVR NSLAWFQQKP GQAPRLIIYD ASNRAAGIPP    60
RFSGGGSGTD FTLTISSLEP EDFAIFYCQQ RGDWPLTFGG GTKVEIK                 107

SEQ ID NO: 221           moltype = AA  length = 107
FEATURE                  Location/Qualifiers
source                   1..107
                         mol_type = protein
                         organism = synthetic construct
```

```
                      note = Description of Artificial Sequence: Synthetic
                      polypeptide
SEQUENCE: 221
DIVLTQSPAT LSLSPGERAT LSCRASQSIS NDLTWFQQRP GQAPRLIIHD ASNRATGIPA   60
RFSGSGSGTD FTLTISRLEP EDFAVYYCLQ RSDWPLTFGG GTKVEIK                 107

SEQ ID NO: 222        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 222
EIVLTQSPAT LSLSPGERAT LSCRASQSIS SDLAWFQQKP GQAPRLIIHD ASNRATGIPA   60
RFSGSGSGTD FTLTISSLEP EDFAFYYCQQ RSDWPITFGG GTKVEIK                 107

SEQ ID NO: 223        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 223
EIVLTQSPVI LSLSPGERAT LSCRASQSIS SDLAWFQQTP GQAPRLIIYD ASNRATGIPA   60
RFSGSGSGTD FTLTISSLEP EDFAVYYCQQ RSNWPLTFGG GTKVEIK                 107

SEQ ID NO: 224        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 224
EIVLTQSPAT LSLSPGERAT LSCRASQSIS SDLAWFQQIP GQAPRLIIHD ASNRATGIPA   60
RFSGRGSGTD FTLTISGLEP EDFAVYYCQQ RSDWPLTFGG GTKVEIK                 107

SEQ ID NO: 225        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 225
EIVLTQSPAT LSLSPGERAT LSCRASQSIS SDLAWFQQKP GRAPRLIIYD ASNRATGIPA   60
RFSGSGSGTG FTLTISSLEP EDFAVYYCQQ RSDWPVTFGG GTKVEIR                 107

SEQ ID NO: 226        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 226
EIVLTQSPAT LSLSPGARAT LSCRASQSIS SDLAWFQQKP GQAPRLIIHD ASNRATGIPA   60
RFSGSGSGTD FTLTISNLEP EDFAVYYCQQ RSDWPVTFGG GTKVEIK                 107

SEQ ID NO: 227        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 227
EIVLTQSPAT LSLSPGERAT LSCRASQSIS SDLTWFQQKP GQAPRLIIYD ASNRATGIPA   60
RFSGSGSGTD FTLTISSLEP EDFAVYYCLQ RSDWPLTFGG GTKVEIK                 107

SEQ ID NO: 228        moltype = AA  length = 107
FEATURE               Location/Qualifiers
source                1..107
                      mol_type = protein
                      organism = synthetic construct
                      note = Description of Artificial Sequence: Synthetic
                      polypeptide
```

```
SEQUENCE: 228
EIVLTQSPAT LSLSPGERAT LSCRASQSIS SDLAWFQQKP GQAPRLIIHD ASKRATGIPG  60
RFWGSGSGTD FTLTISGLEP EDFAVYYCQQ RSNWPLTFGG GTKVEIK                107

SEQ ID NO: 229         moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 229
EIVLTQSPAT LSLSPGERAT LSCRASQSIS SDLAWFQQKP GQAPRLIIHD ASNRATGIPA  60
RFSGRGSGTD FTLTISSLEP DDFAVYYCQQ RSDWPLTFGG GTKVEIK                107

SEQ ID NO: 230         moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 230
EIVLTQSPVT LSLSPGDRAT LSCRASQSVT NSLSWFQQKL GQAPRLIIYD ASNRATGIPA  60
RFSGSGSGTD FTLTISSLEP EDFAVYYCQQ RDNWPLTFGG GTKVEIK                107

SEQ ID NO: 231         moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 231
EIVLTQSPAT LSLSPGERAT LSCRASQSIS SDLAWFQQRP GQAPRLIIYD GSNRATGIPA  60
RFSGRGSGTD FTLTISSLEP EDFAAYYCQQ RSDWPLTFGG GTKVEIK                107

SEQ ID NO: 232         moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 232
EIVLTQSPAT LSLSPGERVT LSCRASQSVS SDLAWFQQKP GQAPRLIIYD ASNRATGIPA  60
RFSGSGSGTD FTLTISSLET EDFAVYYCQQ RSAWPPTFGG GTKVEIK                107

SEQ ID NO: 233         moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 233
EIVLTQSPAT LSLSPGERAT LSCRASQSIS SDLTWFQQKP GQAPRLIIYD ASNRATGIPA  60
RFSGSGSGTD FTLTISSLEP EDFVVYYCLQ RSDWPLTFGG GTKVEIK                107

SEQ ID NO: 234         moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 234
EIVLTQSPAT LSLSPGERAT LSCRASQSVA NSLAWFQQKP GQAPRLIIYD ASNRATGIPV  60
RFSGSGSGTD FTLTISSLEL EDFAVYYCQQ RDNWPLTFGG GTKVEIK                107

SEQ ID NO: 235         moltype = AA  length = 107
FEATURE                Location/Qualifiers
source                 1..107
                       mol_type = protein
                       organism = synthetic construct
                       note = Description of Artificial Sequence: Synthetic
                        polypeptide
SEQUENCE: 235
EVVLTQSPAT LSLSPGERAT LSCRASQSID SDLAWSQQKT GQPPRLIIYD ASNRATGIPA  60
```

```
RFSGSGSGTD FTLTISSLEP EDFAVYYCQQ RSDWPLTFGG GTKVEIR                107

SEQ ID NO: 236        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 236
EVVLTQSPAT LSLSPGERAT LSCRASQSID SDLAWSQQKP GQPPRLIIYD ASNRATGIPA   60
RFSGSGSGTD FTLTISSLEP EDFAVYYCQQ RSDWPLTFGG GTKVEIR                107

SEQ ID NO: 237        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 237
KFVLPQSPAT LSLSPGERAT LSCRASQSID SDLAWSQQKP GQPPRLIIYD ASNRATGIPA   60
RFSGSGSGTV FTLTISSLEP EDFAVYYCQQ RSDWPLTFGG GTKVEIR                107

SEQ ID NO: 238        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 238
EVVLTQSPAT LSLSPGERAT LSCRASQSID SDLAWSQQKP GQPPRLIIYD ASNRATGIPA   60
RFSGSGSGTD FTLTISSLED EDFAVYYCQQ RSDWPLTFGG GTKVEIR                107

SEQ ID NO: 239        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 239
EVVLTQSPAT LSLSPGERAT LSCRASQSID SDLAWSQQKP GQPPRLIIYD ASNRATGIPA   60
RFSGSGSGTD FTLTISSLEP EDFAVYYCQQ RSDWPLTFGG GTKVEIR                107

SEQ ID NO: 240        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 240
EIVLTQSPAT LSLSPGERAT LSCRASQSVS SYLAWYQQKP GQAPKLIIYD ASNRATGIPA   60
RFSGSGSGTD FTLTITSLDL EDFAVYYCQQ RSAWPLTFGG GTKVEIR                107

SEQ ID NO: 241        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 241
EIVLTQSPAT LSLSPGERAT LSCRASQSVS SYLAWYQQKV GQAPRLIIFD ASNRATGIPA   60
RFSGSGSGTD FTLTITSLDP EDFAVYYCQQ RSAWPLTFGG GTKVEIR                107

SEQ ID NO: 242        moltype = AA  length = 107
FEATURE               Location/Qualifiers
source                1..107
                      mol_type = protein
                      organism = synthetic construct
                      note = Description of Artificial Sequence: Synthetic
                      polypeptide
SEQUENCE: 242
EIVLTQSPAT LSLSPGERAS LSCRASQSVS SYLAWYQQKV GQAPRLIIFD ASNRATGIPA   60
RFSGSGSGTD FTLTITSLDP EDFAVYYCQQ RSAWPLTFGG GTKVEIR                107
```

```
SEQ ID NO: 243           moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 243
EIVLTQSPAT LSLSPGERAT LSCRASQSVS SYLAWYQQKV GQAPRLIIFD ASNRATGIPA  60
RFSGSGSGTD FTLTITSLDP EDFAVYYCQQ RSAWPLTFGG GTKVEIR               107

SEQ ID NO: 244           moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 244
EIVLTQSPAT LSLSPGERAT LSCRASQSVS SYLAWYQQKV GQAPRLIIFD ASNRATGIPA  60
RFSGSGSGTD FTLTITSLDP EDFAVYYCQQ RSAWPLTFGG GTKVEIR               107

SEQ ID NO: 245           moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 245
EIVLTQSPAT LSLSPGERAT LSCRASQSVS SYLAWYQQKP GQAPRLIIFD TSNRATGIPA  60
RFSGSGSGTD FTLTITSLDP EDFAVYYCQQ RSAWPLTFGG GTKVEIR               107

SEQ ID NO: 246           moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 246
EIVLTQSPAT LSLSPGERAT LTCRASQSVS SYLAWYQQKV GQAPRLIIFD ASNRATGIPA  60
RFSGSGSGTE FTLTITSLDP EDFAVYYCQQ RSAWPLTFGG GTKVEIR               107

SEQ ID NO: 247           moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 247
EIVLTQSPAT LSLSPGERAT LSCRASQSVS SYLAWYQQKV GQAPRLIIFD ASNRATGIPA  60
RFSGSGSGTD FTLTITSLDP EDFAVYYCQQ RSAWPLTFGG GTKVEIR               107

SEQ ID NO: 248           moltype = AA  length = 107
FEATURE                  Location/Qualifiers
source                   1..107
                         mol_type = protein
                         organism = synthetic construct
                         note = Description of Artificial Sequence: Synthetic
                          polypeptide
SEQUENCE: 248
EIVLTQSPAT LSLSPGERAT LSCRASQSVS SYLAWFQQKP GQAPRLIIYD AFNRATGIPA  60
RFSGSGSGTD FTLTISSLEP EDFAVYYCLQ RSNWPLTFGG GTKVEIK               107
```